United States Patent [19]

Heinemann et al.

[11] Patent Number: 5,739,291
[45] Date of Patent: Apr. 14, 1998

[54] GLUTAMATE RECEPTOR ANTIBODIES

[75] Inventors: Stephen F. Heinemann, La Jolla; James R. Boulter, San Diego; Michael Hollmann, Del Mar; Bernhard Bettler, Solana Beach; Jan Egebejerg Jensen, San Diego, all of Calif.

[73] Assignee: The Salk Institute For Biological Studies, La Jolla, Calif.

[21] Appl. No.: 481,206

[22] Filed: Jun. 6, 1995

Related U.S. Application Data

[60] Continuation of Ser. No. 13,767, Feb. 4, 1993, abandoned, which is a division of Ser. No. 718,575, Jun. 21, 1991, Pat. No. 5,202,257, which is a continuation-in-part of Ser. No. 428,116, Oct. 27, 1989, abandoned.

[51] Int. Cl.$^6$ .................................................. C07K 16/28
[52] U.S. Cl. ........................ 530/388.22; 530/389.1; 530/387.9
[58] Field of Search .................... 530/388.22, 389.1, 530/387.9; 435/70.21, 240.26, 240.27

[56] References Cited

U.S. PATENT DOCUMENTS 4,857,637  8/1989  Hammonds et al. .................. 530/403

OTHER PUBLICATIONS

Osband et al., Immund Today, 1990, 11:193.

Harris et al., TiBTech, 1993, 11:43.

Hampson et al., J Biol Chem., 264:13329, 1989.

Hampson et al., J Biol Chem, 263:2500, 1988.

*Primary Examiner*—Christina Y. Chan
*Assistant Examiner*—Emma Cech
*Attorney, Agent, or Firm*—Stephen E. Reiter; Gray Cary Ware & Freidenrich

[57] ABSTRACT

The present invention discloses novel DNAs that encode proteins having electrophysiological and pharmacological properties characteristic of glutamate receptors. The glutamate receptors are exemplified by proteins encoded by representative cDNA clones GluR1, GluR2, GluR3, GluR4, GluR5, GluR6 and GluR7, fragments thereof, and functional combinations of these glutamate receptor proteins and/or fragments. DNA sequences from the cDNA clones for GluR1, GluR2, GluR3, GluR5 and GluR5 are especially useful as probes, thus enabling those skilled in the art to identify, without undue experimentation, other members of the L-glutamate receptor family.

12 Claims, 17 Drawing Sheets

```
GluR-K1    . . C F I T P S - F P V D T S N Q . .
nAChR-α1   . . C E I I V T H F P F D E Q N C . .
nAChR-α2   . . C S I D V T F F P F D Q Q N C . .
nAChR-α3   . . C K I D V T Y F P F D Y Q N C . .
nAChR-α4   . . C S I D V T F F P F D Q Q N C . .
nAChR-β1   . . C S I Q V T Y F P F D W Q N C . .
nAChR-β2   . . C K I E V K H F P F D Q Q N C . .
nAChR-β3   . . C T M D V T F F P F D R Q N C . .
nAChR-β4   . . C K I E V K H F P F D Q Q N C . .
nAChR-γ    . . C P I A V T Y F P F D W Q N C . .
nAChR-δ    . . C P I S V T Y F P F D W Q N C . .
GABA-α     . . C P M H L E D F P M D A H A C . .
GABA-β     . . C M M D L R R Y P L D E Q N C . .
GlyR 48k   . . C P M D L K N F P M D V Q T C . .
```

FIG. IA

```
GluR-K1    . . Y E I W M - C I V F A Y I G V S V V L F L V S R F S P . .
nAChR-α1   . . G E K M T L S I - S V L L S L T V F L L V I V E L I P . .
nAChR-α2   . . G E K I T L C I - S V L L S L T V F L L L I T E I I P . .
nAChR-α3   . . G E K V T L C I - S V L L S L T V F L L V I T E T I P . .
nAChR-α4   . . G E K V T L C I - S V L L S L T V F L L L I T E I I P . .
nAChR-β1   . . G E K M G L S I - F A L L T L T V F L L L L A D K V P . .
nAChR-β2   . . G E K M T L C I - S V L L A L T V F L L L I S K I V P . .
nAChR-β3   . . G E K L S L S T - S V L V S L T V F L L V I E E I I P . .
nAChR-β4   . . G E K M T L C I - S V L L A L T F F L L L I S K I V P . .
nAChR-γ    . . G Q K C T V A T - N V L L A Q T V F L F L V A K K V P . .
nAChR-δ    . . G E K T S V A I - S V L L A Q S V F L L L I S K R L P . .
GABA-α     . . N R E S V P A R - T V F G V T T V L T M T T L S I S A . .
GABA-β     . . N Y D A S A A R V - A L G I T T V L T M T T I S T H L . .
GlyR 48k   . . N M D A A P A R V - G L G I T T V L T M T T Q S S G S . .
```

```
GluR1                                                              MPYIFAFFCTGFLGAVVG ANFPNNIQIGGLFPNQQSQ
GluR2                                    MQKIMHISVLLSPVLWGLIFG     VSSNSIQIGGLFPRGADQ
GluR3                                    MGQSVLRAVFFLVLGLLGHSHG    GFPNTISIGGLFMRNTVQ
GluR4                                    MRIICRQIVLLFSGFSGTRHG     AFPSSVQIGGLFIRNTDQ
GluR5 MERSTVLIQPGLWTRDTSWTLLYFLCYILP      QTSPQVLRIGGIFETVENEP
       └──────SIGNAL PEPTIDE──────┘

GluR1 QFSXGVYA   IFGFYERRTVNMLT LHVCFITPSF PVDTSNQFVLQLRP
GluR2 QFSRGVYA   IFGFYDKKSVNTIT LHVSFITPSF PTDGTHPFVIQMRP
GluR3 QFSRGVYA   IFGFYDQMSMNTLT LHTSFVTPSF PTDADVQFVIQMRP
GluR4 QYSRGVFA   ILGFYDKRSVHTLT LHISLITPSF PTEGESQFVLQLRP
GluR5 QLALGVA    LFGPSHSSSVSAVQ SICNALEVPHIQTRWKHPSVDSRDLFYIN

GluR1 QVTA       VNILTTEEGYRMLF KERLVVVDCESERLNAILGQIV     LGQIV
GluR2 QVTAINVGNI NNDKKDETYRSLF  KERRVILDCERDKVNINDIVLLEQ    DVI
GluR3 QVTARSVGNI KDVQEFRRIIEELF KERRYLIDCEVEIERLQNIL        VLL
GluR4 HVSAICVENF NDVSYRQLLEEERR KKFYVIFDCSHETAAEIL          LEQI
GluR5 KIKIRQLPPAN KDAKPLLKEMKKSKE                          LKQIL

GluR1 MQQWRTSDSRDHTRVDWKRPKYTSALTYDGVKVMAEAFQSLRRQ   QRIDISRR
GluR2 IEHWSTLEEKEYPGAHTATIKYTSALTYDAVQVMTEAFRNLRKQ   QRIEISRR
GluR3 IQRWVRLDEREFPEAKNAPLKYTSALTHDAILVIAEAFRYLRSQ   QRVDVSRR
GluR4 MDRWKKLDQREYPGSETPPKYTSALTYDGVLVMAETFRSLRRQ    QRKIDISRR
GluR5 IEKWSMERLQAPPRPETGLLDGMMTTEAALMYDAVYMVAIASH    RASQ
```

```
GluR1  T T E E G M I R V R K S K G K Y A Y L L E S T M N E Y I E Q R K P C D T M K V G G N L D S K G Y G
GluR2  T T A E G V A R V R K S K G K Y A Y L L E S T M N E Y I E Q R K P C D T M K V G G N L D S K G Y G
GluR3  T T A D G V A R V R K S K G K Y A F L L E S T M N E Y I E Q R K P C D T M K V G G N L D S K G Y G
GluR4  T T A E G V A R V R K S K G K F A F L L E S T M N E Y I E Q R K P C D T M K V G G N L D S K G Y G
GluR5  N S D E G I Q R V   L T T D Y A L L M E S T S I E Y V T Q R N C N L T Q I G G L I D S K G Y G
```

```
GluR1  S A L S N V A G V F Y I L L I G G L G L A M L V A L I E F C Y K S R S E A K R M K G F C L I P Q
GluR2  S A L S N V A G V F Y I L V G G L G L A M L V A L I E F C Y K S R A E A K R M K V A K N P Q
GluR3  S A L S N V A G V F Y I L L V G G L G L A M M V A L I E F C Y K S R A E A K R M K L T F S E A I
GluR4  S A L S N V A G V F Y I L V G G L G L A M L V A L I E F C Y K S R A E A K R M K L T F S E A I
GluR5  S V L L G V E N I G G I F E F L V A I G L V S V F V A I G E F L Y K S R K N N D V E Q C L S F N A I
                         └──── MSR IV ────┘
```

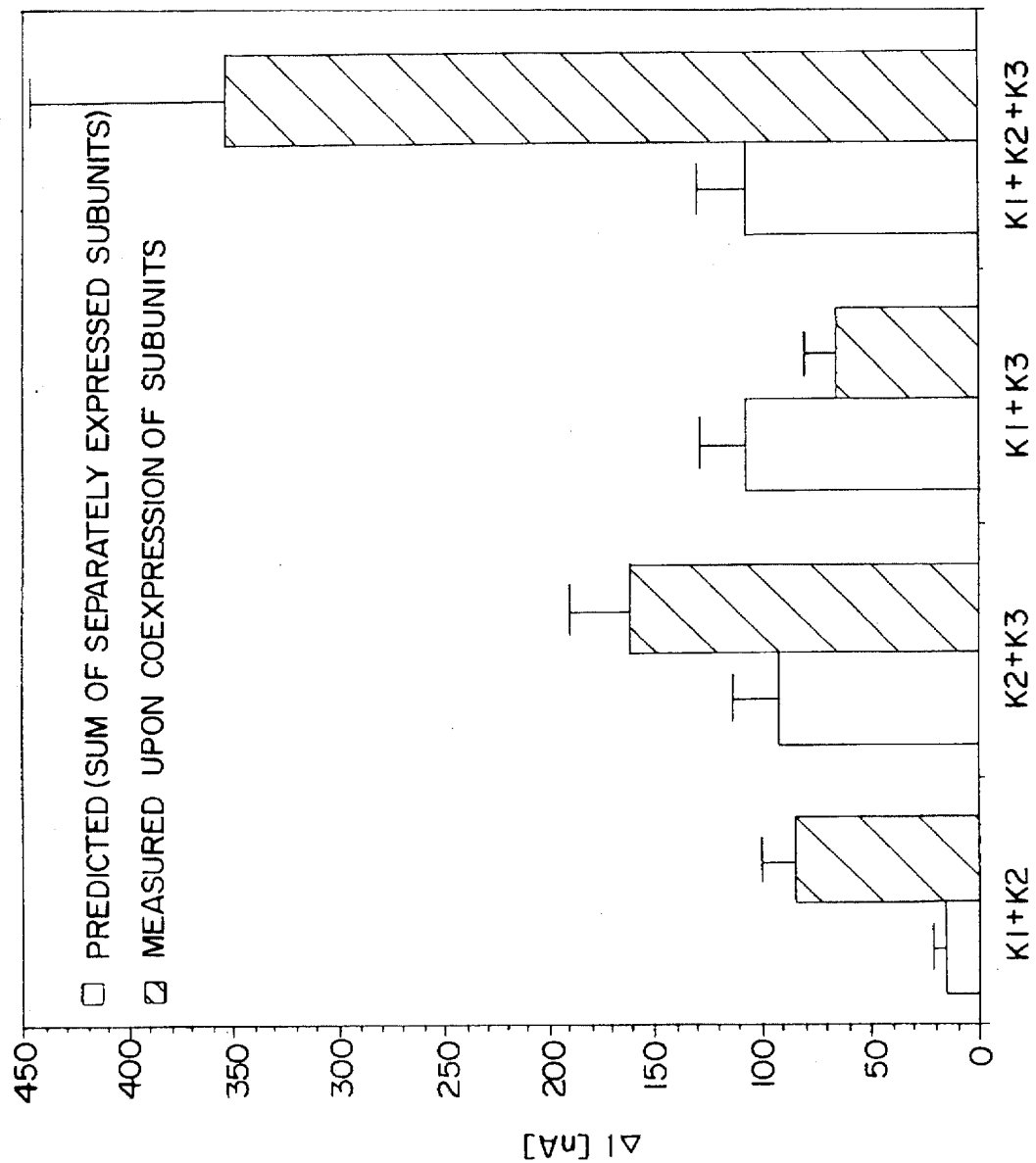

FIG. 6A

```
HVGYSYRLEIMSDGKYGARDPDTKAWNGMVGELVYGRADMAVAPLTITVREEVIDFSKPFMSLGISIMIKPQKSKPGV
ILGFLLYDVKLVPDGKYGAQNDKGEWNGMVKELIDHRADLAVAPLTITVREKVIDFSKPFMTLGISILYRKPNGTNPGV
ILGFTMEIRLVEDGKYGAQDDVNGQWNGMVRELIDHKADLAVAPLAITVREKVIDFSKPFMTLGISILYRKPNGTNPGV
ILGFSYEIRLVEDGKYGAQDDKGQWNGMVKELIDHKADLAVAPLTITVREKAIDFSKPFMTLGVSILYRKPNGTNPSV
                                                 └─── MSR I ───┘

FSFLDPLAYEITWMCIVFAYIGVSWLFLVSRFSPYEWHSEEFEEGRDQTTSDQSNEFGIFNSLWFSLGAFMQQGCDISPR
FSFLNPLSPDIWMYVLLACIGVSCVLFVIARFTPYGWYNPHPCNPDSDVVE         NNFTLLNSFWFGVGALMQQGSELMPK
FSFLNPLSPDIWMYVLLACLGVSCVLFVIARFSPYEWYNPHPCNPDSDVVE         NNFTLLNSFWFGVGALMRQGSELMPK
FSFLNPLSPDIWMYVLLAMLGVSCVLFVIARFSPYEWYDAHPCNPGSEVVE         NNFTLLNSFWFGVGSLMQQGSELMPK
                                                              └─── MSR II ───┘

SLSGRIVGGVWWFFTLIIISSYTANLAAFLTVERMVSPIESAEDLAKQTEIAYGTLEAGSTKEFFRRRSKIAVFEKMWLTYM
ALSTRIVGGIWWFFTLIIISSYTANLAAFLTVERMESPIDSADDLAKQTKIEYGAVRDGSTMTFFKKSKISTYEKMWAFM
ALSTRIVGGIWWFFTLIIISSYTANLAAFLTVERMESPIDSADDLAKQTKIEYGAVEDGATMTFFKKSKISTYDKMWAFM
ALSTRIIGGIWWFFTLIIISSYTANLAAFLTVERMESPIDSADDLAKQTKIEYGAVQDGATMTFFKKSKISTFEKMWAFM
          └─── MSR III ───┘

KSAEPSVFVRTTEEGMIRVRKSKGKYAYILESTMNEYIEQRKPCDTMKVGNLDSKGYGIATPKGSALRNPVNLAVLKIN
SSRQQSALVKNSDEGIQRV     LTTIDYALLMESTSIEYMTQRN    CNLTQIGGLIDSKGYGVGTPIGSPYRDKITIAILQLQ
SSRRQSMLVKSNEEGIQRV     LTSDYAFLMESTIIEFVTQRN     CNLTQIGGLIDSKGYGVGTPMGSPYRDKITIAILQLQ
SSKPSALVKNNEEGIQRT      LTADYALLMESTIIEYITQRN     CNLTQIGGLIDSKGYGIGTPMGSPYRDKITIAILQLQ

EQGLLDKLINKWWMDKGECGTGGGDSKDKTSALUSLSNVAGMFYILLGGLIGLAMLVALIEFCYKSRSESKRMKGFCLIPQQ
EEGKLHMKEKWRGN       GCPEEDSKEASMLGVENIGGIFIVLAAGLVLSVFVAIGEFLYKSRKNNDVEQCLSFNAIM
SSRRQSMLVKSNEEGIQRN  GCPEEESKEASALGVQNIGGIFIVLAAGLVLSVFVAVGEFLYKSKKNAQLEKRSFCSAMV
EEDKLHMKEKWWRGS      GCPEEENKEASALGIQKIGGIFIVLAAGLVLSMVVAWGEFIYKLRKTAEREQRSFCSTVA
                                                                    └─── MSR IV ───┘

SINEAIRTSTLPRNSGAGASGGGGSGENGRVVSQDFFPKSMQSIPCMSHSSGMPLGATGL
EELGISLKNQKKLKKSRTKGKSSFTSILTCHQRRTQRKETVA
EELRMSLKCQRRLKHKPQPQLL
DEIRFSLTCQRRLKHKPQPPMMVKTDAVINMHTFNDRRLPGKDSMSCSTSLAPVFP

FIG.6B
```

GLUTAMATE RECEPTOR ANTIBODIES

This application is a continuation of U.S. Ser. No. 08/013,767, filed Feb. 4, 1993, now abandoned, which is, in turn, a division of U.S. Ser. No. 07/718,575, filed Jun. 21, 1991, now U.S. Pat. No. 5,202,257, which claims priority from PCT/US90/06153, filed Oct. 25, 1990, which is, in turn, a continuation-in-part of U.S. Ser. No. 07/428,116, filed Oct. 27, 1989, now abandoned, the entire contents of each of which are hereby incorporated by reference herein.

ACKNOWLEDGEMENT

This invention was made with Government support under Grant Numbers NS 11549 and NS 28709.01, awarded by the National Institutes of Health. The Government has certain rights in this invention.

FIELD OF THE INVENTION

The present invention relates to a family of novel DNA sequences and receptor proteins encoded thereby that comprise the glutamate neurotransmitter system. The invention also relates to methods for making such glutamate receptors and for using the receptor proteins in assays designed to identify and characterize compounds which affect the function of such receptors, e.g., glutamate agonists and antagonists.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria which serve to define five receptor subtypes or classes: those activated by N-methyl-D-aspartic acid (NMDA), kainic acid (KA), α-amino-3-hydroxy-5-methyl-isoxazole-4-propionic acid (AMPA, formally called the quisqualic acid or QUIS receptor), 2-amino-4-phosphonobutyric acid (AP4 or APB), and 1-amino-cyclopentyl-1,3-dicarboxylic acid (ACPD). The effects of glutamate are mediated primarily through interactions with cation-selective, ionotropic receptors [Foster and Fagg, Brain Res. 7:103–164 (1984); Strange, Biochem. J. 249:309–318 (1988)]. An exception is the ACPD receptor subtype which has the properties of a metabotropic receptor. This class of glutamate receptors alters synaptic physiology via GTP-binding proteins and the second messengers diacylglycerol and inositol 1,4,5-triphosphate [Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987)].

The electrophysiological and pharmacological properties of the glutamate receptors have been extensively studied and are now well established. See, for example, Foster and Fagg, Brain Res. Rev. 7:103 (1984); Cotman et al., Trends Neurosci. 10:263 (1987); Mayer and Westbrook, Prog. Neurobiol. 28:197 (1987); Watkins and Olvermann, Trends Neurosci. 10:265 (1987); and Blair et al., Science 242:577 (1988). This is in contrast to their biochemical characteristics and structure at the molecular level, which, until the teaching of the present invention, remained largely unknown.

SUMMARY OF THE INVENTION

The present invention discloses a family of novel glutamate receptor proteins and DNA sequences that encode them. The glutamate receptors of the invention have electrophysiological and pharmacological properties characteristic of glutamate receptors of the central and peripheral nervous system. The glutamate receptors of the present invention are exemplified by cation-selective ion channel-type proteins encoded by cDNA clones, GluR1, GluR2, GluR3, GluR4, GluR5, GluR6 and GluR7. In addition to being useful for the production of glutamate receptor proteins, these CDNAS are also useful as probes, thus enabling those skilled in the art, without undue experimentation, to identify and isolate additional proteins in the glutamate receptor family.

The novel functional glutamate receptors of the present invention can be assembled from a plurality of either individual GluR subunit proteins (homomeric) or from combinations of subunit proteins (heteromeric). GluR1, GluR2, GluR3, GluR4, GluR5, GluR6 and GluR7 are examples of presently preferred subunit proteins for forming homomeric receptors, while the combinations of GluR1, GluR2, GluR3, GluR4, GluR5, GluR6 and GluR7 are examples of presently preferred subunit proteins for forming heteromeric receptors.

In addition to disclosing novel glutamate receptor proteins, the present invention also comprises methods for using such receptors to identify and characterize compounds which affect the function of such receptors, e.g., agonists, antagonists, and modulators of glutamate receptor function. The invention also comprises methods for determining whether unknown protein(s) are functional as glutamate receptors.

BRIEF DESCRIPTION OF THE FIGURES

FIGS. 1A–1B comprise two sequence homology analyses. FIG. 1a compares the extracellular region located between amino acid residues 89 and 106 of GluR1 with the "Cys-Cys-loop" region found in all other ligand-gated ion channels, showing sequence homology. FIG. 1b compares the putative TMD II region of GluR1 with hypothetical TMD II regions of other ligand-gated ion channels, suggesting protein sequence conservation.

Figure 2A-2:
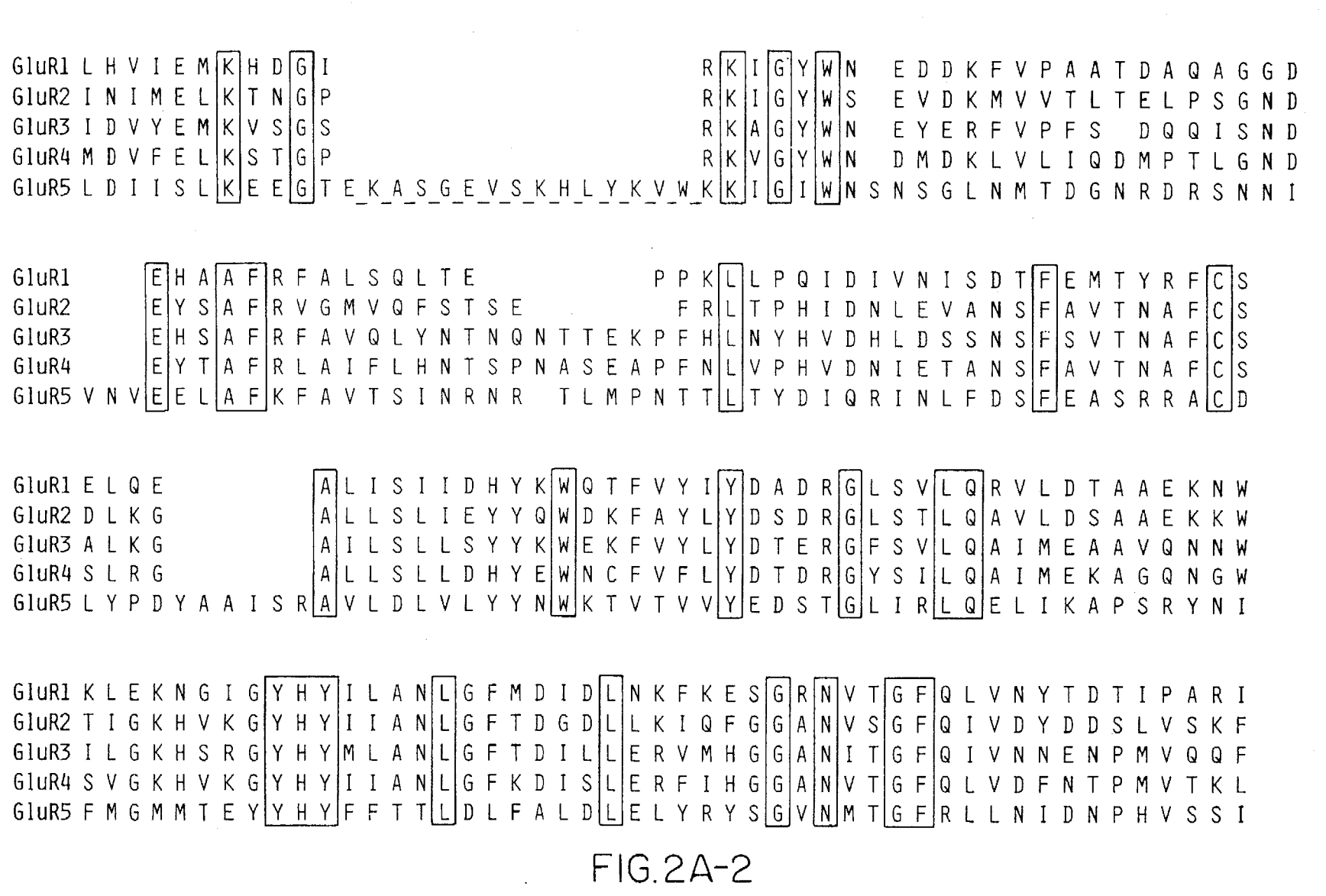
Figure 2A-3:
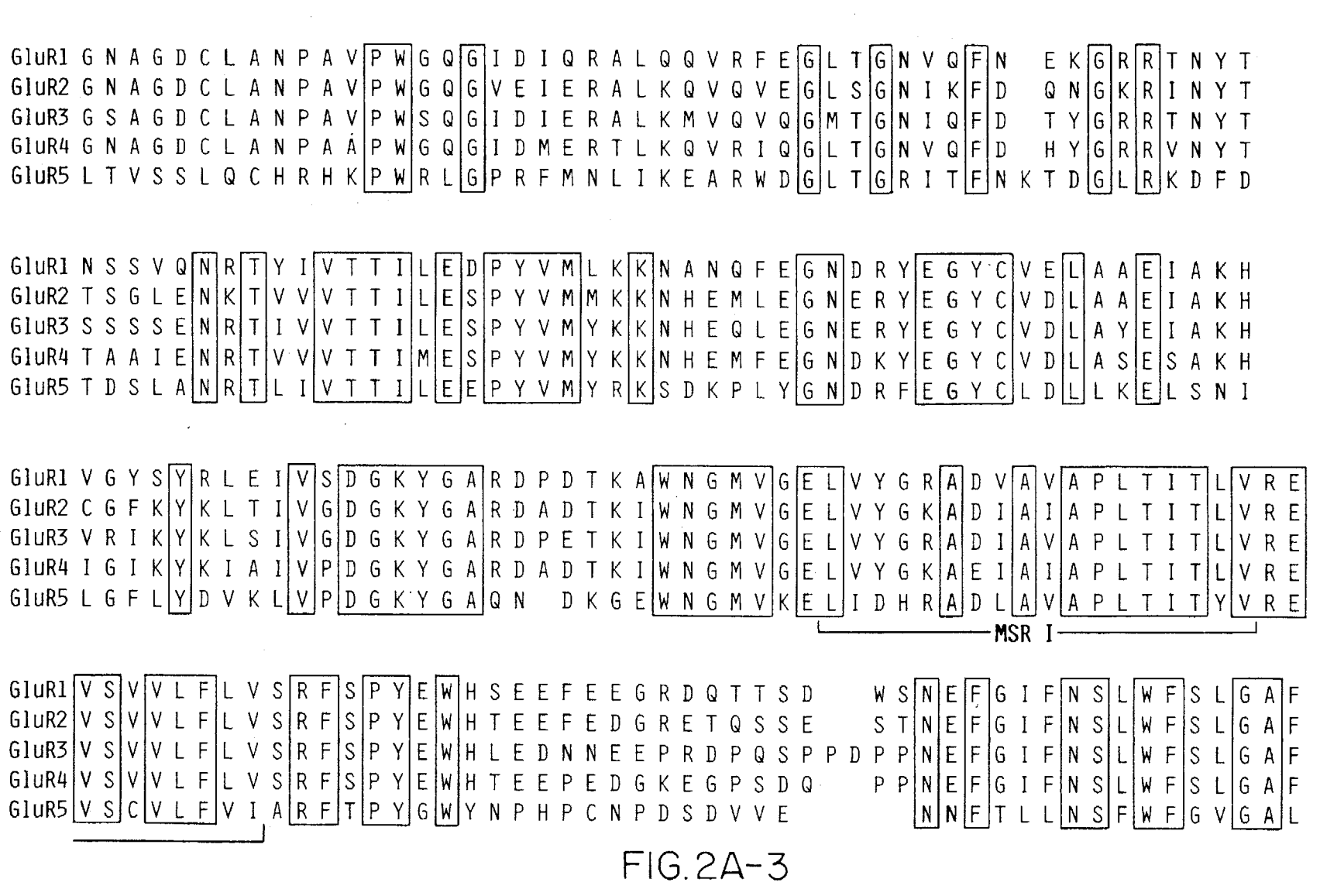
Figure 2A-4:
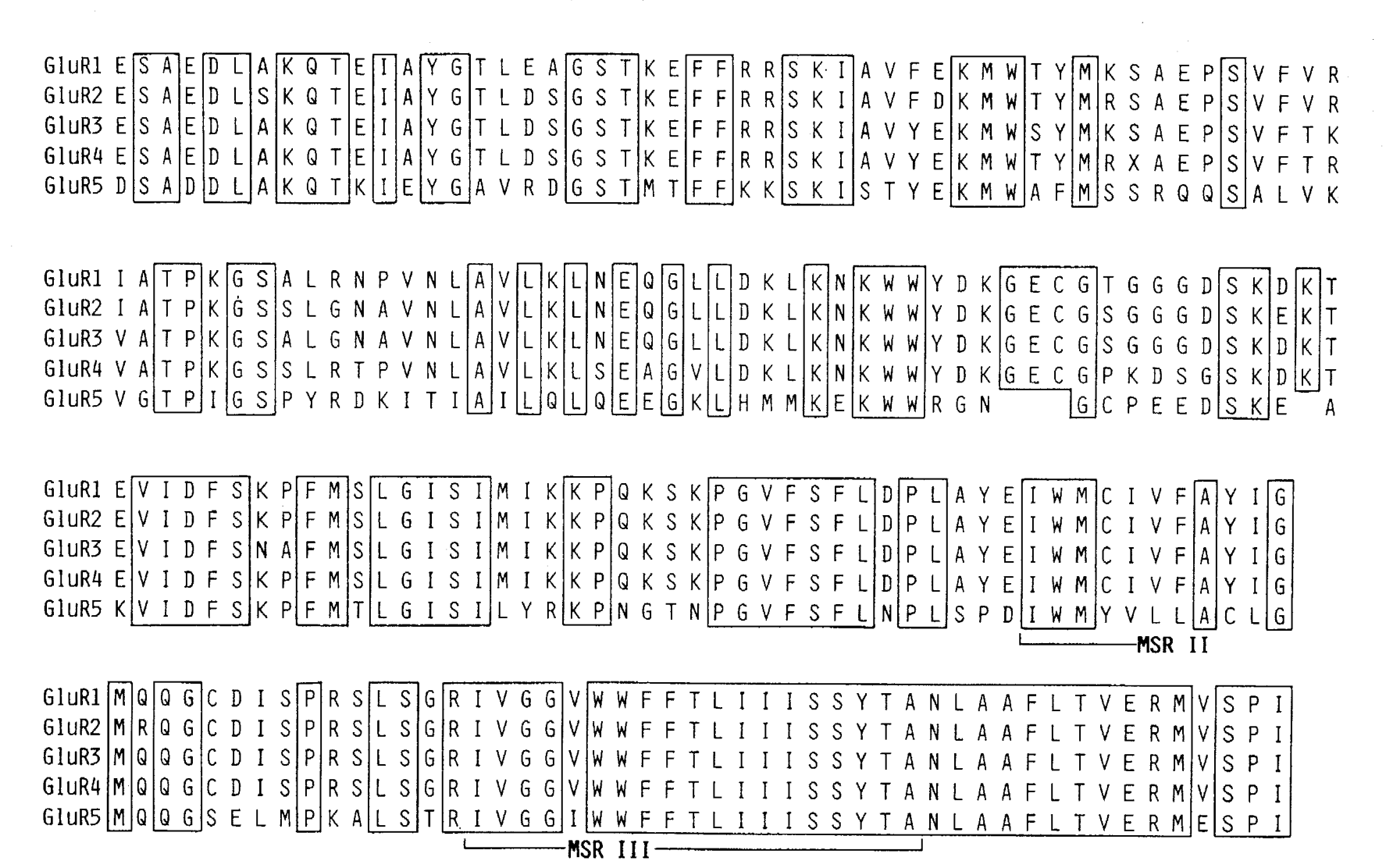

FIGS. 2A-1 to 2A-5 show the alignment of deduced amino acid sequences for the GluR1, GluR2, GluR3, GluR4 and GluR5 (GluR5-1) subunits of the glutamate receptor gene family.

FIG. 2B is a drawing which shows the alignment of deduced amino acid signal sequences for the GluR1, GluR2, GluR3, GluR4, GluR5 (GluR5-1), GluR6 and GluR7 subunits of the glutamate receptor gene family.

FIGS. 4A–4B are comprised of two graphs which compare current responses measured in Xenopus oocytes injected with combinations of GluR1, GluR2 and GluR3 RNAs.

Figure 6A:
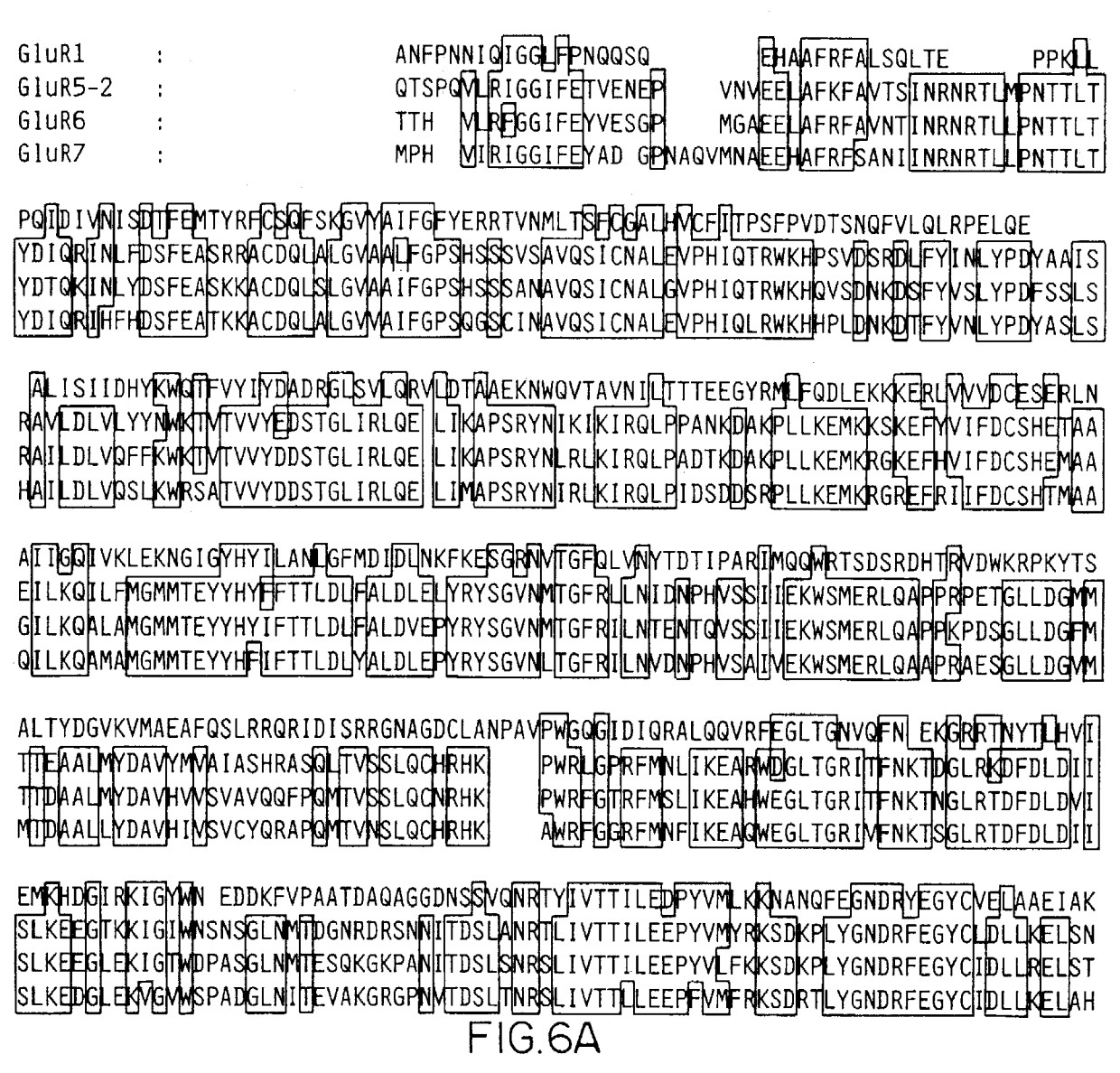

FIGS. 6A–6B present an alignment of the deduced amino acid sequences of the rat glutamate receptor subunits GluR1, GluR5 and GluR6. The GluR5 clone GluR5-1 (without a 15 amino acid insert) is used for the alignment [see Bettler et al., Neuron 5:583–595 (1990)]. Positions with amino acids identical between at least two proteins are enclosed and shaded. The predicted signal peptide and membrane spanning regions (MSR) are indicated [see Devereux et al., Nucl. Acids Res. 12:387–395 (1984)]. Numbers indicate positions in the mature subunits.

Figure 3A:
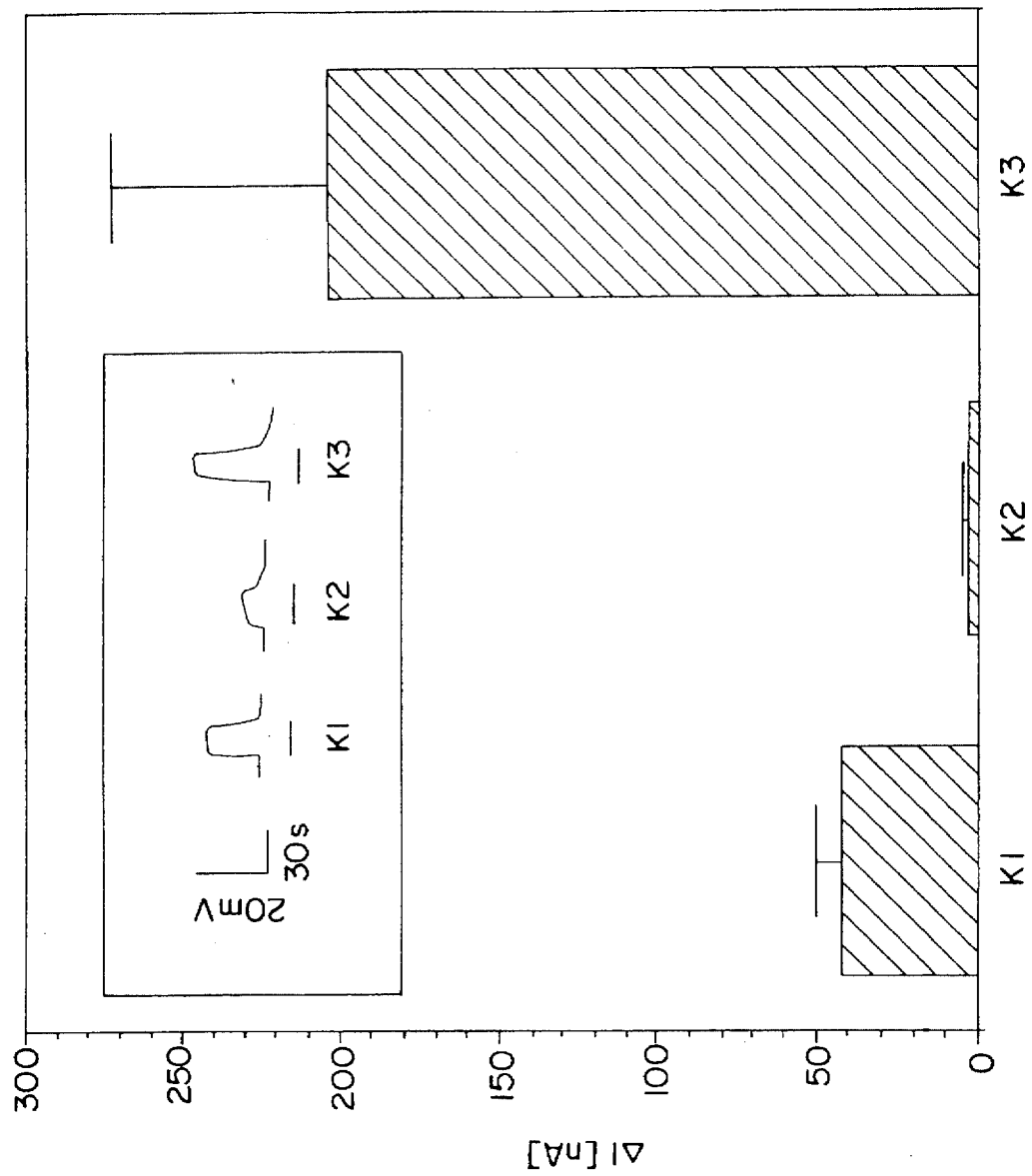
FIGS. 3A–3B are comprised of two graphs which compare current responses measured in Xenopus) oocytes injected with individual GluR1, GluR2 and GluR3 subunit RNAs (FIG. 3A) or rat brain hippocampus poly(A)$^+$ RNA (FIG. 3B).

The amino acids appearing herein may be identified according to the following three-letter or one-letter abbreviations:

| Amino Acid | 3 Letter Abbreviation | 1 Letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

The nucleotides appearing herein have the usual single-letter designations.(A, G, T, C or U) routinely used in the art.

DETAILED DESCRIPTION OF THE INVENTION

The present invention discloses a family of glutamate receptors, novel DNA sequences that encode these receptors, and various applications thereof.

As used herein, glutamate receptors refer to neurotransmitter receptor proteins that are activated by L-glutamate and related compounds. These receptor proteins are classified on the basis of their "pharmacology". Currently there are five classes of receptors, i.e., receptors activated by (1) N-methyl-D-aspartate (NMDA), which is a ligand (agonist) for the NMDA glutamate receptor subtype; (2) kainic acid (KA), which is a ligand (agonist) for the kainate glutamate receptor subtype; (3) α-amino-3-hydroxy-5-methyl-isoxazole- 4-propionic acid (AMPA), which is a ligand (agonist) for the AMPA glutamate receptor subtype, formerly called the quisqualic acid or QUIS receptor, wherein QUIS means quisqualic acid or quisqualate, which is a ligand (agonist) for the pharmacologically defined receptor subtype previously referred to as the QUIS (quisqualate) receptor; (4) 2-amino-4-phosphonobutyric acid (AP4 or APB), which is a ligand (agonist) for the APB glutamate receptor subtype; the acronym AP4 is also used to refer to this receptor subtype; and (5) 1-amino-cyclopentyl-1,3-dicarboxylic acid (ACPD), which is a ligand (agonist) for the ACPD glutamate receptor subtype.

The effects of glutamate on the first four subtypes described above are mediated primarily through interactions with cation-selective, ionotropic receptors. The ACPD receptor subtype, however, is an exception in that it has the properties of a metabotropic receptor. Metabotropic receptors alter synaptic physiology via GTP-binding proteins and second messengers (i.e., diacylglycerol and inositol 1,4,5-triphosphate).

In one aspect, the present invention comprises substantially pure proteins, or functional fragments thereof, having electrophysiological and pharmacological properties characteristic of at least one ionotropic glutamate receptor subtype selected from the N-methyl-D-aspartate (NMDA) subtype, the α-amino-3-hydroxy-5-methyl-isoxazole-4-propionic acid (AMPA) subtype, kainate (KA) subtype or the 2-amino-4-phosphonobutyrate (APB) subtype.

When used herein as a modifier of glutamate receptor protein(s) of the present invention, the phrase "having electrophysiological and pharmacological properties characteristic of a glutamate receptor" means that the neuronal signal(s) generated by receptor protein in response to glutamate or glutamate-like ligands will be comparable to those of known glutamate receptors.

The term "functional", when used herein as a modifier of glutamate receptor protein(s) of the present invention (or fragments thereof), means that binding of glutamate (or glutamate-like) ligand to receptor protein(s) causes membrane "ion channels" to open. This allows ions to move across the membrane, which in turn depolarizes the cell and generates a neuronal signal. Stated another way, "functional" means that a neuronal signal is generated as a consequence of ligand binding to receptor protein(s).

As used herein, the words "protein", "peptide" and "polypeptide" are considered to be equivalent terms and are used interchangeably.

Also contemplated by the present invention are homomeric and heteromeric (or multimeric) combinations of the above-described receptor subtypes.

As used herein, homomeric means receptors comprised of a plurality of only one type of subunit protein, e.g., homodimers, homotrimers, etc.

As used herein, heteromeric or multimeric means receptors comprised of more than one type of subunit protein.

In another aspect, the invention comprises antibodies generated against the above-described receptor proteins. Such antibodies can be used to modulate the ion channel activity of glutamate receptors, by contacting such receptors with an effective amount of such antibody.

In yet another aspect, the invention comprises substantially pure DNA encoding proteins or functional fragments thereof, as described hereinabove.

Use of the phrase "substantially pure" in the present specification and claims as a modifier of DNA, RNA, polypeptides or proteins means that the DNA, RNA, polypeptides or proteins so designated have been separated from their in vivo cellular environment. As a result of this separation and purification, the substantially pure DNAs, RNAs, polypeptides and proteins are useful in ways that the non-separated, impure DNAs, RNAs, polypeptides or proteins are not.

In still another aspect, the invention comprises cells transformed with DNAs of the invention.

In another aspect, the invention comprises substantially pure sense or antisense mRNA transcribed from the above-described DNAs, wherein the DNAs encode substantially pure functional proteins that have electrophysiological and pharmacological properties characteristic of a glutamate receptor.

In still another aspect, the invention comprises Xenopus oocytes to which mRNA of the invention has been introduced, e.g., by injection.

Still further, the invention comprises novel glutamate receptors made by expression of DNA sequences of the invention, or translation of the corresponding mRNAs. Such novel receptors include the individual GluR1, GluR2, GluR3, GluR4, GluR5, GluR6 and GluR7 receptors, fragments thereof, plus functional combinations of the receptors or fragments.

Still further, the invention comprises DNA, RNA and proteins that are functionally equivalent to the DNAs, RNAs and proteins of the present invention. Such functionally equivalent DNAs, RNAs and proteins will function in substantially the same manner as the DNAs, RNAs and proteins of the invention.

Presently preferred proteins of the invention, or functional fragments thereof, or functional combinations of these proteins and/or fragments, are proteins or functional fragments or functional combinations thereof which have electrophysiological and pharmacological properties characteristic of KA and/or AMPA glutamate receptor subtypes.

The invention proteins, or functional fragments thereof, or functional combinations of the proteins and/or the fragments, can be characterized as being encoded by DNA having at least about 40% nucleic acid homology with at least one member of the group consisting of GluR1 DNA (see, for example, Sequence ID No. 1), GluR2 DNA (see, for example, Sequence ID No. 3), GluR3 DNA (see, for example, Sequence ID No. 5), GluR4 DNA (see, for example, Sequence ID No. 7), GluR5 DNA (see, for example, Sequence ID No. 9), GluR6 DNA (see, for example Sequence ID No. 11) and GluR7 DNA (see, for example, Sequence ID No. 13), as well as substantially pure functional proteins having substantial sequence homology with the substantially pure functional proteins of the invention.

The phrase "substantial sequence homology", as used in the present specification and claims, means that the DNA, RNA or amino acid sequences which have slight and non-consequential sequence variations from the actual sequences disclosed and claimed herein are considered to be equivalent to the sequences of the present invention, and as such are within the scope of the appended claims. In this regard, "slight and non-consequential sequence variations" mean that "homologous" sequences (i.e., the sequences that have substantial sequence homology with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Alternatively, the invention proteins, or functional fragments thereof, or functional combinations of the proteins and/or the fragments can be characterized as receptors which have at least about 40% overall amino acid homology with at least one member of the group consisting of GluR1 (see, for example, Sequence ID No. 2), GluR2 (see, for example, Sequence ID No. 4), GluR3 (see, for example, Sequence ID No. 6), GluR4 (see, for example, Sequence ID No. 8), GluR5 (see, for example, Sequence ID No. 10), GluR6 (see, for example, Sequence ID No. 12) and GluR7 (see, for example, Sequence ID No. 14), as well as substantially pure functional proteins having substantial sequence homology with the substantially pure functional proteins of the invention.

Presently preferred receptor proteins of the invention, or functional fragments thereof, or functional combinations of such proteins and/or fragments are characterized as receptors having at least about 50% amino acid homology in the C-terminal domain thereof with the C-terminal domain of at least one member of the group consisting of GluR1 (see, for example, Sequence ID No. 2), GluR2 (see, for example, Sequence ID No. 4), GluR3 (see, for example, Sequence ID No. 6), GluR4 (see, for example, Sequence ID No. 8), GluR5 (see, for example, Sequence ID No. 10), GluR6 (see, for example, Sequence ID No. 12) and GluR7 (see, for example, Sequence ID No. 14), as well as substantially pure functional proteins having substantial sequence homology with the substantially pure functional proteins of the invention.

Exemplary receptors of the invention comprise substantially pure proteins selected from GluR1, GluR2, GluR3, GluR4, GluR5, GluR6 and GluR7, and combinations thereof wherein said combinations are functional as glutamate receptor(s).

As used herein, GluR1 refers to a cDNA clone which encodes a single glutamate receptor subunit protein of the same name having a $M_r$ (of the non-glycosylated receptor) of approximately 99.8 kilodaltons (kD). GluR1 was the first glutamate receptor subunit encoding CDNA to be isolated; it was previously referred to as GluR-K1. GluR-K1 has been renamed glutamate receptor subunit gene 1 or, more simply, GluR1. Additional glutamate receptor subunits or subunit related genes are called GluR2, GluR3, GluR4, GluR5, GluR6, GluR7 and so forth. GluR1 cDNA was deposited with the American Type Culture Collection on Oct. 19, 1989; and has been accorded ATCC Accession No. 68134.

As used herein GluR2 refers to a cDNA clone which encodes a single glutamate receptor subunit protein of the same name having a $M_r$ (of the non-glycosylated receptor) of approximately 96.4 kD. GluR2 cDNA was deposited with the American Type Culture Collection on Oct. 19, 1989; and has been accorded ATCC Accession No. 68132.

As used herein, GluR3 refers to a cDNA clone which encodes a single glutamate receptor subunit protein of the same name having a $M_r$ (of the non-glycosylated receptor) of approximately 98.0 kD. GluR3 cDNA was deposited with the American Type Culture Collection on Oct. 19, 1989; and has been accorded ATCC Accession No. 68133.

As used herein, GluR4 refers to a cDNA clone which encodes a single protein of the same name having a $M_r$ (of the non-glycosylated receptor) of approximately 98.5 kD. GluR4 cDNA was deposited with the American Type Culture Collection on Aug. 2, 1990; and has been accorded ATCC Accession No. 68375.

As used herein, GluR5 refers to a GluR5 cDNA clone which encodes a single protein of the same name having a $M_r$ (of the non-glycosylated receptor) of approximately 100 kD. GluR5 cDNA (as GluR5-1) was deposited with the American Type Culture Collection on Aug. 2, 1990; and has been accorded ATCC Accession No. 68374. There are two length variants of GluR5 cDNA, referred to herein as GluR5-1 and GluR5-2. Translation of the GluR5 cDNAs predicts a single long open reading frame of 920 amino acids. The difference between GluR5-1 and GluR5-2 DNA derives from an insertion of 45 nucleotides (15 amino acids) in the GluR5-1 DNA which does not interrupt this reading frame. The 15 amino acid insertion in the GluR5-1 receptor protein is unique among the receptor proteins disclosed herein; thus the shorter GluR5-2 variant is the counterpart of the GluR1, GluR2, GluR3, GluR4, GluR6 and GluR7 subunits.

As used herein, GluR6 refers to a cDNA clone which encodes a single protein of the same name having a $M_r$ (of the non-glycosylated receptor) of approximately 100 kD.

As used herein, GluR7 refers to a cDNA clone which encodes a single protein of the same name having a $M_r$ (of the non-glycosylated receptor) of approximately 100 kD.

As used herein, GluR1, GluR2, GluR3, GluR4, GluR5, GluR6 and GluR7 are each used interchangeably to refer to genes, cDNA clones and the glutamate receptor proteins they encode.

Presently preferred receptors of the invention comprise substantially pure proteins having $M_r$s (of the non-glycosylated receptor) of about 99.8 kD (GluR1), 96.4 kD (GluR2), 98.0 kD (GluR3), 98.5 kD (GluR4), 100 kD (GluR5), 100 kD (GluR6), and 100 kD (GluR7), as well as channels which possess the electrophysiological and pharmacological properties characteristic of glutamate receptors of the KA and/or AMPA subtypes.

In accordance with yet another embodiment of the present invention, there are provided antibodies generated against the above-described receptor proteins. Such antibodies can be employed for diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins as antigens for antibody production.

In accordance with still another embodiment of the present invention, there are provided methods for modulating the ion channel activity of receptor(s) of the invention by contacting said receptor(s) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

The invention DNA can be characterized as comprising substantially pure DNA having at least about 50% overall nucleic acid homology with at least one member of the group consisting of GluR1 DNA, GluR2 DNA, GluR3 DNA, GluR4 DNA, GluR5 DNA, GluR6 DNA and GluR7 DNA.

Alternatively, the invention DNA comprises substantially pure DNA encoding proteins having at least about 40% overall amino acid homology with at least one member of the group consisting of GluR1 (see, for example, Sequence ID No. 2), GluR2 (See, for example, Sequence ID No. 4), GluR3 (see, for example, Sequence ID No. 6) GluR4 (see, for example, Sequence ID No. 8), GluR5 (see, for example, Sequence ID No. 10), GluR6 (see, for example, Sequence ID No. 12), and GluR7 (see, for example, Sequence ID No. 14).

Presently preferred DNA are substantially pure DNA encoding substantially pure proteins having $M_r$s (of the non-glycosylated receptor) of about 99.8 kD (GluR1), 96.4 kD (GluR2), 98.0 kD (GluR3), 98.5 kD (GluR4), 100 kD (GluR5), 100 kD (GluR6), and 100 kD (GluR7), as well as combinations thereof that form ion channels which possess the electrophysiological and pharmacological properties characteristic of a glutamate receptor of the KA and/or AMPA subtypes.

Especially preferred DNA sequences of the invention comprise substantially pure DNA selected from GluR1 DNA (see, for example, Sequence ID No. 1), GluR2 DNA (see, for example, Sequence ID No. 3), GluR3 DNA (see, for example, Sequence ID No. 5), GluR4 DNA (see, for example, Sequence ID No. 7), GluR5 DNA (see, for example, Sequence ID No. 9), GluR6 DNA (see, for example, Sequence ID No. 11) and GluR7 DNA (see, for example, Sequence ID No. 13).

Also contemplated by the present invention are substantially pure DNA that are functionally equivalent to any of the substantially pure DNAs of the invention, wherein functionally equivalent means that the substantially pure DNA will encode proteins, or functional fragments thereof, which will form ion channel(s) in response to ligands for glutamate receptors.

Representative clones of the above-described DNA sequences have been deposited with the American Type Culture Collection. The representative cDNA clones include: GluR1 (ATCC No. 68134), GluR2 (ATCC No. 68132), GluR3 (ATCC No. 68133), GluR4 (ATCC No. 68375), and GluR5 (ATCC No. 65374).

Either the full length cDNA clones or fragments thereof can be used as probes, preferably labeled with suitable label means for ready detection. When fragments are used as probes, preferably the DNA sequences will be from the carboxyl encoding portion of the DNA, and most preferably will include ion channel encoding portions of the DNA sequence. These probes can be used, for example, for the identification and isolation of additional members of the glutamate receptor family.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into Xenopus oocytes, where translation of the mRNAs will occur. Functional analysis of the proteins thus expressed in the oocytes is accomplished by exposing the oocytes to ligands known to bind to and functionally activate glutamate receptors, and then monitoring the oocytes to see if the expressed fragments form ion channel(s). If ion channel(s) are detected, the fragments are functional as glutamate receptors.

In addition to DNA, RNA and protein compositions of matter, several novel methods are contemplated by the present invention. The first is a method for identifying DNA that is homologous to DNA known to encode glutamate receptor protein(s). This method comprises contacting an "unknown" or test sample of DNA with a glutamate receptor DNA probe (e.g., GluR1, GluR2, GluR3, GluR4, GluR5, GluR6, GluR7, etc.) under suitable hybridization conditions, and then identifying "unknown" or test DNA which hybridizes with the glutamate probe DNA as glutamate receptor homologous DNA.

Such screening is initially carried out under low-stringency conditions, which comprise a temperature of about 37° C. or less, a formamide concentration of less than about 50%, and a moderate to low salt (SSC) concentration; or, alternatively, a temperature of about 50° C. or less, and a moderate to high salt (SSPE) concentration. Presently preferred conditions for such screening comprise a temperature of about 37° C., a formamide concentration of about 20%, and a salt concentration of about 5× standard saline citrate (SSC; 20× SSC contains 3M sodium chloride, 0.3M sodium citrate, pH 7.0); or a temperature of about 50° C., and a salt concentration of about 2× SSPE (1× SSPE contains 180 mM NaCl, 9 mM $Na_2HPO_4$, 0.9 mM $NaH_2PO_4$ and 1 mM EDTA, pH 7.4). Such conditions will allow the identification of sequences which have a substantial degree of similarity with the probe sequence, without requiring perfect homology for the identification of a stable hybrid. The phrase "substantial similarity" refers to sequences which share at least 50% overall sequence identity. Preferably, hybridization conditions will be selected which allow the identification of sequences having at least 70% sequence identity with the probe, while discriminating against sequences which have a lower level of sequence identity with respect to the probe.

After low stringency hybridization has been used to identify several clones having a substantial degree of similarity with the probe sequence, this subset of clones is then subjected to high stringency hybridization, so as to identify those clones having particularly high level of homology with respect to the probe sequences. High stringency conditions comprise a temperature of about 42° C. or less, a formamide concentration of less than about 20%, and a low salt (SSC) concentration; or, alternatively, a temperature of about 65° C. or less, and a low salt (SSPE) concentration. Presently preferred conditions for such screening comprise a temperature of about 42° C., a formamide concentration of about 20%, and a salt concentration of about 2× SSC; or a temperature of about 65° C., and a salt concentration of about 0.2× SSPE.

Another method of the invention is directed to identifying functional glutamate receptors (i.e., glutamate receptors that form ion channels). This method comprises contacting glutamate receptor proteins, preferably in an oocyte expression system, with at least one ligand known to activate such receptors, measuring ion channel response to the ligand(s), and identifying as functional glutamate receptor(s) those proteins which exhibit an ion channel response as a consequence of the contact.

In accordance with a further embodiment of the present invention, there is provided a binding assay employing receptors of the invention, whereby a large number of compounds can be rapidly screened to determine which compounds, if any, are capable of binding to glutamate receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamate pathway dysfunction can be assayed to determine if the observed symptoms are perhaps caused by over- or under-production of such receptor(s).

The binding assays contemplated by the present invention can be carried out in a variety of ways, as can readily be identified by one of skill in the art. For example, competitive binding assays can be employed, as well as radioimmunoassays, ELISA, ERMA, and the like.

Yet another method of the invention involves determining whether a substance is a functional ligand for glutamate receptor protein (i.e., a modulator, an agonist or an antagonist of glutamate receptor(s)). According to this method, proteins known to function as glutamate receptors are contacted with an "unknown" or test substance (in the further presence of a known glutamate agonist, when antagonist activity is being tested), the ion channel activity of the known glutamate receptor is monitored subsequent to the contact with the "unknown" or test substance, and those substances which increase or decrease the ion channel response of the known glutamate receptor(s) are identified as functional ligands (i.e., modulators, agonists or antagonists) for receptor proteins.

As yet another application of the invention sequences, genetic screening can be carried out using the nucleotide sequences of the invention as probes. Thus, patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

Turning now to some of the specific DNAs of the invention, cDNA clone GluR1 was isolated from a rat forebrain cDNA library by screening for expression of kainate-gated ion channels in Xenopus oocytes. An insert from clone GluR1 was used as a probe to screen cDNA brain libraries (first under low-stringency hybridization conditions and then under higher stringency conditions) in order to find cDNA clones that encode other members of the glutamate receptor family. Use of the GluR1 probe cDNA led to the identification and isolation of the GluR2 and GluR3 clones. A probe from GluR2 was used to identify and isolate clones GluR4 and GluR5, and GluR5 was used to isolate clones for GluR6 and GluR7.

cDNA clone GluR1 encodes a functional glutamate receptor subunit which consists of a single protein having a $M_r$ (of the non-glycosylated receptor) of about 99.8 kD, before any post-translational modifications. This protein forms an ion channel which possesses the electrophysiological and pharmacological properties of KA and AMPA receptors.

The proteins encoded by the GluR1, GluR2, GluR3, GluR4, GluR5, GluR6 and GluR7 genes exhibit considerable inter-subunit amino acid sequence identity, as summarized in Table 1.

TABLE 1

The Percent Amino Acid Sequence Identity Among
Pairwise Combination of Members of the
Glutamate Receptor Subunit Gene Family

A. N-terminal domain

|       | GluR1 | GluR2 | GluR3 | GluR4 | GluR5 | GluR6 | GluR7 |
|-------|-------|-------|-------|-------|-------|-------|-------|
| GluR1 | 100   | 58    | 57    | 55    | 34    | 33    | 33    |
| GluR2 |       | 100   | 62    | 62    | 33    | 33    | 33    |
| GluR3 |       |       | 100   | 64    | 34    | 34    | 32    |
| GluR4 |       |       |       | 100   | 32    | 31    | 31    |
| GluR5 |       |       |       |       | 100   | 75    | 70    |
| GluR6 |       |       |       |       |       | 100   | 77    |
| GluR7 |       |       |       |       |       |       | 100   |

B. C-terminal domain

|       | GluR1 | GluR2 | GluR3 | GluR4 | GluR5 | GluR6 | GluR7 |
|-------|-------|-------|-------|-------|-------|-------|-------|
| GluR1 | 100   | 86    | 84    | 84    | 49    | 51    | 48    |
| GluR2 |       | 100   | 89    | 88    | 49    | 51    | 50    |
| GluR3 |       |       | 100   | 87    | 51    | 54    | 50    |
| GluR4 |       |       |       | 100   | 51    | 52    | 48    |
| GluR5 |       |       |       |       | 100   | 89    | 79    |
| GluR6 |       |       |       |       |       | 100   | 87    |
| GluR7 |       |       |       |       |       |       | 100   |

C. Overall amino acid sequence identity

|       | GluR1 | GluR2 | GluR3 | GluR4 | GluR5 | GluR6 | GluR7 |
|-------|-------|-------|-------|-------|-------|-------|-------|
| GluR1 | 100   | 70    | 69    | 68    | 40    | 41    | 39    |
| GluR2 |       | 100   | 73    | 72    | 40    | 41    | 40    |
| GluR3 |       |       | 100   | 73    | 41    | 42    | 40    |
| GluR4 |       |       |       | 100   | 41    | 40    | 39    |
| GluR5 |       |       |       |       | 100   | 80    | 78    |
| GluR6 |       |       |       |       |       | 100   | 79    |
| GluR7 |       |       |       |       |       |       | 100   |

The sequences were compared using sequence analysis software from the University of Wisconsin Genetics Computer Group [Devereux et al., Nucl. Acids Res. 12:387 (1984)]. The percent sequence identity between paired sequences was calculated by dividing the number of aligned positions with identical amino acids by the total number of aligned positions in the shortest of the sequences examined and multiplying the quotient by 100.

These proteins have been found to form distinct homomeric and heteromeric KA/AMPA-sensitive ion channels in Xenopus oocytes. For example, single protein subunits of glutamate receptors, GluR1, GluR2, GluR3, GluR4 and GluR5 are sufficient to form homomeric functional receptor ion-channel complexes activated by KA, AMPA, and QUIS but not by NMDA and APB. While GluR2 subunits can form functional homomeric complexes, this subunit more efficiently assembles receptor-ion channel complexes in heteromeric combination with GluR1 or GluR3 subunits. GluR6 forms homomeric ion channels which are responsive to KA, but not to AMPA.

The GluR5 protein in Xenopus oocytes forms a homomeric ion channel which is weakly responsive to glutamate but not to N-methyl-D-aspartate, kainate, quisqualate and 2-amino-4-phosphonobutyrate. The fact that oocytes expressing GluR5 are responsive to L-glutamate but not to KA, quisqualate or AMPA indicates that this protein can participate in the formation of receptors with a different pharmacological profile than the KA/AMPA subunits.

During embryonic and postnatal development the GluR5 gene is expressed in subsets of neuronal cells in the central nervous system (CNS) and the peripheral nervous system (PNS). The spatial and temporal expression pattern of the GluR5 gene is largely overlapping with the KA/AMPA subunit GluR4. However, in adult brains, the GluR5 gene is expressed in a pattern distinct from those of the KA/AMPA subunit genes, consistent with GluR5 being a subtype of glutamate receptors different from the KA/AMPA receptors.

DEPOSITS cDNA clones encoding representative glutamate receptor protein subunits of the present invention have been deposited with the American Type Culture Collection, Rockville, Md., U.S.A. (ATCC). The deposits have been made under the terms of the Budapest Treaty on the International Recognition of Deposits of Microorganisms for Purposes of Patent Procedure and the Regulations promulgated under this Treaty. Samples of the cloned DNA sequences are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

Without further elaboration, one of ordinary skill in the art can, using the preceding description, and the following Examples, utilize the present invention to its fullest extent. The material disclosed in the examples is disclosed for illustrative purposes and therefore should not be construed as being limiting in any way of the appended claims.

EXAMPLES

As used herein, bp means base pairs. Kbp means kilobase pairs, or 1000 base pairs.

As used herein, all temperatures are given in degrees Centigrade unless indicated otherwise.

Example I

Production of Brain cDNA Libraries

Poly(A)$^+$ RNA from various regions of the brain, e.g., mammalian brain, or a suitable cell line, e.g., the NCB-20 cell line, is purified by the guanidine thiocyanate-CsCl method [Chirgwin et al., Biochem 18:5294 (1979)]. The purified RNA is used as a template to prepare double strand cDNA. A poly-dT primer linked to a XhoI restriction site is used as a primer to prime the Moloney reverse transcriptase for the synthesis of the first strand using 5-methyl dCTP instead of cCTP as a precursor. RNaseH and DNA polymerase I are added to complete the second strand. The cDNA is blunt-ended with T4 DNA polymerase which increases the chance of making a full-length cDNA. EcoRI adapters are ligated to the blunt-end and the ends are kinased. The cDNA is then digested with the restriction enzyme, XhoI. This enzyme only cleaves the un-methylated XhoI restriction site attached to the dT-primer at the 3' end of the mRNA. The resulting double stranded cDNA has a XhoI restriction site at the 3' end of the mRNA and an EcoRI site at the 5' end. This cDNA is then placed into an appropriate vector, such as λZAP vector, which is part of the λZAP-cDNA cloning system from Stratagene. When the λZAP vector is used, the cDNA is placed into the vector so that the 5' end of the mRNA is near the lacZ promoter. The λZAP vector has a T3 RNA polymerase promoter at one end of the cDNA insert and a T7 RNA polymerase promoter at the other end which makes it possible to synthesize either sense or antisense RNA for further experiments, including expression in oocytes.

Example II

Low and High Stringency Hybridization cDNA libraries are preferably made with the λZAP-cDNA system described in Example I. A hybridization probe is preferably made from DNA obtained from GluR1, GluR2, GluR3, GluR4, GluR5, GluR6 or GluR7 clones or another suitable clone or source. The DNA is labeled by the random prime method, preferably using the Amersham Multiprime DNA labeling kit (Amersham Corporation, Chicago, Ill.). Preferably, low stringency hybridization conditions are used, at least at first. A suitable hybridization solution is as follows:

1M NaCl, 50 mM Tris [pH 8.0], 0.5% SDS, 0.1% sodium pyrophosphate, 100 mg/ml denatured herring sperm DNA, 0.1% [w/v] each of Ficoll, polyvinylpyrrolidone and bovine serum albumin.

For low stringency screening, a temperature of 50° C. is preferable, and library filters are washed in 2× SSPE (wherein 1× SSPE is 180 mM NaCl, 9 mM Na$_2$HPO$_4$, 0.9 mM NaH$_2$PO$_4$ and 1 mM EDTA, pH 7.4) at room temperature and exposed to Kodak XAR-5 film at −70° C.

Under these low-stringency hybridization conditions, about one in two thousand brain cDNA clones show some hybridization to the probe made from the glutamate receptor cDNA insert.

For high stringency screening, the temperature is adjusted to 65° C. and the filters are washed at this temperature in 0.2× SSPE containing 0.5% sodium dodecyl sulfate. Filters are exposed to Kodak XAR-5 film with Cronex Quanta II/III intensifying screens at −70° C. for 18–48 hours.

Example III

Analysis of Clones Identified by Hybridization

At least two different approaches can be used to analyze clones that are identified by low-stringency hybridization screening. One approach is to pick positive λZAP clones and pool them into mixtures of about 100 clones. mRNA is made in vitro from these pools of λZAP clones and the mRNA is injected into oocytes in order to test the ability of the mRNA to direct synthesis of functional glutamate receptors. If a positive clone is found, the individual λZAP cDNA clone is isolated by subdividing the pool until the functional clone is isolated. (See Example V, below, for a discussion of how this approach was used to isolate the GluR1 clone.)

A second approach that can be used to evaluate positive clones is to analyze each insert individually. Although this is tedious, the "individual clone" approach has the advantage that initially it does not require functional expression. When the "individual clone" approach is used, each clone is plaque purified and the cDNA insert is analyzed individually. This is facilitated by the fact that, at least in the λZAP cDNA system, the cDNA is cloned into a cassette flanked by the bacteriophage f1 origin of replication. The cDNA is contained within a pBluescript plasmid which can be rescued from the λZAP bacteriophage by helper infection. Once this is done, the cDNA is in the small pBluescript plasmid (which is much easier to work with than the much larger λ-bacteriophage). Sense or antisense RNA is made from the cDNA insert in the pBluescript plasmid using either the T3 (sense) or T7 (anti-sense) promoter.

cDNA inserts can also be analyzed by mapping with restriction enzymes. For example, the cDNA inserts are cut with frequent cutting restriction enzymes, and the resulting fragments size fractionated on a gel. Subsequently, the fragments are transferred to a filter for Southern blot analysis. The filters are hybridized with a probe made from DNA encoding known glutamate receptor subunits, e.g., GluR1, GluR2, GluR3, GluR5, GluR5, GluR6 or GluR7. The hybridizing fragments from each clone are subcloned into the single-stranded vector M13 (mp18 or mp19), and the fragments sequenced. DNA sequencing is performed using standard techniques, such as the dideoxynucleotide chain termination method of Sanger et al. Proc. Natl. Acad. Sci. USA 74:5463 (1977), or an automatic sequencer such as one manufactured by Applied Biosystems. The sequence is preferably analyzed by computer using software such as the programs developed by Intelligenetics, Staden and the University of Wisconsin.

mRNA made from full-length or nearly full-length clones are expressed in the oocyte system and the functional properties of the new receptors are characterized. If a clone is not functional when expressed by itself, it is tested in the presence of mRNA made from other candidate clones.

Example IV

Expression Cloning and Assay in Xenopus Oocytes

This assay is an adaptation of the assay of Masu et al., Nature 329:836 (1987). It depends upon the fact that when foreign mRNA is injected into Xenopus oocytes, the mRNA is translated into functional protein.

Either a λZAP cDNA preparation, or a plasmid containing the cDNA to be tested, are cut downstream from the cDNA insert with a restriction enzyme. The post-restriction digest is digested with Proteinase K and then extracted with two phenol: chloroform (1:1) extractions. The resulting DNA fragments are then ethanol precipitated. The precipitated fragments are mixed with either T3 RNA polymerase (to make sense strand), or T7 RNA polymerase (to make anti-sense strand), plus rATP, rCTP, rGTP, rUTP, and RNase inhibitor. Simultaneously, the RNA transcripts are capped with a sodium diguanosine triphosphate [G(5')ppp(5')G] cap. The water used for the above procedures is treated with diethylpyrocarbonate to inactivate RNases.

The in vitro synthesized mRNA transcripts are injected into Xenopus oocytes. 50 nl of an RNA solution, 0.2–0.6 mg/ml, is injected into the stage V oocytes. The injected oocytes are incubated at 16° C. in Barth's medium for 2–7 days before they are analyzed for the presence of functional receptors.

Voltage recordings are made by penetrating the oocyte with a micro-electrode filled with 3M KCl and connected to the bridge circuit of an appropriate voltage clamp unit, e.g., the Dagan 8500 voltage clamp unit. Voltage recordings are preferably obtained with two electrodes, a voltage electrode filled with 3M KCl and a current electrode filled with 0.25M CsCl, 0.25M CsF and 50 mM EGTA (ethylene glycol tetraacetic acid). Example VI provides a discussion of results of recordings from oocytes injected with RNA from GluR1 cDNA encoding a KA/AMPA glutamate receptor.

Oocytes employed herein are obtained from ovarian tissue from anesthetized adult female Xenopus. The ovarian tissue is treated with collagenase, 2 mg/ml, for two hours and then the ovarian epithelium and follicular cells are dissected away.

Example V

Expression Cloning of the GluR1 Receptor

Xenopus oocytes were injected with poly(A)$^+$ RNA isolated from rat forebrain. 2–10 days later, the oocytes were tested electrophysiologically for their ability to respond to selective agonists for glutamate receptor subtypes. Both glutamate and quisqualate induce membrane depolarizations. These responses display a biphasic pattern composed of a fast acting, smooth (presumably ligand-gated ion channel) response, and a longer lasting, fluctuating, (probably second-messenger mediated) response. NMDA and KA elicited smooth responses with fast onsets, while APB gave no response.

A directional cDNA library (λZAPII RTB1; complexity: 8×10$^5$ elements), consisting of 18 independent sublibraries of 44,000 clones each, was constructed from this poly(A)$^+$ RNA using the bacteriophage expression vector λZAPII. A pool of in vitro transcripts, comprised of transcripts made separately from all 18 amplified sublibraries, was injected into oocytes. Small depolarizations (1–3 mV) were seen in voltage recordings from oocytes challenged with 100 µM kainate 10 days after injection. No responses to NMDA or quisqualate were detected. Neither uninjected oocytes nor water-injected oocytes showed any responses to glutamate receptor agonists. Subsequently, pools of 44,000 clones (=the single sublibraries), 4,000, 400 and 40 clones were tested. In each of these tests at least one pool responded to KA.

The following criteria were used throughout the screening procedure to assure that the very small responses observed initially were not recording artifacts: (a) responses in a given oocyte were reproducible, (b) responses were fast (within one second of agonist application), (c) responses were readily reversible upon superfusion of the oocyte with control Ringer solution, (d) 10 µM domoate gave a response similar to the one elicited by 100 µM kainate.

The pools yielding the largest responses at each stage were selected for further subdivision. The clones in the final positive pool of 40 clones were analyzed for their insert size, and the 12 clones with the largest inserts (all>2 kb) were tested individually for their ability to direct the synthesis of a functional kainate receptor. Only one clone, carrying a 3.0 kb insert, was found to elicit kainate responses and was named λZAPII-GluR1.

Example VI

Electrophysiological and Pharmacological Characterization of the GluR1 Clone

The plasmid pGluR1 was subsequently rescued from bacteriophage λZAPII-GluR1. Upon transcription and translation in vitro, the translation product of sense RNA (but not antisense RNA) induced kainate responses when injected into oocytes. The GluR1 translation product from as little as 10 pg of GluR1 sense transcript gave detectable responses to 100 µM KA under voltage-clamp conditions (−70 mV holding potential).

In order to rule out the possibility that GluR1 codes for a transcription factor, oocytes injected with pGluR1 in vitro transcripts were kept in medium supplemented with 50 µg/ml actinomycin D to inhibit endogenous transcription. These oocytes exhibited the same responses to kainate as those kept in control medium. Therefore, injection-induced transcription from the oocyte genome does not contribute to the observed responses.

L-glutamate evoked much smaller responses than did KA, and even at 1 mM elicited only 50% of the depolarization seen with 30 µM KA. This is consistent with the observation that glutamate is only a weak agonist for the KA receptor subtype [Monaghan et al., Nature 306:176 (1983)]. Other glutamate receptor agonists such as NMDA, quisqualate and L-aspartate evoked no responses when applied at 150 µM, 10 µM, and 100 µM, respectively. Unrelated neurotransmitter receptor agonists such as glycine, γ-aminobutyric acid (GABA$_A$), serotonin and nicotine also failed to evoke responses, even when tested at concentrations as high as 1 mM. Glycine did not potentiate the KA response. Dose-response curves for KA and domoate were recorded and $EC_{50}$ values of 39 µM and 1.8 µM, respectively, were derived. The average reversal potential was 10 mV, as extrapolated from current responses to 10 µM kainate obtained at a series of holding potentials between 0 and −130 mV. Responses to KA did not desensitize, even after prolonged (up to 10 minutes) superfusion with high concentrations (100 µM) of agonist.

Similarly, the pharmacological profile of GluR1, as revealed by the inhibiting properties of various known glutamate receptor antagonists (see Table 2), is consistent with previous reports for KA receptors in systems where total poly(A)$^+$ RNA was used as a source of kainate receptor message [Hirono et al., Neurosci. Res. 6:106 (1988); Lerma et al., Proc. Natl. Acad. Sci. USA 86:2083 (1989)].

As used herein, the term antagonist refers to a substance that interferes with receptor function. Antagonists are of two types: competitive and non-competitive. A competitive antagonist (also known as a competitive blocker) competes with an agonist for overlapping binding sites. A noncompetitive antagonist or blocker inactivates the functioning of the receptor by binding to a site on the receptor other than the agonist binding site.

TABLE 2

Pharmacology of the Glutamate Receptor Encoded by GluR1: Properties of various Glutamate Receptor Antagonists as Measured in Oocytes Injected With GluR1 in vitro RNA[a]

| Compound Tested[b] | Compound Alone (%)[c] | Compound Plus Kainate (%)[d] |
|---|---|---|
| kainate (agonist control) | 100.0 | 100.0 |
| Kynurenic acid | 3.4 ± 0.2 | 9.6 ± 1.3 |
| γ-DGG | −0.1 ± 0.5 | 30.8 ± 1.1 |
| GAMS | 1.0 ± 0.6 | 30.7 ± 1.1 |
| GDEE | 24.8 ± 5.7 | 97.8 ± 6.6 |
| PDA | 2.5 ± 0.7 | 31.3 ± 2.0 |
| APV | 3.1 ± 1.4 | 73.7 ± 3.2 |
| CPP | 9.1 ± 0.7 | 78.8 ± 0.9 |

[a]Oocytes had been injected with 1.25 ng of GluR1 in vitro sense RNA 3 days prior to the recording. The oocytes were voltage-clamped at −70 mV, and the test compounds (all at 1 mM, except kainate, which was 30 μM) applied by rapid superfusion, with 5 minute intervals between drugs. Peak currents were recorded; each number represents the average of 3 recordings from 3 different oocytes, ± SEM. The 100% current response corresponds to 40-200 nA, depending on the oocyte.
[b] = Abbreviations for the compounds used refer to:
γ-DGG means γ-D-glutamylglycine;
GAMS means γ-D-glutamylamino-methyl-sulphonate;
GDEE means glutamate diethyl-ester;
PDA means 2,3-cis-piperidine dicarboxylic acid;
APV means 2-amino-5-phospho-novaleric acid;
CPP means 3-(2-carboxypiperazin-4-yl)propyl-1-phosphate.
[c] = % of the response evoked by 30 μM kainate immediately before drug application.
[d] = % of the response seen with 30 μM kainate alone immediately before application of drug/kainate mixture Of all the compounds tested (each at 1 mM), the broad specificity glutamate receptor antagonist kynurenic acid clearly was the most potent inhibitor of the kainate-evoked depolarizations in oocytes injected with GluR1 RNA synthesized in vitro. To a lesser extent, γ-DGG, reported to preferentially block KA and NMDA receptors but not quisqualate receptors [Davies and Watkins, Brain Res. 206:173 (1981)], inhibited kainate responses, as did GAMS, which reportedly prefers KA and AMPA receptors [Fagg, Trends Neurosci. 8:207 (1985)]. Similarly, PDA, which is known to block all subtypes of glutamate receptors [Foster and Fagg, Brain Res. Rev. 7:103 (1984)], blocked the GluR1 response. GDEE, which is thought to preferentially inhibit AMPA-type glutamate receptors [Foster and Fagg, supra], did not block the response significantly, but instead displayed weak agonist properties. The NMDA receptor antagonists APV and CPP, as well as NMDA itself, slightly inhibited the KA responses, thus acting as weak antagonists. They did not show any agonist properties.

Taken together, the electrophysiological properties observed in oocytes injected with GluR1 transcript, as well as the observed pharmacological properties, indicate that GluR1 represents a functional KA receptor indistinguishable from the one observed in oocytes injected with total poly (A)⁺ RNA. Thus, the single protein subunit encoded by GluR1 is sufficient to form an active receptor-ion channel complex.

Example VII

Sequencing and Primary Structure of GluR1

The cDNA insert of the plasmid pGluR1 was subcloned into M13mp19 and sequenced (see Sequence ID No. 1). An open reading frame of 2721 bp was found within the total length of 2992 bp. The predicted protein consists of 889 amino acids, with a calculated $M_r$ (of the non-glycosylated form of the receptor subunit) of about 99.8 kD. The deduced protein sequence contains a putative signal peptide of 18 amino acids at its N-terminus, with a predicted cleavage site that conforms to empirical rules [von Heijne, Nucl. Acids Res. 14:4683 (1986)]. The N-terminus of the protein therefore is expected to be located extracellularly. Nucleotides 198 to 251 encode the putative signal peptide, and bases 1 through 197 represent a 5'-untranslated region. At the 3'-terminus of the clone, 71 nucleotides of untranslated sequence were found.

The deduced amino acid sequence for GluR1 is shown in Sequence ID No. 1, along with the nucleotide sequence. The numbering for the amino acid sequence starts with the first residue of the precursor protein, with the first residue of the mature protein being residue 19 (following cleavage of the putative signal sequence). Possible extracellular N-glycosylation sites are present at amino acid residues 63, 249, 257, 363, 401, and 406. The region between amino acids 107–131 bears some resemblance to the ligand-gated ion channel signature postulated by some workers [Grenningloh et al., Nature 330:25 (1987); Barnard et al., TINS 10:502 (1987)]. Sequence comparisons with other sequenced ligand-gated ion channels, the nicotinic acetylcholine receptors, $GABA_A$ receptors and glycine receptors, reveals little overall homology.

The insert cDNA of the bacteriophage clone λZAPII-GluR-K1 was cut out with EcoRI/XhoI, blunt-ended and subcloned into the SmaI-site of the bacteriophage vector M13mp19 [Messing et al., Proc. Natl. Acad. Sci. USA 74:3642 (1977)], yielding clones with both orientations of the cDNA. Overlapping deleted subclones were constructed for each strand orientation using the Cyclone™ kit from United States Biochemical Corporation (Cleveland, Ohio). Single-stranded sequencing by the dideoxynucleotide chain-termination method [Sanger et al., Proc. Natl. Acad. Sci. USA 74:5463 (1977)], was carried out with all 45 subclones, and additionally, 10 oligonucleotide primers were synthesized to facilitate sequencing across areas where compressions or gaps were encountered in the sequences derived from the deletion subclones. Complete sequences for both strands were thus obtained. IntelliGenetics software packages (IntelliGenetics version 5.0, and PC/Gene™ (IntelliGenetics, Inc., Mountain View, Calif.) were used for analyzing sequences.

All ligand-gated ion channel subunits sequenced prior to the present invention have a conserved extracellular region characterized by 2 cysteine residues spaced 14 amino acids apart from each other, with conserved proline and aspartate residues located 8 and 10 amino acids, respectively, downstream from the first of these two cysteines [Barnard et al., Trends Neurosci. 10:502 (1987)]. This hypothetical signature for neurotransmitter receptor-channel complexes is poorly conserved in the protein encoded by GluR1. The proline and aspartate residues are present, but the first cysteine residue is located only 7 residues upstream from the proline residue, and the second cysteine residue is absent.

A hydropathy plot analysis of GluR1 revealed several regions which are candidates for transmembrane domains (TMDs). The region between amino acids 481 and 827 was notable because its hydropathy profile resembled that seen in the other ligand-gated ion channels: three closely spaced putative TMDs which are separated by ~175 amino acid residues from a fourth putative TMD which is located close to the C-terminus of the protein. Within this region, the following four transmembrane regions are assigned in GluR1: TMD I, located between amino acid residues 481 and 498, TMD II between residues 538 and 556, TMD III between residues 613 and 631, and TMD IV between residues 805 and 825.

FIG. 1A presents a comparison of the extracellular region located between amino acid residues 107 and 124 of GluR1 with the "cys-cys-loop" region found in all other ligand-gated ion channels, showing sequence homology. Sequences of neuronal nicotinic acetylcholine receptor (nAChR) subunits α1, β1, γ, δ are from mouse muscle [Heinemann et al., Molecular Neurobiology: Recombinant DNA Approaches (ed. Heinemann, S. & Patrick, J.) 45–96 (Plenum Press, New York, 1987)], those of nAChR subunits α2, α3, α4, β2, β3, and β4 are from rat brain [Deneris et al., J. Biol. Chem. 264:6268 (1989); Duvoisin et al., Neuron 3:487 (1989)]. $GABA_A$ subunits α and β are from calf brain [Barnard et al., Trends Neurosci 10:502 (1987)]. GlyR 48 k is the $M_r$=48 kDa subunit of the glycine receptor from rat brain [Grenningloh et al., Nature 328:215–220 (1987)]. Boxed amino acid residues are found at identical positions in GluR1 as well as in at least one of the other receptor sequences. One gap has been introduced arbitrarily.

FIG. 1B presents a comparison of the putative TMD II region of GluR1 with hypothetical TMD II regions of other ligand-gated ion channels [Barnard et al., Trends Neurosci. 10:502 (1987); Deneris et al., J. Biol. Chem. 264:6268 (1989); Duvoisin et al., Neuron 3:487 (1989); Grenningloh et al., Nature 328:215 (1987); Heinemann et al., in: Molecular Neurobiology; Recombinant DNA Approaches (ed. Heinemann, S. & Patrick J.) 45–96 (Plenum Press, New York, (1987)]; suggesting protein sequence conservation.

Example VIII

Isolation and Characterization of GluR2 and GluR3 cDNA clones encoding the GluR2 and GluR3 genes were isolated from an adult rat forebrain library using a low-stringency hybridization screening protocol (see Example II) and a radiolabeled fragment of the GluR1 cDNA as probe. Sequence ID Nos. 3 and 5 show the nucleotide and derived amino acid sequences of clones λRB14 (GluR2) and λRB312 (GluR3), respectively. The calculated molecular weights for the mature, non-glycosylated forms of GluR2 and GluR3 are 96,400 daltons (862 amino acids) and 98,000 daltons (866 amino acids), respectively. Potential N-linked glycosylation sites occur in the GluR2 protein at Asn-239, Asn-359, Asn-381, Asn-406, and Asn-851 and in the GluR3 protein at Asn-37, Asn-243, Asn-363, Asn-374, and Asn-394. Like GluR1, the hydrophobicity profile for both GluR2 and GluR3 reveals five strongly hydrophobic regions: one such domain is located at the amino terminus of each protein and has characteristics of a signal peptide, while four additional hydrophobic regions presumably form membrane-spanning regions (MSR I–IV) and are located in the carboxy-terminal domain of each polypeptide.

FIGS. 2A-1 to 2A-5 is an alignment of the deduced amino acid sequences for the proteins encoded by the GluR1, GluR2, GluR3, GluR4 and GluR5 genes. In the figure, identical residues in all compared sequences are boxed, with spaces introduced as appropriate to maximize homology. Predicted signal peptides and four proposed membrane spanning regions (MSR I–IV) are indicated. The hatched line denotes the insertion of 15 amino acid residues found in the GluR5-1, but not in the GluR5-2 protein. As the aligned sequences demonstrate, there is significant sequence identity between GluR1 and both GluR2 (70%) and GluR3 (69%) as well as between GluR2 and GluR3 (74%; see also Table 1). The sequence identity is most pronounced in the carboxy-terminal half of each protein.

FIG. 2B is a comparison of the deduced amino acid sequences for the signal peptides encoded by the GluR1, GluR2, GluR3, GluR4, GluR5, GluR6 and GluR7 genes.

Example IX

Electrophysiological Comparison: GluR1, GluR2 and GluR3

Based on the strong sequence similarity between the proteins encoded by GluR1, GluR2 and GluR3, the following experiments were conducted to determine if the GluR2 and GluR3 proteins might function as homomeric, kainate-sensitive ion channels in Xenopus oocytes (as is the case with GluR1). Thus, oocytes were injected with in vitro synthesized RNA transcripts derived from individual cDNA clones. FIGS. 3(A and B) presents a comparison of current responses measured in Xenopus oocytes injected with individual GluR1, GluR2 and GluR3 subunit RNAs or rat brain hippocampus poly(A)$^+$ RNA. FIG. 3A shows responses of oocytes to 100 mM KA measured 3 days after injection of individual GluR1 (2 ng), GluR2 (10 ng) or GluR3 (2 ng) RNA. The insert shows examples of voltage recording traces obtained from such oocytes except that the GluR2 response was obtained 5 days after injection of 25 ng RNA. The figure further shows that both GluR2 and GluR3 injected oocytes depolarize in response to batch application of 100 μM KA.

The amplitudes of the KA responses were not equivalent for the three glutamate receptor subunits: with equal amounts of injected RNA (2 ng), responses in GluR3 RNA-injected oocytes were invariably larger than GluR1 responses. KA-invoked depolarizations in GluR2-injected oocytes were the weakest and could only be detected in oocytes injected with much larger amounts of RNA (10 to 25 ng).

Figure 3B:
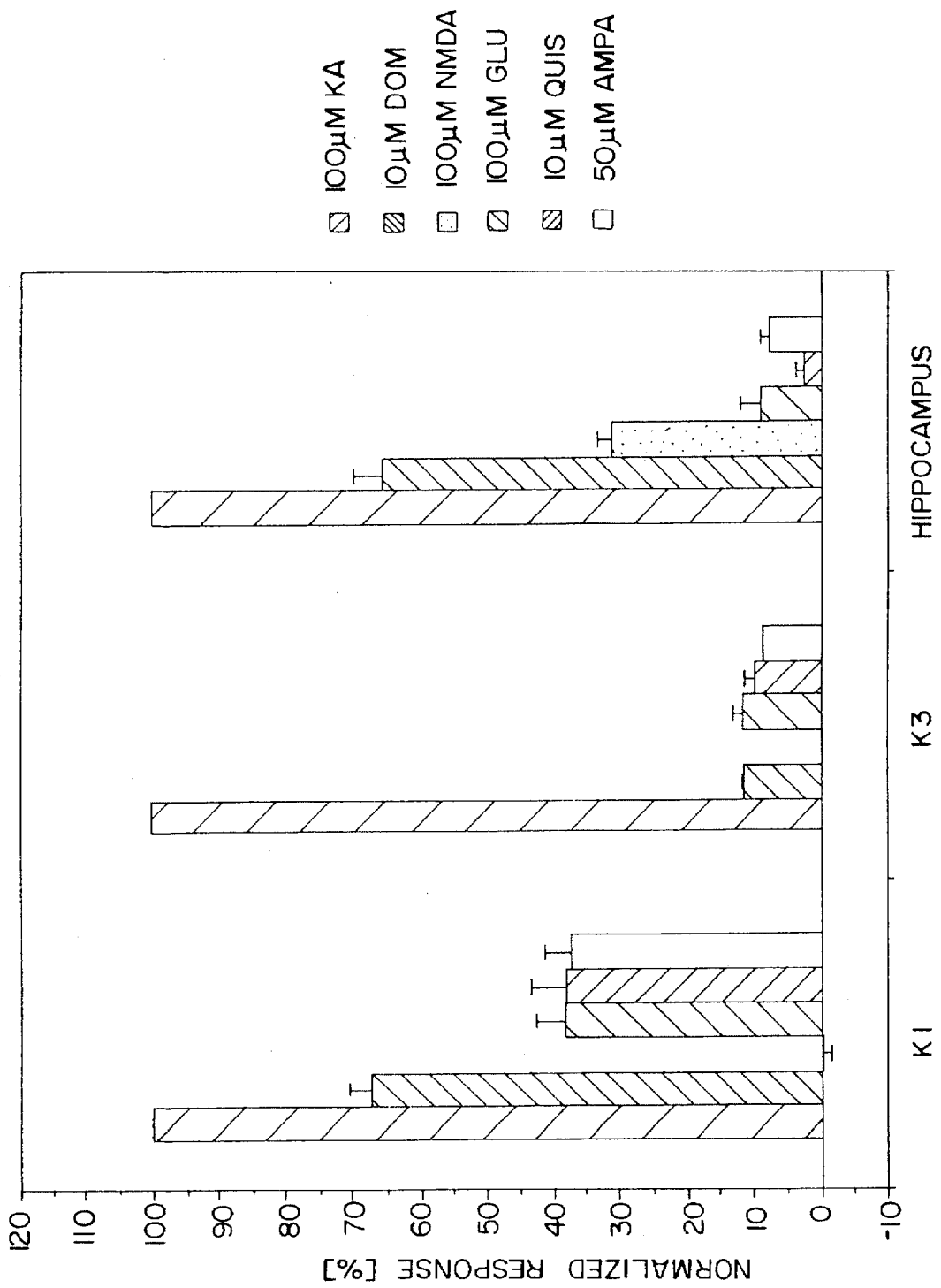

The data in FIG. 3B represent the responses of oocytes to the indicated agonists measured 3 days after injection with GluR1 (2 ng) or GluR3 (2 ng) RNA or adult rat brain hippocampus poly(A)$^+$ RNA (~50 ng). All values are normalized to the response obtained with 100 mM KA and are presented as the mean ± S.E.M. with n≧3 for all measurements. All oocytes were voltage-clamped to −70 mV and recordings were performed as described by Hollmann et al., Nature 342:643 (1989). The data show that, in addition to KA, oocytes injected with GluR1 or GluR3 RNA also respond to QUIS (10 μM), AMPA (50 μM), and glutamate (GLU, 100 μM). No detectable responses were obtained with NMDA (30 μM plus 10 μM glycine) or APB (50 μM). Responses obtained from oocytes injected with GluR2 RNA were too small for reproducible quantitation and were, therefore, excluded from the analysis. For GluR1-injected oocytes, the responses to AMPA and QUIS were typically 35–40% of the maximal KA response, while for GluR3-injected oocytes they were about 10% of the KA response. Relative to KA, the response of GluR1 to domoic acid (DOM, 10 μM) is about 6-fold greater than that seen for GluR3. Taken together these data demonstrate that receptors assembled from GluR1 or GluR3 subunits are pharmacologically distinct. Furthermore, the observation that homomeric GluR1 and GluR3 receptors respond to both QUIS and AMPA, albeit with reduced efficiencies, provides direct evidence that KA, QUIS and AMPA can bind to the same glutamate receptor polypeptide.

FIG. 3B also shows that the pharmacological profile of oocytes injected with individual GluR1 or GluR3 subunit RNA is significantly different than that seen in oocytes injected with rat brain hippocampus poly(A)+ RNA. This suggests that the response seen in oocytes injected with hippocampus RNA is mediated by heteromeric glutamate receptors assembled from various combinations of GluR1, GluR2 and GluR3 subunit polypeptides. This suggestion is supported by the fact that all three GluR subunit genes are actively transcribed in the hippocampus.

Example X

Pharmacological Comparison of GluR1, GluR2 and GluR3

Figure 4B:
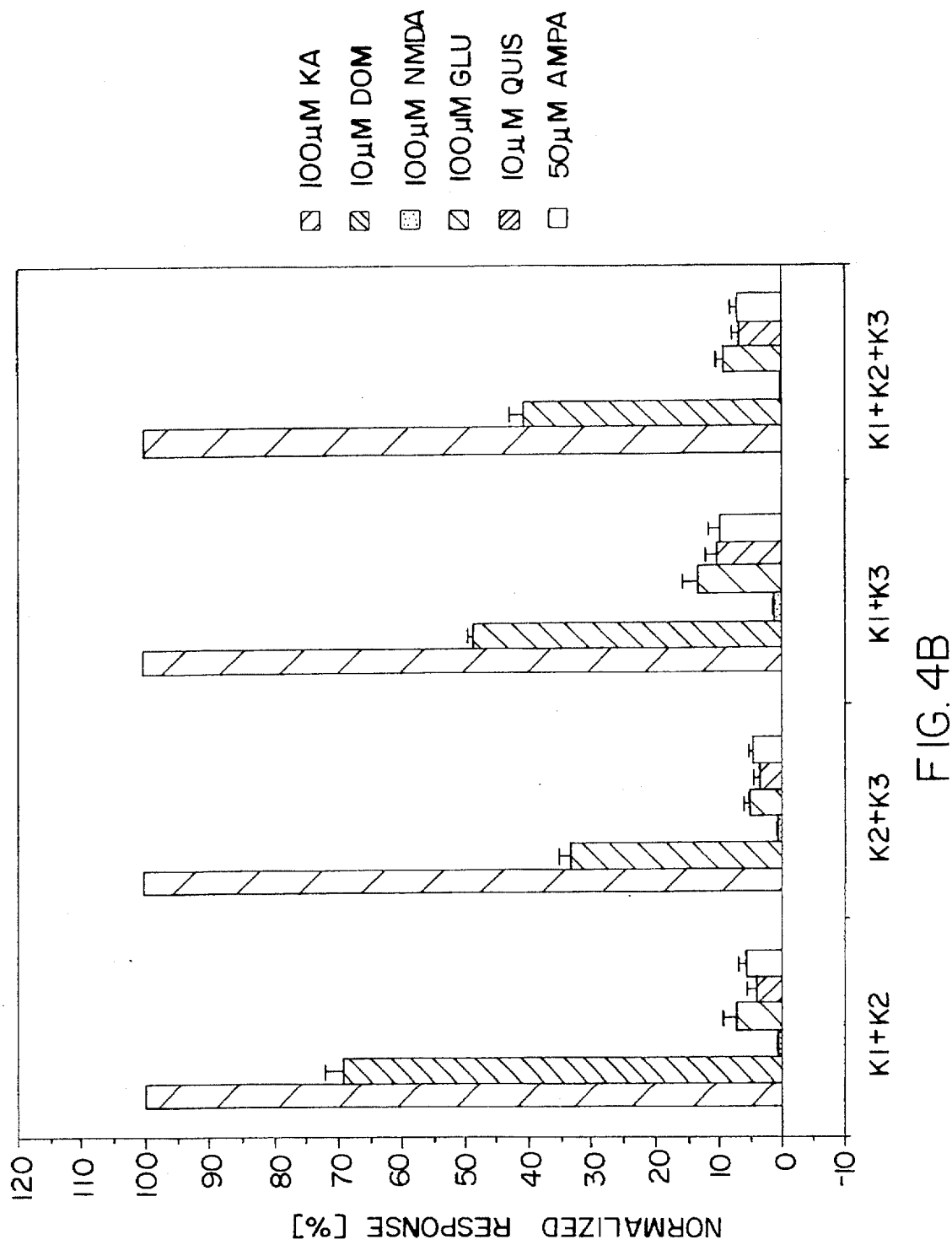

This example addresses the question of whether glutamate receptors assembled from mixtures of proteins encoded by the GluR1, GluR2 and GluR3 subunit genes have pharmacological properties significantly different from each other or from those observed for single subunit receptors. FIGS. 4A–4B present a comparison of current responses measured in Xenopus oocytes injected with combinations of GluR1, GluR2 and GluR3 RNAs.

A comparison of the data in FIGS. 3B and 4B suggests that, for the agonists tested, there are few substantial differences in the pharmacology. FIG. 4B summarizes the responses of oocytes to the indicated agonists measured 3 days after injection of 2 ng RNA for each of the indicated GluR subunits or 50 ng rat brain hippocampus poly(A)+ RNA. Values have been normalized to the response obtained with 100 mM KA and are presented as the mean ± S.E.M. with n≥3 for all measurements. All oocytes were clamped to −70 mV and recordings performed as described by Hollmann et al. [Nature 341:643 (1989)]. Responses to QUIS, AMPA and GLU are, relative to GluR1, significantly reduced in the oocytes expressing the subunit combinations. Except for the NMDA response, the overall agonist profiles for oocytes injected with GluR subunit combinations are more similar to oocytes containing hippocampus poly(A)+ RNA than to those injected with either GluR1 or GluR3 subunit RNA alone.

Example XI

Comparison of KA-Activated Currents Recorded from GluR1, GluR2 and GluR3

FIG. 4A presents the responses of oocytes to 100 mM KA measured 3 days after injection of 2 ng RNA for each of the indicated GluR subunit combinations. The open columns represent the sum of the responses measured in oocytes expressing the individual GluR subunit RNAs, while the stippled columns show the measured amplitudes after expression of combinations of the GluR subunit RNAs in individual oocytes. The figure compares KA-activated currents recorded from oocytes injected with mixtures of GluR1, GluR2 and GluR3 subunit (stippled columns) with the summed currents measured for the individual subunits (blank columns).

The principle finding is a significant potentiation of KA-evoked currents in oocytes coexpressing glutamate receptor subunits. For example, co-expression of GluR1 plus GluR2 yields an approximately 4-fold increase over the summed responses for singly-injected oocytes; or co-expression of GluR2 plus GluR3 subunits yields an approximately 2-fold increase. Injection of all three subunit RNAs results in an average 2.5 fold-increase in KA-evoked currents.

These results indicate that, in oocytes, individual glutamate receptor subunit polypeptides do not behave in a simple independent fashion. Instead, the various subunits apparently interact with each other, by the generation of heteromeric glutamate receptors with properties which are distinct from the receptors comprised of solitary glutamate receptor subunits.

Example XII

Current-Voltage Relationships for KA-Evoked Responses

This example examines the current-voltage (I/V) relationships for KA-evoked responses measured in oocytes injected with individual GluR subunits, combinations thereof, or hippocampus poly(A)+ RNA.

Figure 5A:
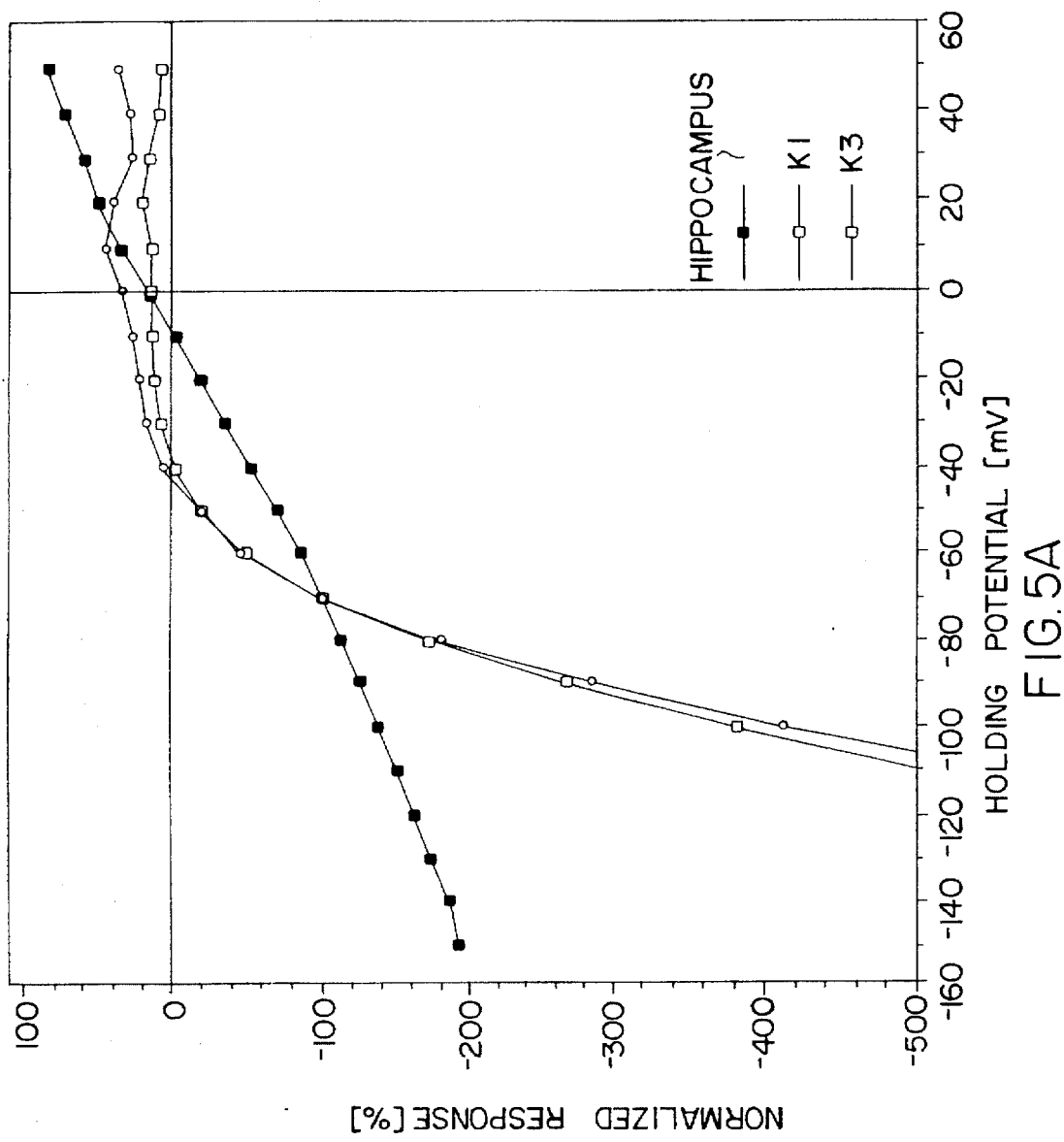
FIGS. 5A–5C are comprised of three graphs which illustrate the dependence of the current responses to 100 mM KA upon the membrane potential.
Figure 5B:
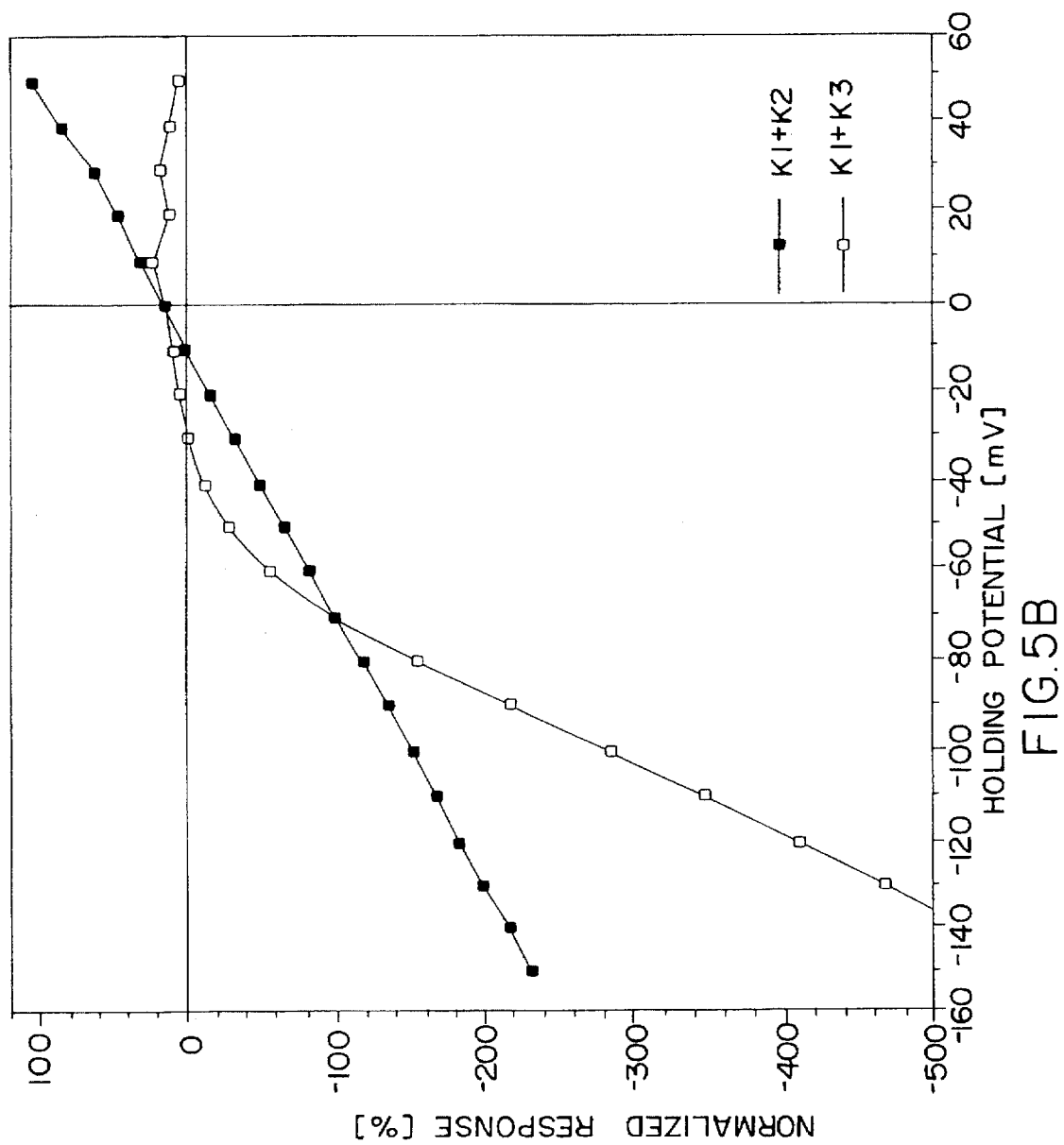
Figure 5C:
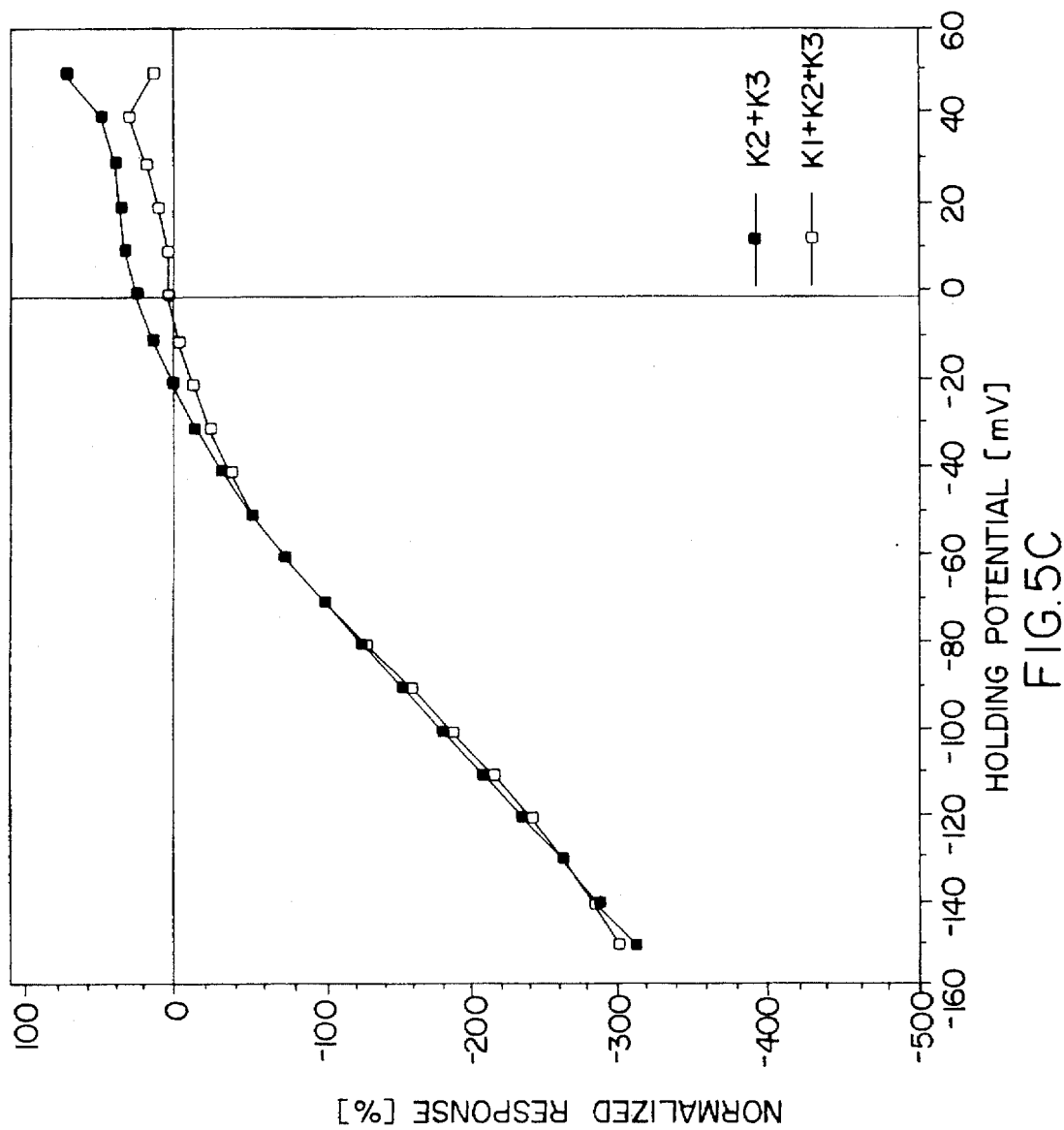

The I/V data are illustrated in FIGS. 5A–5C where the dependence of current response to exposure to 100 mM KA upon the membrane potential is shown. Data obtained from oocytes injected with individual glutamate receptor subunit RNAs are shown in FIG. 5A, data obtained from oocytes injected with combinations of subunits are shown in FIGS. 5B and 5C, and for purposes of comparison, data obtained from oocytes expressing hippocampus poly(A)+ RNA are also shown in FIG. 5A, where data obtained from oocytes injected with rat brain hippocampus poly(A)+ RNA (50 ng) are indicated by a Solid Square (■), oocytes injected with GluR1 RNA are indicated by an Open Square (□) or oocytes injected with GluR3 RNA are indicated by an Open Circle (○); FIG. 5B oocytes injected with GluR1 plus GluR2 RNAs are indicated by a Solid Square (■) or oocytes injected with GluR1 plus GluR3 RNAs are indicated by an Open Square (□); and FIG. 5C oocytes injected with GluR2 plus GluR3 RNAs are indicated by a Solid Square (■) or oocytes injected with all three GluR subunit RNAs are indicated by an Open Square (□). Recordings were made from oocytes 3 days after injection of 2 ng RNA for each GluR subunit. Voltages were stepped by 10 mV between −150 mV and +50 mV; all values are normalized to the response measured at −70 mV.

The KA responses measured in oocytes injected with brain poly(A)+ RNA show an approximately linear I/V relationship with a reversal potential of about −10 mV. This result is in marked contrast to the I/V curves obtained for oocytes injected with single GluR1 or GluR3 subunit RNA. The GluR1 and GluR3 I/V curves show strong inward rectification and reversal potentials near −40 mV. From these data it is clear that the KA-sensitive receptors present in oocytes injected with hippocampus RNA are different from those assembled by oocytes injected with GluR1 or GluR3 subunit RNAs.

In FIG. 5B the I/V curve for the GluR1 plus GluR2 combination is noticeably different from that observed for the GluR1 subunit alone. Oocytes injected with this pair of RNAs show a nearly linear I/V plot and have a reversal potential of approximately −10 mV. This plot is strikingly similar to that seen with hippocampus RNA-injected oocytes (FIG. 5A). In contrast, the I/V curve for the GluR1 plus GluR3 combination is only marginally different from those measured in oocytes expressing the individual subunits.

FIG. 5C shows some inward rectification in the I/V curve for the GluR2 plus GluR3 subunit combination, as well as a reversal potential somewhat more negative (−20 mV) than those determined for GluR1 plus GluR2 or hippocampus RNA I/V plots (−10 mV). When all three glutamate receptor subunit RNAs are combined in a single oocyte, the resulting I/V curve approximates that seen for the GluR1 plus GluR2 combination in both reversal potential and slope; however, the responses with the three subunits show a pronounced inward rectification not observed with GluR1 plus GluR2.

Example XIII

Distribution of GluR1, GluR2 and GluR3 mRNA in the Mammalian Central Nervous System The distribution of GluR1, GluR2 and GluR3 RNAs in the adult rat brain was examined to test the hypothesis that proteins encoded by the GluR1, GluR2 and GluR3 genes assemble to form heteromeric glutamate receptors in vivo. This hypothesis would be rendered highly unlikely by a showing that the individual subunit genes are transcribed in different neuroanatomical loci. The distribution of the variou subunit RNAs was examined using radiolabeled anti-sense RNA probes and in situ hybridization histochemistry essentially as described by Deneris et al. [J. Biol. Chem. 264:6268 (1989)]. The hybridization patterns obtained with the GluR1, GluR2 and GluR3 probes were nearly identical, with the strongest hybridization seen in the CA1–CA3 regions of the hippocampus and the dentate gyrus. High-resolution analysis of these areas suggests that the hybridization signal originates in the pyramidal cell layer of regions CA1–CA3 and the granule cell layer of the dentate gyrus. Somewhat weaker hybridization of all three probes was seen in the piriform cortex, caudate-putamen, amygdala, and hypothalamus. Low levels of hybridization were detected in the thalamus, with little or no signal observed in fiber tracts. While differential hybridization was seen in the medial habenula and neocortex, the overall patterns of expression for the GluR1, GluR2 and GluR3 subunit genes showed substantial concordance.

Example XIV

Isolation of cDNAs for GluR4 and GluR5

GluR4

Using a fragment of the GluR2 cDNA (nucleotides 1793–2240) as a probe in a low stringency hybridization protocol (as per Example II), several GluR4 and GluR5 clones were isolated from a rat forebrain library (as described in Example VIII). Sequence analysis demonstrated that none of the cDNA clones contained an entire open reading frame. Northern blots with mRNA from different adult rat brain tissues indicated that the GluR4 and GluR5 transcripts were most abundant in the cerebellum. Consequently, the partial GluR4 and GluR5 cDNA clones were used as probes under high stringency screening conditions to isolate cDNAs encoding large open reading frames from an adult rat cerebellum cDNA library constructed in the vector λZAP.

Of the cDNA clones thus isolated, two GluR4-related clones (λCER112 and λCER121B) encoded only portions of the GluR4 gene but possessed sufficient overlap to engineer a full-length, expressible construct in the pBS SK (+) vector (Stratagene Cloning Systems, La Jolla, Calif.). The nucleotide sequence of this GluR4 construct, designated pK45, was determined and is presented in Sequence ID No. 7, along with the deduced amino acid sequence therefor.

The GluR4 mRNA was detected on Northern blots of cerebellum RNA as a 4.6 kb species. The smaller size mRNA may represent splice variants.

GluR5

Among the 29 GluR5-related cDNAs isolated from the cerebellum library, three clones, specified λRB12, λRB15 and λRB20, were identified which encode an identical large open reading frame. The sequence of cDNA clone λRB20 (GluR5-1) is shown in Sequence ID No. 9. Cleavage of the assumed signal peptide is predicted to occur between amino acid positions 30 and 31 [von Heijne, Nucl. Acids Res 14:4683 (1986)]. This cleavage site is after a proline residue, which is atypical. The signal peptide is encoded by a fragment of about 30 amino acids. Potential sites of N-linked glycosylation are found at Asn-68, Asn-74, Asn-276, Asn-379, Asn-428, Asn-439, Asn-620 and Asn-766.

λRB15 and λRB12 are shorter than λRB20 at the 5' end. The λRB20 cDNA consists of a 5' untranslated region of 187 bp, a continuous open reading frame of 2760 bp, and a 3' untranslated region of 303 bp. The 5' untranslated region ends with the sequence AAGATGG, which is characteristic of a translational start site.

Three additional cDNA clones originally isolated from the forebrain library were also examined. The sequences of these cDNAs are identical to λRB20 in the predicted translation initiation site region. Sequence analysis revealed that two variants of the GluR5 cDNA are represented in the forebrain and the cerebellum libraries. This heterogeneity derives from the insertion of 45 nucleotides (found in λRB20 and 17 of the 29 GluR5-related cDNA clones isolated). The insertion of 45 nucleotides, as found in λRB20, but not in 12 of the 29 cDNA clones isolated, occurs between nucleotides 1388 and 1434. This insertion does not interrupt the open reading frame. Furthermore, consensus splice donor and acceptor sites are absent [Breathnach and Chambon, Ann. Rev. Biochem. 50:349–383 (1981)], which suggests that the insertion does not arise from an unspliced intron and is, most likely, the result of an alternative splice event. Nucleotide sequence analysis indicates that the two GluR5 variants are otherwise identical.

No cDNA clone was found for the shorter splice variant encoding the entire open reading frame. Therefore a clone (λRBΔ20) was constructed that is missing the 45 nucleotide insertion found in λRB20 (GluR5-1) but is otherwise identical to that clone. The shorter splice variant clone (λRBΔ20) is referred to as GluR5-2. Both λRB20 and λRBΔ20 were used in Xenopus oocyte expression experiments (see Example XVI) and the variant proteins encoded were named GluR5-1 and GluR5-2, respectively.

Northern blot analysis of cerebellum RNA indicated that the major GluR5 mRNA has a size of 6 kilobases.

Example XV

Structural Features of GluR5 cDNA and Protein

Translation of the cDNA nucleotide sequence for GluR5-1 predicts a single long open reading frame of 920 amino acid residues (see Sequence ID No. 9). The GluR5 sequence has overall amino acid sequence identity with each of the KA/AMPA subunits (see FIGS. 2A-1 to 2A-5, and Table 1). The 15 amino acid insertion in GluR5-1 is unique among the proteins listed, thus the shorter GluR5-2 variant is the counterpart to the KA/AMPA subunits characterized. Table 1 shows that GluR5 is thus far the most dissimilar glutamate receptor subunit identified; and the comparison of GluR5 with the KA/AMPA subunits highlights the most conserved sequence elements (FIGS. 2A-1 to 2A-5). Within other ligand-gated ion channel families (i.e., the neuronal nicotinic acetylcholine receptors (nAChR), the $GABA_A$ receptors and the glycine receptors), the N-terminal extracellular domain is most conserved while the C-terminal sequences diverge between the membrane-spanning regions (MSR) III and IV. In the glutamate receptor subunit gene family, in contrast, the regions N-terminal of the proposed MSR I [Hollmann et al., Nature 342:643 (1989)], have only 17% identity and are less similar than the regions C-terminal of MSR I which have 45% identity. The 'Cys—Cys loop', a signature for ligand-gated neurotransmitter receptor channel complexes [Barnard et al., Trends Neurosci. 10:502 (1987)] is not conserved in the glutamate receptor subunit family (FIGS. 2A-1 to 2A-5). The C-terminal half of glutamate receptor subunits is thought to be involved in channel formation and contain the membrane spanning regions (MSR I–IV; FIGS. 2A-1 to 2A-5). The presumed MSR III is the most conserved continuous sequence, with only one conservative amino acid exchange (Val to Ile) in the GluR5 protein (FIGS. 2A-1 to 2A-5). As mentioned above, in other ligand-gated channel families the segment between MSR III and IV is divergent in length and sequence. In the glutamate receptor subunit family the similarity in this postulated segment is high (48%) and only GluR5 exhibits a sequence length variation. The KA/AMPA receptors and the GluR5 protein are generally divergent C-terminal of the proposed MSR IV.

The hydrophobicity plot for GluR5 is similar to those of the KA/AMPA receptors, suggesting a conserved secondary structure in the proposed ion channel forming portion of the protein. However, the N-terminal half of the GluR5 hydrophobicity plot is unusual. In this region, GluR5, as compared to the KA/AMPA subunits, is more hydrophobic and contains several segments that could span the membrane. Based on algorithms that search for membrane-associated helices, four [Rao and Argos, Biochim. Biophys. Acta 869:197–214 (1986)] or seven [Eisenberg et al., J. Mol. Biol. 179:125–142 (1984)] putative transmembrane regions can be assigned to GluR5.

A comparison of the C-terminal regions of all five glutamate receptor subunits with the frog [Gregor et al., Nature 342:689 (1989)] and chicken [Wada et al., Nature 342:684 (1989)] KA binding proteins demonstrates a similar extent of sequence conservation (35–40% amino acid identity). A FASTA search [Pearson and Lipman, Proc. Natl. Acad. Sci. USA 85:2444 (1988)] of the GenBank, EMBL and SWISS-PROT databases with the GluR5 sequence uncovered no significant similarities to other proteins.

Example XVI

Electrophysiological Properties of GluR5 mRNA Injected Oocytes Exposed to L-Glutamate In vitro synthesized GluR5-1 and GluR5-2 cRNAs were individually expressed in Xenopus oocytes. With either cRNA, the glutamate receptor agonists KA (100 MM), AMPA (50 µM), quisqualate (10 µM), APB (100 µM) and NMDA (100 µM, applied with 10 µM glycine) did not elicit membrane depolarizations in cRNA injected oocytes. However, weak membrane depolarizations induced by L-glutamate (100 µM) were recorded in oocytes injected with GluR5-1 cRNA (maximal depolarization 3.5 mV) and GluR5-2 cRNA (maximal depolarization 4.5 mV). Significantly stronger membrane depolarizations were not found in response to L-glutamate in oocytes co-injected with GluR5-1 and GluR5-2 cRNA as compared to oocytes injected with GluR5-2 cRNA alone. For any particular oocyte injected with GluR5-1 or GluR5-2 cRNA, the depolarizations were reproducible, showed fast onset, and were slowly (within 5 minutes) reversed when agonist superfusion was switched to buffer superfusion. Neither un-injected oocytes nor water-injected oocytes showed a response to the glutamate receptor agonists tested. Responses to L-glutamate were recorded in 7 (out of 7) oocytes for GluR5-1 (membrane depolarization 2.29±0.26 mV S.E.M.) and 29 (out of 33) oocytes for GluR5-2 (2.27±0.19 mV S.E.M).

Example XVII

Distribution of GluR4 and GluR5 mRNA in the Developing Central and Peripheral Nervous Systems For the developmental study of GluR4 and GluR5 gene expression, sections of mice from embryonic day 10 (E10) through post natal day 21 (P21) were analyzed using in situ hybridization and histochemistry.

In the entire central nervous system (CNS), a diffuse expression of the GluR4 and GluR5 genes was detected at E10. These first hybridization signals originate from postmitotic neurons. This is best demonstrated in the myelencephalon at E12. The ependymal layer is facing the neural canal and contains dividing neuroblasts. No hybridization was detectable in these cells. The postmitotic cells are located in the exterior part of the neural tube and express both genes.

Later in development, transcripts for GluR5 and, to a lesser extent, GluR4 were particularly pronounced in areas where neurons differentiate and assemble into nuclei. These temporal changes in the hybridization pattern were best observed for GluR5 (in the primary sensory nuclei of the medulla oblongata and the nuclei of the pons which hybridized more intensely than surrounding structures at E14). GluR5 gene expression was particularly intense in several discrete brain nuclei, whereas GluR4 gene expression was detectable over the entire rostral and caudal parts of the brain.

During postnatal development, the spatial distribution of GluR4 gene transcripts did not change but usually smaller amounts of mRNA were detectable than at late embryonic stages. In contrast, GluR5 gene expression appeared to become more restricted spatially during development, and transcript levels were down-regulated. Extreme changes in the temporal GluR5 hybridization pattern were apparent in the cerebellar cortex. Until P12, high GluR5 transcript levels were detected in the granular and Purkinje cell layer. Later, the intensity of hybridization signals in the granular cell layer was reduced relative to the Purkinje cell layer and starting at P14, only a faint hybridization signal was detected in the granular cell layer.

In general, those regions of the brain that exhibited a dense labeling during embryonic development also had detectable transcript levels in adults. In P21 animals, the highest GluR4 transcript levels were observed in the cell layers of the olfactory bulb, the hippocampus, the cerebellum and the retina. In the retina, strong hybridization was found in the ganglion cell layer and in the amacrine cells of the inner nuclear layer. No expression was detected in Muller cells. For GluR5, the strongest hybridization signals at P21 were found in the olfactory bulb, the amygdala, the colliculi and some hypothalamic nuclei.

In the developing peripheral nervous system (PNS), the hybridization assays showed that the GluR4 and GluR5 genes are expressed to varying degrees in the cranial ganglia (e.g., trigeminal ganglion, acoustic ganglia), dorsal root ganglia and the mural ganglia of the intestinal organs. Comparable to the CNS, transcripts in the PNS are detected by E10 for GluR4 and by E11 for GluR5. During development, hybridization signals for GluR4 continuously increase until early postnatal stages and then persist with similar intensity in adults. Hybridization signals for GluR5 increase up to E16 and remain with comparable intensity in later developmental stages. In postnatal animals, the dorsal root ganglia (GluR5) and the mural Ganglia of the intestinal organs (GluR4 and GluR5) exhibit higher levels of hybridization than the CNS. High resolution autoradiography in the dorsal root ganglia demonstrates hybridization of the GluR5 probe over neuronal cells whereas satellite cells are unlabeled.

Example XVIII

Distribution of GluR4 and GluR5 mRNA in the Adult Mammalian (Rat) Brain

The distribution of the GluR4 and GluR5 mRNA transcripts in the adult CNS was studied by in situ hybridization. In the forebrain region, high levels of GluR4 transcripts were detected in the CA1 and the dentate gyrus of the hippocampus, in the medial habenula and particularly in the reticular thalamic nucleus. The hippocampus showed only weak expression of the GluR5 gene and no transcripts were detected in the medial habenula. The GluR5 hybridization signal was intense in the cingulate and piriform cortex, several hypothalamic nuclei, the amygdala and the lateral septum. In the cerebellum, the hybridization patterns for GluR4 and GluR5 probes were overlapping but distinct. Both probes were detected at high levels in the Purkinje cell layer. In the granular cell layer the GluR4 probe produced strong labeling, while GluR5 probe labeling was weak.

Example XIX

Isolation of GluR6 and GluR7 cDNA clones encoding the GluR6 and GluR7 genes were isolated from an adult rat forebrain library using a low-stringency hybridization screening protocol (see Example II) and a radiolabeled fragment of about 1.2 kbp (nucleotides 705–2048) of the GluR5 cDNA as a probe. The selected clones were identified by restriction digest map and sequencing.

An adult rat cerebellum cDNA library constructed in λZAP was screened under low-stringency hybridization conditions with the above-described GluR5 cDNA fragment [Bettler et al., Neuron 5: 583–595 (1990)]. A 3 kb fragment from a cDNA clone encoding part of the GluR6 open reading frame was used to rescreen the library under high-stringency hybridization conditions. Two clones, RC11 and RC27, possessed sufficient overlap to engineer a cDNA clone encoding the entire open reading frame of the GluR6 protein.

A 4559 base pair cDNA encoding a protein of 884 amino acid residues was engineered from RC11 and RC27. The protein encoded by this cDNA is referred to as GluR6. Sequence ID No. 11 shows the nucleotide and deduced amino acid sequence of the GluR6 clone. The similarity between the hydropathy profile of the GluR6 subunit and those of the GluR1–GluR5 subunits suggests a similar membrane spanning topology.

Another adult rat cerebellum cDNA library was constructed in λZAP and screened under low-stringency hybridization conditions with the above-described GluR5 cDNA fragment. A 2 kb fragment from a cDNA clone encoding part of the GluR7 open reading frame was used to rescreen the library under high-stringency hybridization conditions. Two clones, RP52 and RPC44, possessed sufficient overlap to engineer a cDNA clone encoding the entire open reading frame of the mature GluR7 protein.

A 3344 base pair cDNA encoding a protein of 921 amino acid residues was engineered from RP52 and RPC44. The protein encoded by this cDNA is referred to as GluR7. Sequence ID No. 13 shows the nucleotide and deduced amino acid sequence for the GluR7 clone.

The physiological and pharmacological properties of the homomeric GluR6 ion channel were studied in Xenopus oocytes injected with in vitro transcribed RNA. In oocytes held at −100 mV, application of kainate and glutamate evoked inward currents that desensitized in continued presence of agonist. Full recovery from desensitization caused by application of 100 µM kainate for 30 seconds required approximately 15 minutes. Quisqualate activated only small inward currents; however, quisqualate application attenuated a subsequent kainate evoked current. AMPA (100 µM) did not evoke any detectable current, nor did it antagonize a kainate-evoked current when AMPA and kainate were applied together. The AMPA solution used in the experiment did evoke responses in oocytes injected with either hippocampal mRNA or GluR1 RNA (which are both known to respond to AMPA).

Exposure of the injected oocyte to 10 µM concanavalin A (Con A) for 5 minutes efficiently decreases desensitization [see Meyer & Vyklicky, Proc. Natl. Acad. Sci. USA 86: 1411–1415 (1989)] and allows agonist-activated currents mediated by the GluR6 receptor to be more easily studied. Con A treatment increased current elicited by kainate and glutamate by 75 to 150-fold compared to the peak current for equimolar concentrations before the treatment. After Con A treatment, the maximal current induced by glutamate (relative to kainate) was 0.56±0.03 and for quisqualate 0.38±0.03. Con A treated oocytes injected with GluR6 RNA responded to kainate, but did not respond to application of 100 µM aspartate, 100 µM NMDA in the presence of 3 µM glycine, or 10–1000 µM AMPA. Furthermore, coapplication of AMPA (100 µM) had no effect on the kainate-evoked (1 µM) responses on Con A treated oocytes. It thus appears that AMPA acts as an agonist on only a subset of the kainate/quisqualate sensitive ionotropic receptors.

Figure 7A:
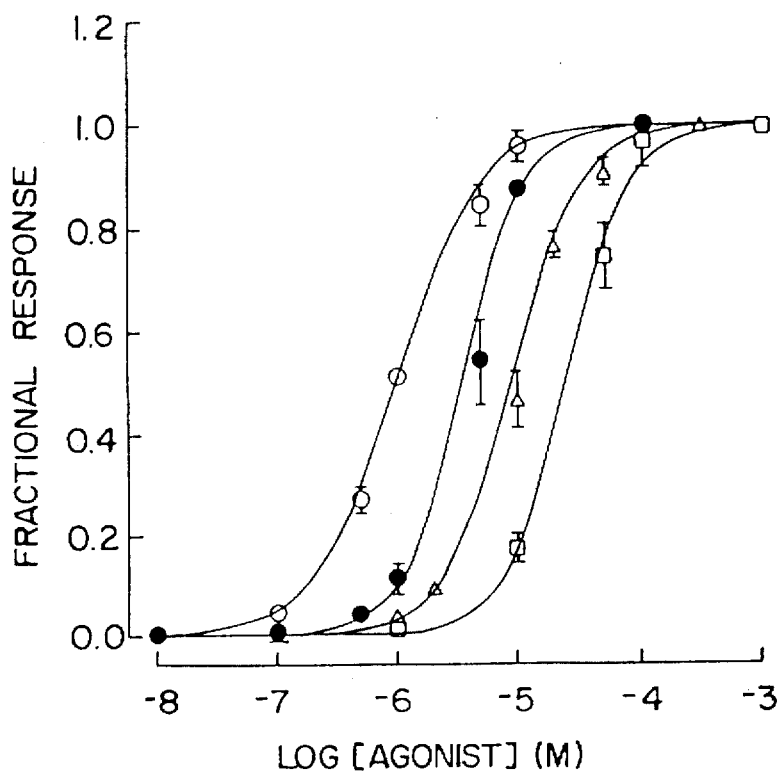
FIG. 7a presents dose response curves obtained on GluR6 injected oocytes.

The dose response curves for activation of the GluR6 receptor were obtained after Con A treatment. Data are summarized in Table 3, and in FIG. 7a, which presents dose-response curves obtained on GluR6 injected oocytes after Con A treatment for kainate (O), glutamate (□), quisqualate (Δ) and kainate in the presence of 10 µM 6-nitro-7-cyano-quinoxaline-2,3-dione (CNQX) (●). All points represent an average of 3–6 independent measurements. Error bars indicate S.E.M.

TABLE 3

$EC_{50}$ and the Maximal Agonist-evoked Current Relative to the Maximal Kainate-evoked Current for Homomeric GluR6 Receptor After Con A Treatment

| Agonist | $EC_{50}$ (µM) | Relative maximal current (±S.E.M.) |
| --- | --- | --- |
| Kainate | 1.0 (0.8–1.3) | 1.00 |
| Quisqualate | 11 (10–13) | 0.38 ± .03 |
| Glutamate | 31 (29–34) | 0.56 ± .03 |

The mean of $EC_{50}$ are based on measurements of 3–6 oocytes. The numbers in parentheses indicate 95% confidence intervals. Relative maximum current = maximum agonist-evoked current/maximum kainate-evoked current.

The $EC_{50}$ for kainate (1 µM) is about 35-fold lower than the $EC_{50}$ observed for the homomeric GluR1 ($EC_{50}$=35 µM)

receptor [see Hollmann et al., Nature 242: 643–648 (1989); Dawson et al., Mol. Pharmacol. 38: 779–784 (1990)]. The $EC_{50}$ for the GluR6 receptor is 75-fold higher for quisqualate and 10-fold higher for glutamate when compared to the same agonist on the GluR1 receptor. Thus the order of agonist potency for the homomeric GluR6 receptor is:

kainate>quisqualate>L-glutamate.

The order of agonist potency set forth above is similar to the order of binding affinities measured for quisqualate and glutamate as competitive displacers of kainate on kainate binding sites in isolated brain membranes [see Foster and Fagg, Brain Res. Rev. 7: 103–164 (1984)]. This property is clearly distinct from the GluR1 and GluR3 receptors where the relative apparent affinities are:

quisqualate>AMPA>glutamate>kainate.

[See Nakanishi et al., Neuron 5: 569–581 (1990); Boulter et al., Science 249: 1033–1037 (1990); and Foster and Fagg, supra]. Therefore, based on agonist potencies ($EC_{50}$), GluR6 can be considered a kainate receptor within the glutamate receptor family.

CNQX acts as a competitive antagonist of non-NMDA receptors in rat brain neurons [see Verdoorn et al., Mol. Pharmacol. 35:360–368 (1989)]. CNQX blocked both quisqualate and kainate-evoked responses in oocytes injected with GluR6 RNA. The inhibitory effect of 10 μM CNQX was eliminated at high kainate concentrations, consistent with its competitive mode of action. 10μM CNQX resulted in a 3.5-fold parallel shift of the kainate dose-response curve compared to the curve obtained in absence of CNQX (see FIG. 7A). Considering the competitive action of CNQX at 10 μM, the $K_i$ for CNQX was calculated to be 4 μM. Thus, CNQX is a less potent blocker of kainate responses at GluR6 receptors than at GluR1 receptors ($K_i$=0.519 μM) [see Dawson et al, supra] and kainate receptors derived from forebrain mRNA ($K_i$=0.295 μM) [see Verdoorn et al., supra] expressed in oocytes.

Figure 7B:
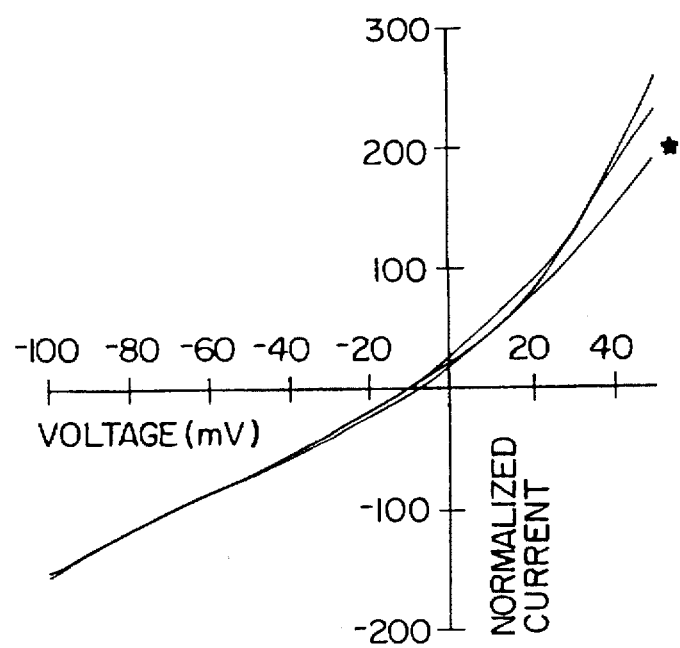
FIG. 7b presents the current-voltage relationship of the homomeric GluR6 receptor evoked by 10 μM kainate before and after Con A treatment. The asterisk indicates the I/V relationship obtained on Con A treated oocytes in a modified frog Ringer solution in which the NaCl was substituted with an equimolar concentration of sodium methanesulfonate. The currents were normalized to the individual currents measured at −70 mV (30 nA and 2.3 μa in Ringer solution before and after Con A treatment, respectively, and 330 nA in the modified Ringer solution).

The current-voltage relationship (I/V) for kainate and glutamate-evoked responses in the presence of Con A and for kainate in the absence of Con A was examined. No qualitative differences were found between Con A-treated and untreated oocytes (see FIG. 7B). The I/V relationships were assessed from 2 s voltage ramps from −100 mV to 50 mV in the presence and absence of agonist. Data were collected and analyzed using the pClamp program set. The I/V relationship exhibited a reversal potential of −10±3 mV and an outward rectification. To analyze whether the outward rectification was an intrinsic property of the channel (or perhaps an activation of endogenous chloride channels activated by a $Ca^{++}$ flux [see Miledi & Parker, J. Physiol. 357: 173–183 (1984)] through the GluR6 ion channel), the kainate-evoked I/V relationship was recorded in a buffer where 95% of the $Cl^-$ ions were substituted by an equimolar amount of methanesulfonate (which is known to shift the chloride reversal potential in a positive direction [see Verdoorn & Dingledine, Mol. Pharmacol. 34: 298–307 (1988)]). No significant change in the reversal potential was observed. Thus, if there is a $Ca^{++}$ flux in Ringer solution, it is not sufficient to activate a $Cl^-$ current. The substitution of $Cl^-$ with methanesulfonate reduced the current 8-fold; this may have been caused by either inhibition of agonist binding or a direct methanesulfonate block of the channel. The latter effect might be potentiated at positive holding potentials.

The expression pattern of the GluR6 gene was studied by in situ hybridization using brain sections from adult mice. The highest levels of GluR6 transcripts were observed in the olfactory lobe, piriform cortex, dentate gyrus, hippocampus, and in the granular cell layer of the cerebellum. In the hippocampus a gradient in hybridization intensities was observed from rostral to caudal areas, with increased intensity in the CA3 region as compared to the CA1 region. The high level of transcripts in the pyramidal cell layer of CA3 and the granule cell layer of the dentate gyrus correlates with the previously observed high level of [$^3$H] kainate binding in the stratum lucidum and the commissural/associational terminal field of the dentate gyrus, respectively [see Foster and Fagg, supra; and Monaghan & Cotman, Brain Res. 252: 91–100 (1982)]. Less intense hybridization signals were observed in the caudate putamen, the zona incerta of the thalamus, the inner and outer layers of cortex, several brain stem nuclei as well as the ganglion cell layer of the retina. In general, areas expressing high level of transcripts correlate well with areas expressing high affinity kainate binding sites.

The properties observed herein for the homomeric GluR6 receptors have not been described in studies performed on neurons. The pattern of the gene expression and the pharmacology of the GluR6 subunit suggest that this subunit might correspond or contribute to the receptor with high affinity for kainate found in the brain.

Example XX

GluR-Related Assays

The GluR cDNAs, mRNAs, proteins and functional fragments thereof, are useful in various assays designed to identify and characterize L-glutamate receptors, agonists and antagonists. For example, the cDNAs are useful as probes to identify additional members of the glutamate receptor gene family. mRNAs transcribed from the DNAs of the invention are especially useful in assays designed to identify and characterize both functional receptors and ligands. This use is especially important for the identification and design of compounds that can affect L-glutamate receptor function.

In an assay for identifying and characterizing functional receptors, mRNA is transcribed from DNAs of the invention (either full length or fragments thereof produced by deletions, substitutions, synthesis, etc.) and then translated to produce GluR proteins. In a presently preferred means for carrying out this transcription and translation, the mRNAs are translated in oocytes, preferably Xenopus oocytes. Alternatively, suitable cultured mammalian cells can be used as hosts for the production of glutamate receptor proteins. Such mammalian cells can be transfected in vitro with DNAs of the invention to yield either stable or transiently transfected cell lines. The expressed glutamate receptor proteins are then exposed to ligands known to functionally bind to and activate glutamate receptors. The physiological characteristics of the glutamate receptor proteins are measured by suitable means (e.g., by electrophysiology), and those that form functional ion channels are concluded to be functional glutamate receptor.

In a related assay designed to identify functional ligands for glutamate receptors, proteins known to functionally bind to glutamate receptor agonist or antagonist compound(s) are contacted with at least one "unknown" or test compound whose ability to effect the ion channel activity of glutamate receptors is sought to be determined (in the optional presence of a known glutamate agonist, where antagonist activity is being tested). The electrophysiological properties of the glutamate receptors are measured following exposure to the test compound(s), and those that affect the ion channel response are concluded to be functional ligands for glutamate receptors.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

SUMMARY OF SEQUENCES

Sequence ID No. 1 shows the nucleotide and deduced amino acid sequence of the clone GluR1.
Sequence ID No. 2 is the deduced amino acid sequence of the clone GluR1.
Sequence ID No. 3 shows the nucleotide and deduced amino acid sequence of the clone GluR2.
Sequence ID No. 4 is the deduced amino acid sequence of the clone GluR2.
Sequence ID No. 5 shows the nucleotide and deduced amino acid sequence of the clone GluR3.
Sequence ID No. 6 is the deduced amino acid sequence of the clone GluR3.
Sequence ID No. 7 shows the nucleotide and deduced amino acid sequence of the clone GluR4.
Sequence ID No. 8 is the deduced amino acid sequence of the clone GluR4.
Sequence ID No. 9 shows the nucleotide and deduced amino acid sequence of the cDNA clone encoding glutamate receptor subunit GluR5-1.
Sequence ID No. 10 is the deduced amino acid sequence of the clone GluR5.
Sequence ID No. 11 shows the nucleotide and deduced amino acid sequence of the clone GluR6.
Sequence ID No. 12 is the deduced amino acid sequence of the clone GluR6.
Sequence ID No. 13 shows the nucleotide and deduced amino acid sequence of fragments clone GluR7.
Sequence ID No. 14 is the deduced amino acid sequence of the clone GluR7.

What is claimed is:

1. An antibody which specifically binds a glutamate receptor protein subunit selected from the group consisting of GluR1, GluR2, GluR3, GluR4, GluR5, GluR6, and GluR7.

2. An antibody according to claim 1, wherein said subunit has the amino acid sequence set forth in SEQ ID NO:2, SEQ ID NO:4, SEQ ID NO:6, SEQ ID NO:8, SEQ ID NO:10, SEQ ID NO:12, or SEQ ID NO:14.

3. An antibody according to claim 2, wherein said antibody is a monoclonal antibody and said subunit has the same amino acid sequence as GluR1 set forth as SEQ ID NO:2.

4. An antibody according to claim 2, wherein said antibody is a monoclonal antibody and said subunit has the same amino acid sequence as GluR2 set forth as SEQ ID NO:4.

5. An antibody according to claim 2, wherein said antibody is a monoclonal antibody and said subunit has the same amino acid sequence as GluR3 set forth as SEQ ID NO:6.

6. An antibody according to claim 2, wherein said antibody is a monoclonal antibody and said subunit has the same amino acid sequence as GluR4 set forth as SEQ ID NO:8.

7. An antibody according to claim 2, wherein said antibody is a monoclonal antibody and said subunit has the same amino acid sequence as GluR5 set forth as SEQ ID NO:10.

8. An antibody according to claim 2, wherein said antibody is a monoclonal antibody and said subunit has the same amino acid sequence as GluR6 set forth as SEQ ID NO:12.

9. An antibody according to claim 2, wherein said antibody is a monoclonal antibody and said subunit has the same amino acid sequence as GluR7 set forth as SEQ ID NO:14.

10. An antibody which specifically binds a glutamate receptor protein subunit on a cell membrane, wherein said subunit is selected from the group consisting of GluR1, GluR2, GluR3, GluR4, GluR5, GluR6, and GluR7.

11. An antibody according to claim 1, wherein said antibody is a monoclonal antibody.

12. An antibody which specifically binds to a glutamate receptor protein encoded by at least one gene sequence selected from the gene sequences deposited as ATCC No. 68134, ATCC No. 68132, ATCC No. 68133, ATCC No. 68375, or ATCC No. 68374.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
  ( A ) LENGTH: 2992 base pairs
  ( B ) TYPE: nucleic acid
  ( C ) STRANDEDNESS: single
  ( D ) TOPOLOGY: linear ( i i ) MOLECULE TYPE: cDNA ( v i i ) IMMEDIATE SOURCE:
  ( B ) CLONE: GluR1

( i x ) FEATURE:
  ( A ) NAME/KEY: CDS
  ( B ) LOCATION: 198..2921

( x i ) SEQUENCE DESCRIPTION: SEQ ID NO:1:

```
AATTCGGCAC  GAGCTCGGCT  CCCCTTCCAA  GAGAAACAAG  AGAAACCTCA  CGGAAGGAAG        60

GGAGGAAGGA  AAGAAGCAAG  CAAGGAACTG  CAGGAAGAAA  AGAGCCGGCA  GAGCATCAAG       120

AAGAATCGAA  GGGAGGGGAG  GGAAGACCAA  ATCTATGGTT  GGACCAGGGC  TTCTTTTTCG       180

CCAATGTAAA  AAGGAAT ATG  CCG  TAC  ATC  TTT  GCC  TTT  TTC  TGC  ACC  GGT    230
                    Met  Pro  Tyr  Ile  Phe  Ala  Phe  Phe  Cys  Thr  Gly
                     1             5                          10

TTT  CTA  GGT  GCG  GTT  GTG  GGT  GCC  AAT  TTC  CCC  AAC  AAT  ATC  CAG  ATA    278
Phe  Leu  Gly  Ala  Val  Val  Gly  Ala  Asn  Phe  Pro  Asn  Asn  Ile  Gln  Ile
              15                      20                      25

GGG  GGG  TTA  TTT  CCA  AAC  CAA  CAA  TCA  CAG  GAA  CAT  GCG  GCT  TTT  AGG    326
Gly  Gly  Leu  Phe  Pro  Asn  Gln  Gln  Ser  Gln  Glu  His  Ala  Ala  Phe  Arg
         30                      35                      40

TTT  GCT  TTG  TCA  CAA  CTC  ACG  GAG  CCC  CCC  AAG  CTG  CTT  CCC  CAG  ATC    374
Phe  Ala  Leu  Ser  Gln  Leu  Thr  Glu  Pro  Pro  Lys  Leu  Leu  Pro  Gln  Ile
     45                      50                      55

GAT  ATT  GTG  AAC  ATC  AGC  GAC  ACG  TTT  GAG  ATG  ACT  TAC  CGT  TTC  TGT    422
Asp  Ile  Val  Asn  Ile  Ser  Asp  Thr  Phe  Glu  Met  Thr  Tyr  Arg  Phe  Cys
     60                      65                      70                      75
```

| | | | | | | | | | | | | | | | | |
|---|---|---|---|---|---|---|---|---|---|---|---|---|---|---|---|---|
| TCC | CAG | TTC | TCC | AAA | GGA | GTC | TAT | GCC | ATC | TTT | GGA | TTT | TAT | GAA | CGA | 470 |
| Ser | Gln | Phe | Ser | Lys 80 | Gly | Val | Tyr | Ala 85 | Ile | Phe | Gly | Phe | Tyr | Glu 90 | Arg | |
| AGG | ACT | GTC | AAC | ATG | CTG | ACC | TCC | TTC | TGT | GGG | GCC | CTC | CAT | GTG | TGC | 518 |
| Arg | Thr | Val | Asn 95 | Met | Leu | Thr | Ser | Phe 100 | Cys | Gly | Ala | Leu | His 105 | Val | Cys | |
| TTC | ATT | ACT | CCA | AGT | TTT | CCT | GTT | GAC | ACA | TCC | AAT | CAA | TTT | GTC | CTT | 566 |
| Phe | Ile | Thr 110 | Pro | Ser | Phe | Pro | Val 115 | Asp | Thr | Ser | Asn | Gln 120 | Phe | Val | Leu | |
| CAG | CTA | CGC | CCG | GAA | CTA | CAG | GAA | GCT | CTC | ATT | AGC | ATT | ATC | GAC | CAT | 614 |
| Gln | Leu | Arg 125 | Pro | Glu | Leu | Gln 130 | Glu | Ala | Leu | Ile | Ser 135 | Ile | Ile | Asp | His | |
| TAC | AAG | TGG | CAA | ACC | TTT | GTC | TAC | ATT | TAT | GAT | GCT | GAC | CGG | GGC | CTG | 662 |
| Tyr 140 | Lys | Trp | Gln | Thr | Phe 145 | Val | Tyr | Ile | Tyr | Asp 150 | Ala | Asp | Arg | Gly | Leu 155 | |
| TCA | GTC | CTG | CAG | AGA | GTC | TTG | GAT | ACA | GCC | GCA | GAG | AAG | AAC | TGG | CAG | 710 |
| Ser | Val | Leu | Gln | Arg 160 | Val | Leu | Asp | Thr | Ala 165 | Ala | Glu | Lys | Asn | Trp 170 | Gln | |
| GTA | ACG | GCT | GTC | AAC | ATT | CTG | ACA | ACC | ACC | GAG | GAA | GGA | TAC | CGG | ATG | 758 |
| Val | Thr | Ala | Val 175 | Asn | Ile | Leu | Thr | Thr 180 | Thr | Glu | Glu | Gly | Tyr 185 | Arg | Met | |
| CTC | TTT | CAG | GAC | CTG | GAG | AAG | AAA | AAG | GAG | AGG | CTG | GTG | GTG | GTT | GAC | 806 |
| Leu | Phe | Gln 190 | Asp | Leu | Glu | Lys | Lys 195 | Lys | Glu | Arg | Leu | Val 200 | Val | Val | Asp | |
| TGT | GAA | TCA | GAA | CGC | CTC | AAC | GCC | ATC | CTG | GGC | CAG | ATC | GTG | AAG | CTA | 854 |
| Cys | Glu 205 | Ser | Glu | Arg | Leu | Asn 210 | Ala | Ile | Leu | Gly | Gln 215 | Ile | Val | Lys | Leu | |
| GAA | AAG | AAT | GGC | ATC | GGG | TAC | CAC | TAC | ATC | CTC | GCC | AAT | CTG | GGC | TTC | 902 |
| Glu 220 | Lys | Asn | Gly | Ile | Gly 225 | Tyr | His | Tyr | Ile | Leu 230 | Ala | Asn | Leu | Gly | Phe 235 | |
| ATG | GAC | ATT | GAC | TTA | AAT | AAG | TTC | AAG | GAG | AGC | GGA | CGC | AAT | GTG | ACA | 950 |
| Met | Asp | Ile | Asp | Leu 240 | Asn | Lys | Phe | Lys | Glu 245 | Ser | Gly | Arg | Asn | Val 250 | Thr | |
| GGT | TTC | CAG | CTG | GTG | AAC | TAC | ACA | GAC | ACG | ATC | CCA | GCC | AGA | ATC | ATG | 998 |
| Gly | Phe | Gln | Leu 255 | Val | Asn | Tyr | Thr | Asp 260 | Thr | Ile | Pro | Ala | Arg 265 | Ile | Met | |
| CAG | CAA | TGG | AGG | ACA | AGT | GAC | TCC | CGA | GAC | CAT | ACC | AGG | GTG | GAC | TGG | 1046 |
| Gln | Gln | Trp 270 | Arg | Thr | Ser | Asp | Ser 275 | Arg | Asp | His | Thr | Arg 280 | Val | Asp | Trp | |
| AAG | AGG | CCA | AAG | TAC | ACT | TCT | GCT | CTC | ACC | TAT | GAT | GGT | GTC | AAG | GTG | 1094 |
| Lys | Arg 285 | Pro | Lys | Tyr | Thr | Ser 290 | Ala | Leu | Thr | Tyr | Asp 295 | Gly | Val | Lys | Val | |
| ATG | GCT | GAG | GCC | TTC | CAA | AGC | CTG | CGG | AGG | CAG | AGG | ATT | GAC | ATA | TCC | 1142 |
| Met 300 | Ala | Glu | Ala | Phe | Gln 305 | Ser | Leu | Arg | Arg | Gln 310 | Arg | Ile | Asp | Ile | Ser 315 | |
| CGC | CGG | GGG | AAT | GCT | GGG | GAC | TGT | CTG | GCT | AAC | CCA | GCT | GTG | CCC | TGG | 1190 |
| Arg | Arg | Gly | Asn | Ala 320 | Gly | Asp | Cys | Leu | Ala 325 | Asn | Pro | Ala | Val | Pro 330 | Trp | |
| GGT | CAA | GGG | ATC | GAC | ATC | CAG | AGA | GCC | CTG | CAG | CAG | GTG | CGC | TTC | GAA | 1238 |
| Gly | Gln | Gly | Ile 335 | Asp | Ile | Gln | Arg | Ala 340 | Leu | Gln | Gln | Val | Arg 345 | Phe | Glu | |
| GGT | TTG | ACA | GGA | AAT | GTG | CAG | TTC | AAC | GAG | AAA | GGG | CGC | CGG | ACC | AAT | 1286 |
| Gly | Leu | Thr 350 | Gly | Asn | Val | Gln | Phe 355 | Asn | Glu | Lys | Gly | Arg 360 | Arg | Thr | Asn | |
| TAC | ACC | CTC | CAC | GTG | ATC | GAA | ATG | AAA | CAT | GAT | GGA | ATC | CGA | AAG | ATT | 1334 |
| Tyr | Thr | Leu | His 365 | Val | Ile | Glu | Met | Lys 370 | His | Asp | Gly | Ile | Arg 375 | Lys | Ile | |
| GGT | TAC | TGG | AAT | GAA | GAC | GAT | AAA | TTT | GTC | CCC | GCA | GCC | ACC | GAC | GCT | 1382 |
| Gly 380 | Tyr | Trp | Asn | Glu | Asp 385 | Asp | Lys | Phe | Val | Pro 390 | Ala | Ala | Thr | Asp | Ala 395 | |

```
CAG GCT GGA GGG GAC AAC TCA AGC GTC CAG AAT AGG ACC TAC ATC GTC     1430
Gln Ala Gly Gly Asp Asn Ser Ser Val Gln Asn Arg Thr Tyr Ile Val
            400                 405                 410

ACT ACT ATC CTC GAA GAT CCT TAC GTG ATG CTT AAA AAG AAT GCC AAC     1478
Thr Thr Ile Leu Glu Asp Pro Tyr Val Met Leu Lys Lys Asn Ala Asn
            415                 420                 425

CAG TTT GAG GGC AAT GAC CGC TAT GAG GGC TAC TGT GTG GAG CTG GCT     1526
Gln Phe Glu Gly Asn Asp Arg Tyr Glu Gly Tyr Cys Val Glu Leu Ala
            430                 435                 440

GCA GAG ATC GCC AAG CAC GTG GGC TAC TCC TAC CGA CTT GAG ATT GTC     1574
Ala Glu Ile Ala Lys His Val Gly Tyr Ser Tyr Arg Leu Glu Ile Val
            445                 450                 455

AGC GAC GGC AAA TAT GGA GCC CGG GAT CCC GAC ACA AAG GCT TGG AAT     1622
Ser Asp Gly Lys Tyr Gly Ala Arg Asp Pro Asp Thr Lys Ala Trp Asn
460                 465                 470                 475

GGC ATG GTG GGA GAA CTG GTC TAT GGA AGA GCA GAC GTG GCT GTG GCT     1670
Gly Met Val Gly Glu Leu Val Tyr Gly Arg Ala Asp Val Ala Val Ala
                480                 485                 490

CCC TTG ACC ATA ACC TTG GTC CGG GAG GAA GTC ATC GAC TTC TCC AAG     1718
Pro Leu Thr Ile Thr Leu Val Arg Glu Glu Val Ile Asp Phe Ser Lys
            495                 500                 505

CCA TTC ATG AGT TTG GGA ATC TCC ATT ATG ATT AAG AAG CCA CAG AAG     1766
Pro Phe Met Ser Leu Gly Ile Ser Ile Met Ile Lys Lys Pro Gln Lys
            510                 515                 520

TCC AAG CCA GGT GTC TTC TCC TTT CTT GAC CCT TTG GCC TAT GAG ATC     1814
Ser Lys Pro Gly Val Phe Ser Phe Leu Asp Pro Leu Ala Tyr Glu Ile
            525                 530                 535

TGG ATG TGT ATA GTG TTT GCC TAC ATT GGA GTG AGC GTC GTC CTC TTC     1862
Trp Met Cys Ile Val Phe Ala Tyr Ile Gly Val Ser Val Val Leu Phe
540                 545                 550                 555

CTG GTC AGC CGT TTC AGC CCC TAC GAA TGG CAC AGC GAA GAG TTT GAA     1910
Leu Val Ser Arg Phe Ser Pro Tyr Glu Trp His Ser Glu Glu Phe Glu
                560                 565                 570

GAG GGA CGA GAC CAG ACA ACC AGT GAC CAG TCA AAT GAG TTT GGC ATA     1958
Glu Gly Arg Asp Gln Thr Thr Ser Asp Gln Ser Asn Glu Phe Gly Ile
            575                 580                 585

TTC AAC AGC CTG TGG TTC TCC CTG GGG GCC TTC ATG CAG CAA GGA TGT     2006
Phe Asn Ser Leu Trp Phe Ser Leu Gly Ala Phe Met Gln Gln Gly Cys
            590                 595                 600

GAC ATT TCC CCC AGG TCC CTG TCC GGA CGC ATC GTC GGC GGC GTC TGG     2054
Asp Ile Ser Pro Arg Ser Leu Ser Gly Arg Ile Val Gly Gly Val Trp
            605                 610                 615

TGG TTC TTC ACT TTG ATC ATC ATC TCC TCG TAC ACA GCC AAC CTG GCT     2102
Trp Phe Phe Thr Leu Ile Ile Ile Ser Ser Tyr Thr Ala Asn Leu Ala
620                 625                 630                 635

GCC TTC CTG ACT GTG GAG AGG ATG GTG TCT CCC ATT GAG AGT GCA GAG     2150
Ala Phe Leu Thr Val Glu Arg Met Val Ser Pro Ile Glu Ser Ala Glu
                640                 645                 650

GAC CTG GCA AAG CAG ACG GAA ATT GCT TAT GGG ACA TTG GAA GCA GGC     2198
Asp Leu Ala Lys Gln Thr Glu Ile Ala Tyr Gly Thr Leu Glu Ala Gly
            655                 660                 665

TCC ACT AAG GAG TTC TTC AGG AGA TCT AAA ATC GCT GTG TTT GAG AAG     2246
Ser Thr Lys Glu Phe Phe Arg Arg Ser Lys Ile Ala Val Phe Glu Lys
            670                 675                 680

ATG TGG ACA TAC ATG AAG TCT GCA GAA CCA TCC GTG TTT GTT CGG ACC     2294
Met Trp Thr Tyr Met Lys Ser Ala Glu Pro Ser Val Phe Val Arg Thr
685                 690                 695

ACA GAG GAA GGC ATG ATC AGA GTG AGA AAA TCT AAA GGC AAA TAC GCC     2342
Thr Glu Glu Gly Met Ile Arg Val Arg Lys Ser Lys Gly Lys Tyr Ala
700                 705                 710                 715
```

| | | | | | | | | | | | | | | | | |
|---|---|---|---|---|---|---|---|---|---|---|---|---|---|---|---|---|
|TAC|CTC|CTG|GAG|TCC|ACC|ATG|AAT|GAG|TAT|ATT|GAG|CAA|CGA|AAG|CCC|2390|
|Tyr|Leu|Leu|Glu|Ser|Thr|Met|Asn|Glu|Tyr|Ile|Glu|Gln|Arg|Lys|Pro| |
| | | | |720| | | | |725| | | | |730| | |
|TGT|GAC|ACC|ATG|AAA|GTG|GGA|GGT|AAC|TTG|GAT|TCC|AAA|GGC|TAT|GGC|2438|
|Cys|Asp|Thr|Met|Lys|Val|Gly|Gly|Asn|Leu|Asp|Ser|Lys|Gly|Tyr|Gly| |
| | | |735| | | | |740| | | | |745| | | |
|ATT|GCG|ACA|CCC|AAG|GGG|TCC|GCC|CTG|AGA|AAT|CCA|GTA|AAC|CTG|GCA|2486|
|Ile|Ala|Thr|Pro|Lys|Gly|Ser|Ala|Leu|Arg|Asn|Pro|Val|Asn|Leu|Ala| |
| | |750| | | | |755| | | | |760| | | | |
|GTG|TTA|AAA|CTG|AAC|GAG|CAG|GGG|CTT|TTG|GAC|AAA|TTG|AAA|AAC|AAA|2534|
|Val|Leu|Lys|Leu|Asn|Glu|Gln|Gly|Leu|Leu|Asp|Lys|Leu|Lys|Asn|Lys| |
| |765| | | | |770| | | | |775| | | | | |
|TGG|TGG|TAC|GAC|AAG|GGC|GAG|TGC|GGC|ACG|GGG|GGA|GGT|GAC|TCC|AAG|2582|
|Trp|Trp|Tyr|Asp|Lys|Gly|Glu|Cys|Gly|Thr|Gly|Gly|Gly|Asp|Ser|Lys| |
|780| | | | |785| | | | |790| | | | |795| |
|GAC|AAG|ACC|AGC|GCT|TTG|AGC|CTC|AGC|AAT|GTG|GCA|GGC|GTG|TTC|TAC|2630|
|Asp|Lys|Thr|Ser|Ala|Leu|Ser|Leu|Ser|Asn|Val|Ala|Gly|Val|Phe|Tyr| |
| | | | |800| | | | |805| | | | |810| | |
|ATC|CTG|ATT|GGA|GGG|CTG|GGA|CTG|GCC|ATG|CTG|GTT|GCC|TTA|ATC|GAG|2678|
|Ile|Leu|Ile|Gly|Gly|Leu|Gly|Leu|Ala|Met|Leu|Val|Ala|Leu|Ile|Glu| |
| | | |815| | | | |820| | | | |825| | | |
|TTC|TGC|TAC|AAA|TCC|CGT|AGC|GAG|TCG|AAG|CGG|ATG|AAG|GGT|TTC|TGT|2726|
|Phe|Cys|Tyr|Lys|Ser|Arg|Ser|Glu|Ser|Lys|Arg|Met|Lys|Gly|Phe|Cys| |
| | |830| | | | |835| | | | |840| | | | |
|TTG|ATC|CCA|CAG|CAA|TCC|ATC|AAT|GAA|GCC|ATA|CGG|ACA|TCG|ACC|CTC|2774|
|Leu|Ile|Pro|Gln|Gln|Ser|Ile|Asn|Glu|Ala|Ile|Arg|Thr|Ser|Thr|Leu| |
| |845| | | | |850| | | | |855| | | | | |
|CCC|CGG|AAC|AGT|GGG|GCA|GGA|GCC|AGC|GGA|GGA|GGC|GGC|AGT|GGA|GAG|2822|
|Pro|Arg|Asn|Ser|Gly|Ala|Gly|Ala|Ser|Gly|Gly|Gly|Gly|Ser|Gly|Glu| |
|860| | | | |865| | | | |870| | | | |875| |
|AAT|GGC|CGG|GTG|GTC|AGC|CAG|GAC|TTC|CCC|AAG|TCC|ATG|CAA|TCC|ATT|2870|
|Asn|Gly|Arg|Val|Val|Ser|Gln|Asp|Phe|Pro|Lys|Ser|Met|Gln|Ser|Ile| |
| | | | |880| | | | |885| | | | |890| | |
|CCC|TGC|ATG|AGT|CAC|AGT|TCA|GGG|ATG|CCC|TTG|GGA|GCC|ACA|GGA|TTG|2918|
|Pro|Cys|Met|Ser|His|Ser|Ser|Gly|Met|Pro|Leu|Gly|Ala|Thr|Gly|Leu| |
| | | |895| | | | |900| | | | |905| | | |

TAACTGGAGC AGACAGGAAA CCCTTGGGGA GCAGGCTCAG GCTTCCACAG CCCCATCCCA 2978

AGCCCTTCAG TGCC 2992

( 2 ) INFORMATION FOR SEQ ID NO:2:

( i ) SEQUENCE CHARACTERISTICS:
        ( A ) LENGTH: 907 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
|Met|Pro|Tyr|Ile|Phe|Ala|Phe|Phe|Cys|Thr|Gly|Phe|Leu|Gly|Ala|Val|
|1| | | |5| | | | |10| | | | |15| |
|Val|Gly|Ala|Asn|Phe|Pro|Asn|Asn|Ile|Gln|Ile|Gly|Gly|Leu|Phe|Pro|
| | | |20| | | | |25| | | | |30| | |
|Asn|Gln|Gln|Ser|Gln|Glu|His|Ala|Ala|Phe|Arg|Phe|Ala|Leu|Ser|Gln|
| | |35| | | | |40| | | | |45| | | |
|Leu|Thr|Glu|Pro|Pro|Lys|Leu|Leu|Pro|Gln|Ile|Asp|Ile|Val|Asn|Ile|
| |50| | | | |55| | | | |60| | | | |
|Ser|Asp|Thr|Phe|Glu|Met|Thr|Tyr|Arg|Phe|Cys|Ser|Gln|Phe|Ser|Lys|
|65| | | | |70| | | | |75| | | | |80|

```
Gly Val Tyr Ala Ile Phe Gly Phe Tyr Glu Arg Arg Thr Val Asn Met
                85              90                  95

Leu Thr Ser Phe Cys Gly Ala Leu His Val Cys Phe Ile Thr Pro Ser
            100             105                 110

Phe Pro Val Asp Thr Ser Asn Gln Phe Val Leu Gln Leu Arg Pro Glu
        115             120              125

Leu Gln Glu Ala Leu Ile Ser Ile Ile Asp His Tyr Lys Trp Gln Thr
    130                 135                 140

Phe Val Tyr Ile Tyr Asp Ala Asp Arg Gly Leu Ser Val Leu Gln Arg
145             150              155                         160

Val Leu Asp Thr Ala Ala Glu Lys Asn Trp Gln Val Thr Ala Val Asn
            165                 170                 175

Ile Leu Thr Thr Thr Glu Glu Gly Tyr Arg Met Leu Phe Gln Asp Leu
            180             185                 190

Glu Lys Lys Lys Glu Arg Leu Val Val Asp Cys Glu Ser Glu Arg
        195             200             205

Leu Asn Ala Ile Leu Gly Gln Ile Val Lys Leu Glu Lys Asn Gly Ile
    210             215                 220

Gly Tyr His Tyr Ile Leu Ala Asn Leu Gly Phe Met Asp Ile Asp Leu
225             230                 235                     240

Asn Lys Phe Lys Glu Ser Gly Arg Asn Val Thr Gly Phe Gln Leu Val
            245                 250                 255

Asn Tyr Thr Asp Thr Ile Pro Ala Arg Ile Met Gln Gln Trp Arg Thr
            260             265                 270

Ser Asp Ser Arg Asp His Thr Arg Val Asp Trp Lys Arg Pro Lys Tyr
        275             280             285

Thr Ser Ala Leu Thr Tyr Asp Gly Val Lys Val Met Ala Glu Ala Phe
    290             295                 300

Gln Ser Leu Arg Arg Gln Arg Ile Asp Ile Ser Arg Arg Gly Asn Ala
305             310             315                         320

Gly Asp Cys Leu Ala Asn Pro Ala Val Pro Trp Gly Gln Gly Ile Asp
            325             330                 335

Ile Gln Arg Ala Leu Gln Gln Val Arg Phe Glu Gly Leu Thr Gly Asn
        340             345                 350

Val Gln Phe Asn Glu Lys Gly Arg Arg Thr Asn Tyr Thr Leu His Val
        355             360                 365

Ile Glu Met Lys His Asp Gly Ile Arg Lys Ile Gly Tyr Trp Asn Glu
    370             375             380

Asp Asp Lys Phe Val Pro Ala Ala Thr Asp Ala Gln Ala Gly Gly Asp
385             390             395                         400

Asn Ser Ser Val Gln Asn Arg Thr Tyr Ile Val Thr Thr Ile Leu Glu
            405             410                 415

Asp Pro Tyr Val Met Leu Lys Lys Asn Ala Asn Gln Phe Glu Gly Asn
            420             425                 430

Asp Arg Tyr Glu Gly Tyr Cys Val Glu Leu Ala Ala Glu Ile Ala Lys
        435             440                 445

His Val Gly Tyr Ser Tyr Arg Leu Glu Ile Val Ser Asp Gly Lys Tyr
    450             455                 460

Gly Ala Arg Asp Pro Asp Thr Lys Ala Trp Asn Gly Met Val Gly Glu
465             470             475                         480

Leu Val Tyr Gly Arg Ala Asp Val Ala Val Ala Pro Leu Thr Ile Thr
            485             490                 495

Leu Val Arg Glu Glu Val Ile Asp Phe Ser Lys Pro Phe Met Ser Leu
            500             505                 510
```

-continued

| | | | | | | | | | | | | | | |
|---|---|---|---|---|---|---|---|---|---|---|---|---|---|---|
| Gly | Ile | Ser | Ile | Met | Ile | Lys | Lys | Pro | Gln | Lys | Ser | Lys | Pro | Gly | Val |
| | | 515 | | | | 520 | | | | | 525 | | | | |
| Phe | Ser | Phe | Leu | Asp | Pro | Leu | Ala | Tyr | Glu | Ile | Trp | Met | Cys | Ile | Val |
| | | 530 | | | | 535 | | | | | 540 | | | | |
| Phe | Ala | Tyr | Ile | Gly | Val | Ser | Val | Val | Leu | Phe | Leu | Val | Ser | Arg | Phe |
| 545 | | | | | 550 | | | | | 555 | | | | | 560 |
| Ser | Pro | Tyr | Glu | Trp | His | Ser | Glu | Glu | Phe | Glu | Glu | Gly | Arg | Asp | Gln |
| | | | | 565 | | | | | 570 | | | | | 575 | |
| Thr | Thr | Ser | Asp | Gln | Ser | Asn | Glu | Phe | Gly | Ile | Phe | Asn | Ser | Leu | Trp |
| | | | 580 | | | | | 585 | | | | | 590 | | |
| Phe | Ser | Leu | Gly | Ala | Phe | Met | Gln | Gln | Gly | Cys | Asp | Ile | Ser | Pro | Arg |
| | | 595 | | | | | 600 | | | | | 605 | | | |
| Ser | Leu | Ser | Gly | Arg | Ile | Val | Gly | Gly | Val | Trp | Trp | Phe | Phe | Thr | Leu |
| | | 610 | | | | 615 | | | | | 620 | | | | |
| Ile | Ile | Ile | Ser | Ser | Tyr | Thr | Ala | Asn | Leu | Ala | Ala | Phe | Leu | Thr | Val |
| 625 | | | | | 630 | | | | | 635 | | | | | 640 |
| Glu | Arg | Met | Val | Ser | Pro | Ile | Glu | Ser | Ala | Glu | Asp | Leu | Ala | Lys | Gln |
| | | | | 645 | | | | | 650 | | | | | 655 | |
| Thr | Glu | Ile | Ala | Tyr | Gly | Thr | Leu | Glu | Ala | Gly | Ser | Thr | Lys | Glu | Phe |
| | | | 660 | | | | | 665 | | | | | 670 | | |
| Phe | Arg | Arg | Ser | Lys | Ile | Ala | Val | Phe | Glu | Lys | Met | Trp | Thr | Tyr | Met |
| | | 675 | | | | | 680 | | | | | 685 | | | |
| Lys | Ser | Ala | Glu | Pro | Ser | Val | Phe | Val | Arg | Thr | Thr | Glu | Glu | Gly | Met |
| | | 690 | | | | 695 | | | | | 700 | | | | |
| Ile | Arg | Val | Arg | Lys | Ser | Lys | Gly | Lys | Tyr | Ala | Tyr | Leu | Leu | Glu | Ser |
| 705 | | | | | 710 | | | | | 715 | | | | | 720 |
| Thr | Met | Asn | Glu | Tyr | Ile | Glu | Gln | Arg | Lys | Pro | Cys | Asp | Thr | Met | Lys |
| | | | | 725 | | | | | 730 | | | | | 735 | |
| Val | Gly | Gly | Asn | Leu | Asp | Ser | Lys | Gly | Tyr | Gly | Ile | Ala | Thr | Pro | Lys |
| | | | 740 | | | | | 745 | | | | | 750 | | |
| Gly | Ser | Ala | Leu | Arg | Asn | Pro | Val | Asn | Leu | Ala | Val | Leu | Lys | Leu | Asn |
| | | 755 | | | | | 760 | | | | | 765 | | | |
| Glu | Gln | Gly | Leu | Leu | Asp | Lys | Leu | Lys | Asn | Lys | Trp | Trp | Tyr | Asp | Lys |
| | | 770 | | | | 775 | | | | | 780 | | | | |
| Gly | Glu | Cys | Gly | Thr | Gly | Gly | Gly | Asp | Ser | Lys | Asp | Lys | Thr | Ser | Ala |
| 785 | | | | | 790 | | | | | 795 | | | | | 800 |
| Leu | Ser | Leu | Ser | Asn | Val | Ala | Gly | Val | Phe | Tyr | Ile | Leu | Ile | Gly | Gly |
| | | | | 805 | | | | | 810 | | | | | 815 | |
| Leu | Gly | Leu | Ala | Met | Leu | Val | Ala | Leu | Ile | Glu | Phe | Cys | Tyr | Lys | Ser |
| | | | 820 | | | | | 825 | | | | | 830 | | |
| Arg | Ser | Glu | Ser | Lys | Arg | Met | Lys | Gly | Phe | Cys | Leu | Ile | Pro | Gln | Gln |
| | | 835 | | | | | 840 | | | | | 845 | | | |
| Ser | Ile | Asn | Glu | Ala | Ile | Arg | Thr | Ser | Thr | Leu | Pro | Arg | Asn | Ser | Gly |
| | 850 | | | | | 855 | | | | | 860 | | | | |
| Ala | Gly | Ala | Ser | Gly | Gly | Gly | Gly | Ser | Gly | Glu | Asn | Gly | Arg | Val | Val |
| 865 | | | | | 870 | | | | | 875 | | | | | 880 |
| Ser | Gln | Asp | Phe | Pro | Lys | Ser | Met | Gln | Ser | Ile | Pro | Cys | Met | Ser | His |
| | | | | 885 | | | | | 890 | | | | | 895 | |
| Ser | Ser | Gly | Met | Pro | Leu | Gly | Ala | Thr | Gly | Leu | | | | | |
| | | | 900 | | | | | 905 | | | | | | | |

( 2 ) INFORMATION FOR SEQ ID NO:3:

( i ) SEQUENCE CHARACTERISTICS:

(A) LENGTH: 3505 base pairs
(B) TYPE: nucleic acid
(C) STRANDEDNESS: single
(D) TOPOLOGY: linear (ii) MOLECULE TYPE: cDNA (vii) IMMEDIATE SOURCE:
(B) CLONE: GluR2

(ix) FEATURE:
(A) NAME/KEY: CDS
(B) LOCATION: 316..2967

(xi) SEQUENCE DESCRIPTION: SEQ ID NO:3:

```
GAATTCGGCA CGAGGTGCAT GGGAGGGTGC TGATATTCCC AGACACCAGG ACTACAGCGG        60

CAGCTCAGCT AAAAACTGCA TTCAGCCAGT CCTCGGGACT TCGGGAGCAG GGACAGGACG       120

CAAGGCATCA ACAGCCACCA GCTACAACTG GAAATAAGG ATTCTTCTGC CTTCACTTCG        180

TGTTTTTAGC AGCTCCTTGC TAAATATCGA CCTCACAATG CAGAGGATCT AATTTGCTGA       240

GGAAAACAGT CAAAGAAGGA AGAGGAAGAA AGGGAAACGA GGGGATATTT TGTGGATGCT       300

CTACTTTTCT TGGAA ATG CAA AAG ATT ATG CAT ATT TCT GTC CTC CTT TCT       351
                Met Gln Lys Ile Met His Ile Ser Val Leu Leu Ser
                 1               5                  10

CCT GTT TTA TGG GGA CTG ATT TTT GGT GTC TCT TCT AAC AGC ATA CAG        399
Pro Val Leu Trp Gly Leu Ile Phe Gly Val Ser Ser Asn Ser Ile Gln
        15                  20                  25

ATA GGG GGG CTA TTT CCA AGG GGC GCT GAT CAA GAA TAC AGT GCA TTT        447
Ile Gly Gly Leu Phe Pro Arg Gly Ala Asp Gln Glu Tyr Ser Ala Phe
        30                  35                  40

CGG GTA GGG ATG GTT CAG TTT TCC ACT TCG GAG TTC AGA CTG ACA CCC        495
Arg Val Gly Met Val Gln Phe Ser Thr Ser Glu Phe Arg Leu Thr Pro
 45                 50                  55                  60

CAT ATC GAC AAT TTG GAG GTA GCC AAC AGT TTC GCA GTC ACC AAT GCT        543
His Ile Asp Asn Leu Glu Val Ala Asn Ser Phe Ala Val Thr Asn Ala
                65                  70                  75

TTC TGC TCC CAG TTT TCA AGA GGA GTC TAC GCA ATT TTT GGA TTT TAT        591
Phe Cys Ser Gln Phe Ser Arg Gly Val Tyr Ala Ile Phe Gly Phe Tyr
                80                  85                  90

GAC AAG AAG TCT GTA AAT ACC ATC ACA TCA TTC TGT GGG ACA CTC CAT        639
Asp Lys Lys Ser Val Asn Thr Ile Thr Ser Phe Cys Gly Thr Leu His
            95                 100                 105

GTG TCC TTC ATC ACA CCT AGC TTC CCA ACA GAT GGC ACA CAT CCA TTT        687
Val Ser Phe Ile Thr Pro Ser Phe Pro Thr Asp Gly Thr His Pro Phe
   110                 115                 120

GTC ATC CAG ATG CGA CCT GAC CTC AAA GGA GCA CTC CTT AGC TTG ATT        735
Val Ile Gln Met Arg Pro Asp Leu Lys Gly Ala Leu Leu Ser Leu Ile
125                 130                 135                 140

GAG TAC TAC CAA TGG GAC AAG TTC GCA TAC CTC TAT GAC AGT GAC AGA        783
Glu Tyr Tyr Gln Trp Asp Lys Phe Ala Tyr Leu Tyr Asp Ser Asp Arg
                145                 150                 155

GGC TTA TCA ACA CTG CAA GCT GTT CTG GAT TCT GCT GCA GAG AAG AAG        831
Gly Leu Ser Thr Leu Gln Ala Val Leu Asp Ser Ala Ala Glu Lys Lys
            160                 165                 170

TGG CAG GTG ACT GCT ATC AAT GTG GGG AAC ATC AAC AAT GAC AAG AAA        879
Trp Gln Val Thr Ala Ile Asn Val Gly Asn Ile Asn Asn Asp Lys Lys
    175                 180                 185

GAT GAG ACC TAC AGA TCG CTC TTT CAA GAT CTG GAG TTA AAA AAA GAA        927
Asp Glu Thr Tyr Arg Ser Leu Phe Gln Asp Leu Glu Leu Lys Lys Glu
190                 195                 200

CGG CGT GTA ATC CTG GAC TGT GAA AGG GAT AAA GTA AAT GAC ATT GTG        975
Arg Arg Val Ile Leu Asp Cys Glu Arg Asp Lys Val Asn Asp Ile Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 205 |     |     |     |     | 210 |     |     |     |     | 215 |     |     |     |     | 220 |      |
| GAC | CAG | GTT | ATT | ACC | ATT | GGA | AAA | CAT | GTT | AAA | GGG | TAC | CAT | TAT | ATC | 1023 |
| Asp | Gln | Val | Ile | Thr | Ile | Gly | Lys | His | Val | Lys | Gly | Tyr | His | Tyr | Ile |      |
|     |     |     |     | 225 |     |     |     |     | 230 |     |     |     |     | 235 |     |      |
| ATT | GCA | AAT | CTG | GGA | TTC | ACT | GAT | GGG | GAC | CTG | CTG | AAA | ATT | CAG | TTT | 1071 |
| Ile | Ala | Asn | Leu | Gly | Phe | Thr | Asp | Gly | Asp | Leu | Leu | Lys | Ile | Gln | Phe |      |
|     |     |     | 240 |     |     |     |     | 245 |     |     |     |     | 250 |     |     |      |
| GGA | GGA | GCA | AAT | GTC | TCT | GGA | TTT | CAG | ATT | GTA | GAC | TAC | GAC | GAT | TCC | 1119 |
| Gly | Gly | Ala | Asn | Val | Ser | Gly | Phe | Gln | Ile | Val | Asp | Tyr | Asp | Asp | Ser |      |
|     |     | 255 |     |     |     |     | 260 |     |     |     |     | 265 |     |     |     |      |
| CTG | GTG | TCT | AAA | TTT | ATA | GAA | AGA | TGG | TCA | ACA | CTG | GAA | GAG | AAA | GAA | 1167 |
| Leu | Val | Ser | Lys | Phe | Ile | Glu | Arg | Trp | Ser | Thr | Leu | Glu | Glu | Lys | Glu |      |
|     |     | 270 |     |     |     |     | 275 |     |     |     |     | 280 |     |     |     |      |
| TAC | CCT | GGA | GCA | CAC | ACA | GCG | ACA | ATT | AAG | TAT | ACT | TCG | GCC | CTG | ACG | 1215 |
| Tyr | Pro | Gly | Ala | His | Thr | Ala | Thr | Ile | Lys | Tyr | Thr | Ser | Ala | Leu | Thr |      |
| 285 |     |     |     |     | 290 |     |     |     |     | 295 |     |     |     |     | 300 |      |
| TAT | GAT | GCT | GTC | CAA | GTG | ATG | ACT | GAA | GCA | TTC | CGT | AAC | CTT | CGG | AAG | 1263 |
| Tyr | Asp | Ala | Val | Gln | Val | Met | Thr | Glu | Ala | Phe | Arg | Asn | Leu | Arg | Lys |      |
|     |     |     |     | 305 |     |     |     |     | 310 |     |     |     |     | 315 |     |      |
| CAG | AGG | ATT | GAA | ATA | TCC | CGG | AGA | GGA | AAT | GCA | GGG | GAT | TGT | TTG | GCC | 1311 |
| Gln | Arg | Ile | Glu | Ile | Ser | Arg | Arg | Gly | Asn | Ala | Gly | Asp | Cys | Leu | Ala |      |
|     |     |     | 320 |     |     |     |     | 325 |     |     |     |     | 330 |     |     |      |
| AAC | CCA | GCT | GTG | CCC | TGG | GGA | CAA | GGG | GTC | GAA | ATA | GAA | AGG | GCC | CTC | 1359 |
| Asn | Pro | Ala | Val | Pro | Trp | Gly | Gln | Gly | Val | Glu | Ile | Glu | Arg | Ala | Leu |      |
|     |     | 335 |     |     |     |     | 340 |     |     |     |     | 345 |     |     |     |      |
| AAG | CAG | GTT | CAA | GTT | GAA | GGC | CTC | TCT | GGA | AAT | ATA | AAG | TTT | GAC | CAG | 1407 |
| Lys | Gln | Val | Gln | Val | Glu | Gly | Leu | Ser | Gly | Asn | Ile | Lys | Phe | Asp | Gln |      |
| 350 |     |     |     |     | 355 |     |     |     |     | 360 |     |     |     |     |     |      |
| AAT | GGA | AAA | CGA | ATA | AAC | TAC | ACA | ATT | AAC | ATC | ATG | GAG | CTC | AAA | ACA | 1455 |
| Asn | Gly | Lys | Arg | Ile | Asn | Tyr | Thr | Ile | Asn | Ile | Met | Glu | Leu | Lys | Thr |      |
| 365 |     |     |     |     | 370 |     |     |     |     | 375 |     |     |     |     | 380 |      |
| AAT | GGA | CCC | CGG | AAG | ATT | GGG | TAC | TGG | AGT | GAA | GTG | GAT | AAA | ATG | GTT | 1503 |
| Asn | Gly | Pro | Arg | Lys | Ile | Gly | Tyr | Trp | Ser | Glu | Val | Asp | Lys | Met | Val |      |
|     |     |     | 385 |     |     |     |     | 390 |     |     |     |     | 395 |     |     |      |
| GTC | ACC | CTA | ACT | GAG | CTC | CCA | TCA | GGA | AAT | GAC | ACG | TCT | GGG | CTT | GAA | 1551 |
| Val | Thr | Leu | Thr | Glu | Leu | Pro | Ser | Gly | Asn | Asp | Thr | Ser | Gly | Leu | Glu |      |
|     |     |     | 400 |     |     |     |     | 405 |     |     |     |     | 410 |     |     |      |
| AAC | AAA | ACT | GTG | GTG | GTC | ACC | ACA | ATA | TTG | GAA | TCT | CCA | TAT | GTT | ATG | 1599 |
| Asn | Lys | Thr | Val | Val | Val | Thr | Thr | Ile | Leu | Glu | Ser | Pro | Tyr | Val | Met |      |
|     |     | 415 |     |     |     |     | 420 |     |     |     |     | 425 |     |     |     |      |
| ATG | AAG | AAA | AAT | CAT | GAA | ATG | CTT | GAA | GGG | AAT | GAG | CGT | TAC | GAG | GGC | 1647 |
| Met | Lys | Lys | Asn | His | Glu | Met | Leu | Glu | Gly | Asn | Glu | Arg | Tyr | Glu | Gly |      |
|     | 430 |     |     |     |     | 435 |     |     |     |     | 440 |     |     |     |     |      |
| TAC | TGT | GTT | GAC | TTA | GCT | GCA | GAA | ATT | GCC | AAA | CAC | TGT | GGG | TTC | AAG | 1695 |
| Tyr | Cys | Val | Asp | Leu | Ala | Ala | Glu | Ile | Ala | Lys | His | Cys | Gly | Phe | Lys |      |
| 445 |     |     |     |     | 450 |     |     |     |     | 455 |     |     |     |     | 460 |      |
| TAC | AAG | CTG | ACT | ATT | GTT | GGG | GAT | GGC | AAG | TAT | GGG | GCC | AGG | GAT | GCC | 1743 |
| Tyr | Lys | Leu | Thr | Ile | Val | Gly | Asp | Gly | Lys | Tyr | Gly | Ala | Arg | Asp | Ala |      |
|     |     |     |     | 465 |     |     |     |     | 470 |     |     |     |     | 475 |     |      |
| GAC | ACC | AAA | ATT | TGG | AAT | GGT | ATG | GTT | GGA | GAG | CTT | GTC | TAC | GGG | AAA | 1791 |
| Asp | Thr | Lys | Ile | Trp | Asn | Gly | Met | Val | Gly | Glu | Leu | Val | Tyr | Gly | Lys |      |
|     |     |     | 480 |     |     |     |     | 485 |     |     |     |     | 490 |     |     |      |
| GCT | GAC | ATT | GCA | ATT | GCT | CCA | TTA | ACT | ATC | ACT | CTC | GTG | AGA | GAA | GAG | 1839 |
| Ala | Asp | Ile | Ala | Ile | Ala | Pro | Leu | Thr | Ile | Thr | Leu | Val | Arg | Glu | Glu |      |
|     |     | 495 |     |     |     |     | 500 |     |     |     |     | 505 |     |     |     |      |
| GTG | ATT | GAC | TTC | TCC | AAG | CCC | TTC | ATG | AGT | CTT | GGA | ATC | TCT | ATC | ATG | 1887 |
| Val | Ile | Asp | Phe | Ser | Lys | Pro | Phe | Met | Ser | Leu | Gly | Ile | Ser | Ile | Met |      |
|     | 510 |     |     |     |     | 515 |     |     |     |     | 520 |     |     |     |     |      |
| ATC | AAG | AAG | CCT | CAG | AAG | TCC | AAA | CCA | GGA | GTG | TTT | TCC | TTT | CTT | GAT | 1935 |
| Ile | Lys | Lys | Pro | Gln | Lys | Ser | Lys | Pro | Gly | Val | Phe | Ser | Phe | Leu | Asp |      |

|     | 525 |     |     |     | 530 |     |     |     |     | 535 |     |     |     |     | 540 |     |     |      |
|-----|-----|-----|-----|-----|-----|-----|-----|-----|-----|-----|-----|-----|-----|-----|-----|-----|-----|------|
| CCT | TTA | GCC | TAT | GAG | ATC | TGG | ATG | TGC | ATT | GTG | TTT | GCC | TAC | ATT | GGG |     |     | 1983 |
| Pro | Leu | Ala | Tyr | Glu | Ile | Trp | Met | Cys | Ile | Val | Phe | Ala | Tyr | Ile | Gly |     |     |      |
|     |     |     |     | 545 |     |     |     |     | 550 |     |     |     |     | 555 |     |     |     |      |

```
GTC AGT GTA GTT TTA TTC CTG GTC AGC AGA TTT AGC CCC TAC GAG TGG             2031
Val Ser Val Val Leu Phe Leu Val Ser Arg Phe Ser Pro Tyr Glu Trp
            560                 565                 570

CAC ACT GAG GAA TTT GAA GAT GGA AGA GAA ACA CAA AGT AGT GAA TCA             2079
His Thr Glu Glu Phe Glu Asp Gly Arg Glu Thr Gln Ser Ser Glu Ser
        575                 580                 585

ACT AAT GAA TTT GGG ATT TTT AAT AGT CTC TGG TTT TCC TTG GGT GCC             2127
Thr Asn Glu Phe Gly Ile Phe Asn Ser Leu Trp Phe Ser Leu Gly Ala
    590                 595                 600

TTT ATG CGG CAG GGA TGC GAT ATT TCG CCA AGA TCC CTC TCT GGG CGC             2175
Phe Met Arg Gln Gly Cys Asp Ile Ser Pro Arg Ser Leu Ser Gly Arg
605                 610                 615                 620

ATT GTT GGA GGT GTG TGG TGG TTC TTT ACC CTG ATC ATA ATC TCC TCC             2223
Ile Val Gly Gly Val Trp Trp Phe Phe Thr Leu Ile Ile Ile Ser Ser
                625                 630                 635

TAC ACG GCT AAC TTA GCT GCC TTC CTG ACT GTA GAG AGG ATG GTG TCT             2271
Tyr Thr Ala Asn Leu Ala Ala Phe Leu Thr Val Glu Arg Met Val Ser
            640                 645                 650

CCC ATC GAA AGT GCT GAG GAT CTG TCT AAG CAA ACA GAA ATT GCT TAT             2319
Pro Ile Glu Ser Ala Glu Asp Leu Ser Lys Gln Thr Glu Ile Ala Tyr
        655                 660                 665

GGA ACA TTA GAC TCT GGC TCC ACT AAA GAG TTT TTC AGG AGA TCT AAA             2367
Gly Thr Leu Asp Ser Gly Ser Thr Lys Glu Phe Phe Arg Arg Ser Lys
    670                 675                 680

ATC GCA GTG TTT GAT AAA ATG TGG ACT TAT ATG AGG AGT GCA GAG CCC             2415
Ile Ala Val Phe Asp Lys Met Trp Thr Tyr Met Arg Ser Ala Glu Pro
685                 690                 695                 700

TCT GTG TTT GTG AGG ACT ACC GCA GAA GGA GTA GCC AGA GTC CGG AAA             2463
Ser Val Phe Val Arg Thr Thr Ala Glu Gly Val Ala Arg Val Arg Lys
                705                 710                 715

TCC AAA GGA AAG TAT GCC TAC TTG CTG GAG TCC ACA ATG AAC GAG TAC             2511
Ser Lys Gly Lys Tyr Ala Tyr Leu Leu Glu Ser Thr Met Asn Glu Tyr
            720                 725                 730

ATC GAG CAG AGG AAG CCT TGT GAC ACC ATG AAA GTG GGA GGA AAC TTG             2559
Ile Glu Gln Arg Lys Pro Cys Asp Thr Met Lys Val Gly Gly Asn Leu
        735                 740                 745

GAT TCC AAA GGC TAC GGC ATC GCC ACA CCT AAA GGA TCC TCA TTA GGA             2607
Asp Ser Lys Gly Tyr Gly Ile Ala Thr Pro Lys Gly Ser Ser Leu Gly
    750                 755                 760

AAT GCG GTT AAC CTC GCA GTA CTA AAA CTG AAT GAA CAA GGC CTG TTG             2655
Asn Ala Val Asn Leu Ala Val Leu Lys Leu Asn Glu Gln Gly Leu Leu
765                 770                 775                 780

GAC AAA TTG AAA AAC AAA TGG TGG TAC GAC AAA GGA GAG TGC GGC AGC             2703
Asp Lys Leu Lys Asn Lys Trp Trp Tyr Asp Lys Gly Glu Cys Gly Ser
                785                 790                 795

GGG GGA GGT GAT TCC AAG GAA AAG ACC AGT GCC CTC AGT CTG AGC AAC             2751
Gly Gly Gly Asp Ser Lys Glu Lys Thr Ser Ala Leu Ser Leu Ser Asn
            800                 805                 810

GTT GCT GGA GTA TTC TAC ATC CTT GTC GGG GGC CTT GGT TTG GCA ATG             2799
Val Ala Gly Val Phe Tyr Ile Leu Val Gly Gly Leu Gly Leu Ala Met
        815                 820                 825

CTG GTG GCT TTG ATT GAG TTC TGT TAC AAG TCA AGG GCC GAG GCG AAA             2847
Leu Val Ala Leu Ile Glu Phe Cys Tyr Lys Ser Arg Ala Glu Ala Lys
    830                 835                 840

CGA ATG AAG GTG GCA AAG AAT CCA CAG AAT ATT AAC CCA TCT TCC TCG             2895
Arg Met Lys Val Ala Lys Asn Pro Gln Asn Ile Asn Pro Ser Ser Ser
```

-continued

```
                845                    850                    855                    860
CAG AAT TCC CAG AAT TTT GCA ACT TAT AAG GAA GGT TAC AAC GTA TAT              2943
Gln Asn Ser Gln Asn Phe Ala Thr Tyr Lys Glu Gly Tyr Asn Val Tyr
                865                    870                    875

GGC ATC GAG AGT GTT AAA ATT TAGGGGATGA CCTTGAGTGA TGTCATGAGG                 2994
Gly Ile Glu Ser Val Lys Ile
                880

AGCAAGGCAA GGCTGTCAAT TACAGGAAGT ACTGGAGAAA ATGGACGTGT TATGACTCCA            3054
GAATTTCCCA AAGCAGTGCA TGCTGTCCCT TACGTGAGTC CTGGCATGGG AATGAATGTC            3114
AGTGTGACTG ATCTCTCGTG ATTGATAGGA ACCTTCTGAG TGCCTTACAC AATGGTTTCC            3174
TTGTGTGTTT ATTGTCAAAG TGGTGAGAGG CATCCGATAT CTTGAAGGCT TTTCTTTCAG            3234
CCAAGAATTC TTAACTATGT GGAGTTCACC TTGAATTGTA AGGAAAGATA AATTACAAAC            3294
AGAGCATCAT TTTCTACTCC GATATCAGAG GAAGCGTGGT GGACATGCAC AGCTAACATG            3354
GAAATACTAT CATTTAACTG AAGTCTTTGT ACAGACAACA AACCCGTTTC CGCAGCCACT            3414
ATTGTTAGTC TCTTGATTCA TAATGACTTA AGCACACTTG ACATCAACTG CATCAAGATG            3474
TGACCTGTTT TATAAAAAAA AAAAAAAAA A                                            3505
```

( 2 ) INFORMATION FOR SEQ ID NO:4:

( i ) SEQUENCE CHARACTERISTICS:
        ( A ) LENGTH: 883 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Gln Lys Ile Met His Ile Ser Val Leu Leu Ser Pro Val Leu Trp
  1               5                  10                  15

Gly Leu Ile Phe Gly Val Ser Ser Asn Ser Ile Gln Ile Gly Gly Leu
             20                  25                  30

Phe Pro Arg Gly Ala Asp Gln Glu Tyr Ser Ala Phe Arg Val Gly Met
         35                  40                  45

Val Gln Phe Ser Thr Ser Glu Phe Arg Leu Thr Pro His Ile Asp Asn
 50                  55                  60

Leu Glu Val Ala Asn Ser Phe Ala Val Thr Asn Ala Phe Cys Ser Gln
 65                  70                  75                  80

Phe Ser Arg Gly Val Tyr Ala Ile Phe Gly Phe Tyr Asp Lys Lys Ser
             85                  90                  95

Val Asn Thr Ile Thr Ser Phe Cys Gly Thr Leu His Val Ser Phe Ile
            100                 105                 110

Thr Pro Ser Phe Pro Thr Asp Gly Thr His Pro Phe Val Ile Gln Met
        115                 120                 125

Arg Pro Asp Leu Lys Gly Ala Leu Leu Ser Leu Ile Glu Tyr Tyr Gln
130                 135                 140

Trp Asp Lys Phe Ala Tyr Leu Tyr Asp Ser Asp Arg Gly Leu Ser Thr
145                 150                 155                 160

Leu Gln Ala Val Leu Asp Ser Ala Ala Glu Lys Lys Trp Gln Val Thr
            165                 170                 175

Ala Ile Asn Val Gly Asn Ile Asn Asn Asp Lys Lys Asp Glu Thr Tyr
        180                 185                 190

Arg Ser Leu Phe Gln Asp Leu Glu Leu Lys Lys Glu Arg Arg Val Ile
    195                 200                 205

Leu Asp Cys Glu Arg Asp Lys Val Asn Asp Ile Val Asp Gln Val Ile
```

-continued

```
              210                     215                          220
Thr  Ile  Gly  Lys  His  Val  Lys  Gly  Tyr  His  Tyr  Ile  Ile  Ala  Asn  Leu
225                      230                      235                      240

Gly  Phe  Thr  Asp  Gly  Asp  Leu  Leu  Lys  Ile  Gln  Phe  Gly  Gly  Ala  Asn
                         245                      250                      255

Val  Ser  Gly  Phe  Gln  Ile  Val  Asp  Tyr  Asp  Asp  Ser  Leu  Val  Ser  Lys
                    260                      265                      270

Phe  Ile  Glu  Arg  Trp  Ser  Thr  Leu  Glu  Glu  Lys  Glu  Tyr  Pro  Gly  Ala
               275                      280                      285

His  Thr  Ala  Thr  Ile  Lys  Tyr  Thr  Ser  Ala  Leu  Thr  Tyr  Asp  Ala  Val
          290                      295                      300

Gln  Val  Met  Thr  Glu  Ala  Phe  Arg  Asn  Leu  Arg  Lys  Gln  Arg  Ile  Glu
305                      310                      315                      320

Ile  Ser  Arg  Arg  Gly  Asn  Ala  Gly  Asp  Cys  Leu  Ala  Asn  Pro  Ala  Val
                         325                      330                      335

Pro  Trp  Gly  Gln  Gly  Val  Glu  Ile  Glu  Arg  Ala  Leu  Lys  Gln  Val  Gln
                    340                      345                      350

Val  Glu  Gly  Leu  Ser  Gly  Asn  Ile  Lys  Phe  Asp  Gln  Asn  Gly  Lys  Arg
               355                      360                      365

Ile  Asn  Tyr  Thr  Ile  Asn  Ile  Met  Glu  Leu  Lys  Thr  Asn  Gly  Pro  Arg
          370                      375                      380

Lys  Ile  Gly  Tyr  Trp  Ser  Glu  Val  Asp  Lys  Met  Val  Val  Thr  Leu  Thr
385                      390                      395                      400

Glu  Leu  Pro  Ser  Gly  Asn  Asp  Thr  Ser  Gly  Leu  Glu  Asn  Lys  Thr  Val
                         405                      410                      415

Val  Val  Thr  Thr  Ile  Leu  Glu  Ser  Pro  Tyr  Val  Met  Met  Lys  Lys  Asn
                    420                      425                      430

His  Glu  Met  Leu  Glu  Gly  Asn  Glu  Arg  Tyr  Glu  Gly  Tyr  Cys  Val  Asp
               435                      440                      445

Leu  Ala  Ala  Glu  Ile  Ala  Lys  His  Cys  Gly  Phe  Lys  Tyr  Lys  Leu  Thr
          450                      455                      460

Ile  Val  Gly  Asp  Gly  Lys  Tyr  Gly  Ala  Arg  Asp  Ala  Asp  Thr  Lys  Ile
465                      470                      475                      480

Trp  Asn  Gly  Met  Val  Gly  Glu  Leu  Val  Tyr  Gly  Lys  Ala  Asp  Ile  Ala
                    485                      490                      495

Ile  Ala  Pro  Leu  Thr  Ile  Thr  Leu  Val  Arg  Glu  Glu  Val  Ile  Asp  Phe
               500                      505                      510

Ser  Lys  Pro  Phe  Met  Ser  Leu  Gly  Ile  Ser  Ile  Met  Ile  Lys  Lys  Pro
          515                      520                      525

Gln  Lys  Ser  Lys  Pro  Gly  Val  Phe  Ser  Phe  Leu  Asp  Pro  Leu  Ala  Tyr
530                      535                      540

Glu  Ile  Trp  Met  Cys  Ile  Val  Phe  Ala  Tyr  Ile  Gly  Val  Ser  Val  Val
545                      550                      555                      560

Leu  Phe  Leu  Val  Ser  Arg  Phe  Ser  Pro  Tyr  Glu  Trp  His  Thr  Glu  Glu
                    565                      570                      575

Phe  Glu  Asp  Gly  Arg  Glu  Thr  Gln  Ser  Ser  Glu  Ser  Thr  Asn  Glu  Phe
               580                      585                      590

Gly  Ile  Phe  Asn  Ser  Leu  Trp  Phe  Ser  Leu  Gly  Ala  Phe  Met  Arg  Gln
          595                      600                      605

Gly  Cys  Asp  Ile  Ser  Pro  Arg  Ser  Leu  Ser  Gly  Arg  Ile  Val  Gly  Gly
     610                      615                      620

Val  Trp  Trp  Phe  Phe  Thr  Leu  Ile  Ile  Ile  Ser  Ser  Tyr  Thr  Ala  Asn
625                      630                      635                      640
```

```
Leu Ala Ala Phe Leu Thr Val Glu Arg Met Val Ser Pro Ile Glu Ser
                645             650             655
Ala Glu Asp Leu Ser Lys Gln Thr Glu Ile Ala Tyr Gly Thr Leu Asp
            660             665             670
Ser Gly Ser Thr Lys Glu Phe Phe Arg Arg Ser Lys Ile Ala Val Phe
        675             680             685
Asp Lys Met Trp Thr Tyr Met Arg Ser Ala Glu Pro Ser Val Phe Val
    690             695             700
Arg Thr Thr Ala Glu Gly Val Ala Arg Val Arg Lys Ser Lys Gly Lys
705             710             715             720
Tyr Ala Tyr Leu Leu Glu Ser Thr Met Asn Glu Tyr Ile Glu Gln Arg
                725             730             735
Lys Pro Cys Asp Thr Met Lys Val Gly Gly Asn Leu Asp Ser Lys Gly
            740             745             750
Tyr Gly Ile Ala Thr Pro Lys Gly Ser Ser Leu Gly Asn Ala Val Asn
        755             760             765
Leu Ala Val Leu Lys Leu Asn Glu Gln Gly Leu Leu Asp Lys Leu Lys
    770             775             780
Asn Lys Trp Trp Tyr Asp Lys Gly Glu Cys Gly Ser Gly Gly Gly Asp
785             790             795             800
Ser Lys Glu Lys Thr Ser Ala Leu Ser Leu Ser Asn Val Ala Gly Val
                805             810             815
Phe Tyr Ile Leu Val Gly Gly Leu Gly Leu Ala Met Leu Val Ala Leu
            820             825             830
Ile Glu Phe Cys Tyr Lys Ser Arg Ala Glu Ala Lys Arg Met Lys Val
        835             840             845
Ala Lys Asn Pro Gln Asn Ile Asn Pro Ser Ser Ser Gln Asn Ser Gln
    850             855             860
Asn Phe Ala Thr Tyr Lys Glu Gly Tyr Asn Val Tyr Gly Ile Glu Ser
865             870             875             880
Val Lys Ile
```

( 2 ) INFORMATION FOR SEQ ID NO:5:

( i ) SEQUENCE CHARACTERISTICS:
( A ) LENGTH: 3083 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: GluR3

( i x ) FEATURE:
( A ) NAME/KEY: CDS
( B ) LOCATION: 167..2833

( x i ) SEQUENCE DESCRIPTION: SEQ ID NO:5:

```
GCTCTCTCTC TCTCTCTCTC TCTCTCTCTC TCTCTCTCTC TCTCTCTCTC TTCTCTCAGA          60

AATCGCTTTG GGGAACCCAG CTTGCAGCCA ATGAACCCGC CTTCCAGATT GGTGTGAAGA         120

CAGAAGTGAG CTTCGTTTTA GGCGTCAAGC AGCCAGGCAG AAGAAA ATG GGG CAA           175
                                                 Met Gly Gln
                                                  1

AGC GTG CTC CGG GCG GTC TTC TTT TTA GTC CTG GGG CTT TTG GGT CAT           223
Ser Val Leu Arg Ala Val Phe Phe Leu Val Leu Gly Leu Leu Gly His
      5                  10                 15

TCT CAC GGA GGA TTC CCC AAC ACC ATC AGC ATA GGT GGA CTT TTC ATG           271
```

-continued

```
Ser His Gly Gly Phe Pro Asn Thr Ile Ser Ile Gly Gly Leu Phe Met
 20              25              30                     35

AGA AAC ACG GTT CAG GAG CAC AGC GCT TTC CGC TTT GCT GTG CAG TTA        319
Arg Asn Thr Val Gln Glu His Ser Ala Phe Arg Phe Ala Val Gln Leu
             40              45                      50

TAC AAC ACC AAC CAG AAC ACC ACT GAG AAG CCC TTC CAT TTG AAT TAC        367
Tyr Asn Thr Asn Gln Asn Thr Thr Glu Lys Pro Phe His Leu Asn Tyr
                 55              60                 65

CAC GTA GAC CAC TTG GAT TCC TCC AAT AGT TTT TCT GTG ACT AAT GCT        415
His Val Asp His Leu Asp Ser Ser Asn Ser Phe Ser Val Thr Asn Ala
         70              75              80

TTC TGC TCC CAG TTC TCC AGA GGG GTG TAT GCT ATC TTT GGA TTC TAT        463
Phe Cys Ser Gln Phe Ser Arg Gly Val Tyr Ala Ile Phe Gly Phe Tyr
     85              90              95

GAC CAG ATG TCA ATG AAC ACC CTG ACC TCC TTC TGT GGG GCC CTG CAC        511
Asp Gln Met Ser Met Asn Thr Leu Thr Ser Phe Cys Gly Ala Leu His
100             105             110                     115

ACA TCT TTT GTC ACA CCT AGC TTT CCC ACT GAT GCA GAT GTG CAG TTT        559
Thr Ser Phe Val Thr Pro Ser Phe Pro Thr Asp Ala Asp Val Gln Phe
                 120             125                    130

GTC ATC CAG ATG CGC CCA GCC TTG AAG GGT GCC ATT CTG AGT CTT CTC        607
Val Ile Gln Met Arg Pro Ala Leu Lys Gly Ala Ile Leu Ser Leu Leu
         135             140                     145

AGT TAC TAC AAG TGG GAG AAG TTT GTG TAC CTC TAT GAC ACA GAA CGA        655
Ser Tyr Tyr Lys Trp Glu Lys Phe Val Tyr Leu Tyr Asp Thr Glu Arg
     150             155                 160

GGG TTT TCT GTC CTA CAA GCA ATT ATG GAG GCA GCA GTG CAA AAC AAC        703
Gly Phe Ser Val Leu Gln Ala Ile Met Glu Ala Ala Val Gln Asn Asn
165             170                 175

TGG CAA GTG ACA GCA AGG TCT GTG GGA AAC ATA AAG GAC GTC CAG GAA        751
Trp Gln Val Thr Ala Arg Ser Val Gly Asn Ile Lys Asp Val Gln Glu
180             185             190                     195

TTC AGA CGC ATC ATT GAA GAA ATG GAC AGA AGG CAG GAA AAA CGA TAC        799
Phe Arg Arg Ile Ile Glu Glu Met Asp Arg Arg Gln Glu Lys Arg Tyr
                 200             205                    210

TTG ATT GAC TGT GAA GTC GAA AGG ATT AAC ACA ATT TTG GAA CAG GTT        847
Leu Ile Asp Cys Glu Val Glu Arg Ile Asn Thr Ile Leu Glu Gln Val
         215             220                     225

GTG ATC CTG GGG AAG CAT TCA AGA GGC TAT CAC TAC ATG CTT GCT AAC        895
Val Ile Leu Gly Lys His Ser Arg Gly Tyr His Tyr Met Leu Ala Asn
     230             235                     240

CTG GGT TTT ACT GAC ATT TTA CTG GAA AGA GTC ATG CAT GGG GGA GCC        943
Leu Gly Phe Thr Asp Ile Leu Leu Glu Arg Val Met His Gly Gly Ala
     245             250             255

AAC ATT ACA GGT TTC CAG ATT GTC AAC AAT GAA AAC CCA ATG GTT CAG        991
Asn Ile Thr Gly Phe Gln Ile Val Asn Asn Glu Asn Pro Met Val Gln
260             265             270                     275

CAG TTC ATA CAG CGC TGG GTG AGA CTG GAT GAA AGG GAA TTC CCT GAA       1039
Gln Phe Ile Gln Arg Trp Val Arg Leu Asp Glu Arg Glu Phe Pro Glu
                 280             285                    290

GCC AAG AAT GCA CCA CTG AAG TAT ACA TCT GCG CTG ACA CAT GAC GCA       1087
Ala Lys Asn Ala Pro Leu Lys Tyr Thr Ser Ala Leu Thr His Asp Ala
             295             300                     305

ATA TTG GTC ATA GCA GAA GCC TTC CGA TAC CTG AGG AGA CAG AGA GTG       1135
Ile Leu Val Ile Ala Glu Ala Phe Arg Tyr Leu Arg Arg Gln Arg Val
             310             315                     320

GAT GTC TCC CGC AGA GGC AGT GCT GGA GAC TGC TTA GCA AAT CCT GCT       1183
Asp Val Ser Arg Arg Gly Ser Ala Gly Asp Cys Leu Ala Asn Pro Ala
325             330                     335

GTG CCC TGG AGT CAA GGA ATT GAT ATT GAG AGA GCT CTG AAA ATG GTG       1231
```

| | | | | | | | | | | | | | | | | |
|---|---|---|---|---|---|---|---|---|---|---|---|---|---|---|---|---|
| Val | Pro | Trp | Ser | Gln | Gly | Ile | Asp | Ile | Glu | Arg | Ala | Leu | Lys | Met | Val | |
| 340 | | | | 345 | | | | | 350 | | | | | | 355 | |
| CAA | GTA | CAA | GGA | ATG | ACT | GGA | AAC | ATC | CAA | TTT | GAC | ACT | TAT | GGA | CGT | 1279 |
| Gln | Val | Gln | Gly | Met | Thr | Gly | Asn | Ile | Gln | Phe | Asp | Thr | Tyr | Gly | Arg | |
| | | | | 360 | | | | | 365 | | | | | 370 | | |
| AGG | ACA | AAT | TAT | ACC | ATT | GAT | GTC | TAT | GAA | ATG | AAA | GTC | TCG | GGT | TCT | 1327 |
| Arg | Thr | Asn | Tyr | Thr | Ile | Asp | Val | Tyr | Glu | Met | Lys | Val | Ser | Gly | Ser | |
| | | | 375 | | | | | 380 | | | | | 385 | | | |
| CGA | AAA | GCT | GGT | TAC | TGG | AAC | GAA | TAT | GAA | AGG | TTT | GTG | CCC | TTC | TCA | 1375 |
| Arg | Lys | Ala | Gly | Tyr | Trp | Asn | Glu | Tyr | Glu | Arg | Phe | Val | Pro | Phe | Ser | |
| | | 390 | | | | | 395 | | | | | 400 | | | | |
| GAT | CAA | CAA | ATC | AGC | AAT | GAC | AGC | TCA | TCC | TCA | GAG | AAC | CGG | ACC | ATT | 1423 |
| Asp | Gln | Gln | Ile | Ser | Asn | Asp | Ser | Ser | Ser | Ser | Glu | Asn | Arg | Thr | Ile | |
| | 405 | | | | 410 | | | | | 415 | | | | | | |
| GTA | GTG | ACT | ACC | ATT | CTG | GAA | TCA | CCA | TAT | GTG | ATG | TAT | AAA | AAG | AAT | 1471 |
| Val | Val | Thr | Thr | Ile | Leu | Glu | Ser | Pro | Tyr | Val | Met | Tyr | Lys | Lys | Asn | |
| 420 | | | | | 425 | | | | | 430 | | | | | 435 | |
| CAT | GAG | CAG | CTG | GAA | GGA | AAT | GAG | CGC | TAT | GAA | GGC | TAC | TGT | GTT | GAT | 1519 |
| His | Glu | Gln | Leu | Glu | Gly | Asn | Glu | Arg | Tyr | Glu | Gly | Tyr | Cys | Val | Asp | |
| | | | | 440 | | | | | 445 | | | | | 450 | | |
| TTA | GCC | TAT | GAA | ATA | GCC | AAA | CAC | GTA | AGG | ATC | AAA | TAC | AAA | TTG | TCC | 1567 |
| Leu | Ala | Tyr | Glu | Ile | Ala | Lys | His | Val | Arg | Ile | Lys | Tyr | Lys | Leu | Ser | |
| | | | 455 | | | | | 460 | | | | | 465 | | | |
| ATT | GTC | GGT | GAT | GGG | AAA | TAT | GGC | GCC | AGA | GAT | CCA | GAG | ACT | AAA | ATA | 1615 |
| Ile | Val | Gly | Asp | Gly | Lys | Tyr | Gly | Ala | Arg | Asp | Pro | Glu | Thr | Lys | Ile | |
| | | 470 | | | | | 475 | | | | | 480 | | | | |
| TGG | AAT | GGC | ATG | GTT | GGG | GAA | CTT | GTC | TAT | GGA | AGA | GCT | GAT | ATA | GCT | 1663 |
| Trp | Asn | Gly | Met | Val | Gly | Glu | Leu | Val | Tyr | Gly | Arg | Ala | Asp | Ile | Ala | |
| | 485 | | | | 490 | | | | | 495 | | | | | | |
| GTT | GCT | CCA | CTC | ACT | ATA | ACA | TTG | GTC | CGT | GAA | GAA | GTC | ATA | GAT | TTC | 1711 |
| Val | Ala | Pro | Leu | Thr | Ile | Thr | Leu | Val | Arg | Glu | Glu | Val | Ile | Asp | Phe | |
| 500 | | | | | 505 | | | | | 510 | | | | | 515 | |
| TCA | AAC | GCA | TTT | ATG | AGC | CTG | GGA | ATC | TCC | ATC | ATG | ATA | AAG | AAG | CCT | 1759 |
| Ser | Asn | Ala | Phe | Met | Ser | Leu | Gly | Ile | Ser | Ile | Met | Ile | Lys | Lys | Pro | |
| | | | | 520 | | | | | 525 | | | | | 530 | | |
| CAG | AAA | TCA | AAG | CCA | GGC | GTC | TTT | TCA | TTC | CTG | GAT | CCT | TTG | GCT | TAT | 1807 |
| Gln | Lys | Ser | Lys | Pro | Gly | Val | Phe | Ser | Phe | Leu | Asp | Pro | Leu | Ala | Tyr | |
| | | | 535 | | | | | 540 | | | | | 545 | | | |
| GAA | ATC | TGG | ATG | TGC | ATT | GTC | TTC | GCT | TAC | ATT | GGA | GTC | AGT | GTA | GTT | 1855 |
| Glu | Ile | Trp | Met | Cys | Ile | Val | Phe | Ala | Tyr | Ile | Gly | Val | Ser | Val | Val | |
| | | 550 | | | | | 555 | | | | | 560 | | | | |
| CTC | TTC | CTA | GTC | AGC | AGA | TTT | AGC | CCT | TAT | GAA | TGG | CAC | TTG | GAA | GAC | 1903 |
| Leu | Phe | Leu | Val | Ser | Arg | Phe | Ser | Pro | Tyr | Glu | Trp | His | Leu | Glu | Asp | |
| | 565 | | | | 570 | | | | | 575 | | | | | | |
| AAC | AAT | GAA | GAA | CCT | CGT | GAC | CCA | CAA | AGC | CCT | CCT | GAT | CCT | CCC | AAT | 1951 |
| Asn | Asn | Glu | Glu | Pro | Arg | Asp | Pro | Gln | Ser | Pro | Pro | Asp | Pro | Pro | Asn | |
| 580 | | | | | 585 | | | | | 590 | | | | | 595 | |
| GAA | TTT | GGA | ATA | TTT | AAC | AGT | CTT | TGG | TTT | TCC | TTG | GGT | GCT | TTC | ATG | 1999 |
| Glu | Phe | Gly | Ile | Phe | Asn | Ser | Leu | Trp | Phe | Ser | Leu | Gly | Ala | Phe | Met | |
| | | | | 600 | | | | | 605 | | | | | 610 | | |
| CAG | CAA | GGA | TGT | GAT | ATT | TCT | CCA | AGA | TCA | CTT | TCT | GGG | CGC | ATT | GTT | 2047 |
| Gln | Gln | Gly | Cys | Asp | Ile | Ser | Pro | Arg | Ser | Leu | Ser | Gly | Arg | Ile | Val | |
| | | | 615 | | | | | 620 | | | | | 625 | | | |
| GGA | GGG | GTT | TGG | TGG | TTC | TTC | ACC | CTG | ATC | ATA | ATC | TCT | TCC | TAC | ACT | 2095 |
| Gly | Gly | Val | Trp | Trp | Phe | Phe | Thr | Leu | Ile | Ile | Ile | Ser | Ser | Tyr | Thr | |
| | | 630 | | | | | 635 | | | | | 640 | | | | |
| GCA | AAC | CTT | GCT | GCT | TTC | CTG | ACT | GTG | GAG | AGG | ATG | GTG | TCC | CCT | ATA | 2143 |
| Ala | Asn | Leu | Ala | Ala | Phe | Leu | Thr | Val | Glu | Arg | Met | Val | Ser | Pro | Ile | |
| | 645 | | | | 650 | | | | | 655 | | | | | | |
| GAG | AGC | GCT | GAA | GAC | TTA | GCC | AAG | CAG | ACT | GAA | ATT | GCA | TAT | GGG | ACC | 2191 |

| | | | | | | | | | | | | | | | | |
|---|---|---|---|---|---|---|---|---|---|---|---|---|---|---|---|---|
|Glu|Ser|Ala|Glu|Asp|Leu|Ala|Lys|Gln|Thr|Glu|Ile|Ala|Tyr|Gly|Thr| |
|660| | | |665| | | | |670| | | | |675| | |

```
CTG GAC TCT GGT TCA ACA AAA GAA TTT TTC AGA CGA TCC AAA ATT GCT      2239
Leu Asp Ser Gly Ser Thr Lys Glu Phe Phe Arg Arg Ser Lys Ile Ala
            680                 685                 690

GTG TAT GAG AAA ATG TGG TCT TAC ATG AAA TCC GCA GAG CCA TCT GTG      2287
Val Tyr Glu Lys Met Trp Ser Tyr Met Lys Ser Ala Glu Pro Ser Val
                695                 700                 705

TTT ACC AAA ACA ACA GCT GAC GGG GTA GCC CGA GTT CGG AAG TCC AAG      2335
Phe Thr Lys Thr Thr Ala Asp Gly Val Ala Arg Val Arg Lys Ser Lys
            710                 715                 720

GGA AAG TTC GCC TTC CTG CTG GAG TCG ACC ATG AAC GAG TAC ATT GAG      2383
Gly Lys Phe Ala Phe Leu Leu Glu Ser Thr Met Asn Glu Tyr Ile Glu
    725                 730                 735

CAG AGA AAG CCG TGC GAT ACG ATG AAA GTT GGT GGA AAT CTG GAT TCC      2431
Gln Arg Lys Pro Cys Asp Thr Met Lys Val Gly Gly Asn Leu Asp Ser
740                 745                 750                 755

AAA GGC TAT GGT GTG GCA ACC CCT AAA GGC TCA GCA TTA GGA AAT GCT      2479
Lys Gly Tyr Gly Val Ala Thr Pro Lys Gly Ser Ala Leu Gly Asn Ala
                760                 765                 770

GTT AAC CTG GCA GTA TTA AAA CTG AAT GAG CAA GGC CTC TTG GAC AAA      2527
Val Asn Leu Ala Val Leu Lys Leu Asn Glu Gln Gly Leu Leu Asp Lys
            775                 780                 785

TTG AAA AAC AAA TGG TGG TAC GAC AAA GGA GAG TGC GGC AGC GGG GGC      2575
Leu Lys Asn Lys Trp Trp Tyr Asp Lys Gly Glu Cys Gly Ser Gly Gly
    790                 795                 800

GGT GAC TCC AAG GAC AAG ACC AGT GCT CTA AGC CTG AGC AAT GTG GCA      2623
Gly Asp Ser Lys Asp Lys Thr Ser Ala Leu Ser Leu Ser Asn Val Ala
805                 810                 815

GGC GTG TTC TAT ATA CTT GTC GGA GGT CTG GGC CTG GCC ATG ATG GTG      2671
Gly Val Phe Tyr Ile Leu Val Gly Gly Leu Gly Leu Ala Met Met Val
820                 825                 830                 835

GCT TTG ATA GAA TTC TGT TAC AAA TCA CGG GCA GAG TCC AAA CGC ATG      2719
Ala Leu Ile Glu Phe Cys Tyr Lys Ser Arg Ala Glu Ser Lys Arg Met
                840                 845                 850

AAA CTC ACA AAG AAC ACC CAA AAC TTT AAG CCT GCT CCT GCC ACC AAC      2767
Lys Leu Thr Lys Asn Thr Gln Asn Phe Lys Pro Ala Pro Ala Thr Asn
            855                 860                 865

ACT CAG AAT TAC GCT ACA TAC AGA GAA GGC TAC AAC GTG TAT GGA ACA      2815
Thr Gln Asn Tyr Ala Thr Tyr Arg Glu Gly Tyr Asn Val Tyr Gly Thr
        870                 875                 880

GAA AGT GTT AAG ATC TAGGGATCCC TTCCACCAG AAGCATGCAA TGAGAGGAAA      2870
Glu Ser Val Lys Ile
        885

TCACTGAAAA CGTGGCTGCT TCAAGGATCC TGAGCCGGAT TTCACTCTCC CTGGTGTCGG    2930

GCATGACACG AATATTGCTG ATGGTGCAAT GACCTTTCAA TAGGAAAAAC TGATTTTTTT    2990

TTTCCTTCAG TGCCTTATGG AACACTCTGA GACTTGCGAC AATGCAAACC ATCATTGAAA    3050

TCTTTTTGCT TTGCTTGAAA AAAAAAAAA AAA                                  3083
```

( 2 ) INFORMATION FOR SEQ ID NO:6:

( i ) SEQUENCE CHARACTERISTICS:
        ( A ) LENGTH: 888 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Gly Gln Ser Val Leu Arg Ala Val Phe Phe Leu Val Leu Gly Leu

-continued

| 1 | | | | 5 | | | | | 10 | | | | | 15 | |
|---|---|---|---|---|---|---|---|---|---|---|---|---|---|---|---|

Leu Gly His Ser His Gly Gly Phe Pro Asn Thr Ile Ser Ile Gly Gly
                20                  25                  30

Leu Phe Met Arg Asn Thr Val Gln Glu His Ser Ala Phe Arg Phe Ala
            35                  40                  45

Val Gln Leu Tyr Asn Thr Asn Gln Asn Thr Thr Glu Lys Pro Phe His
        50                  55                  60

Leu Asn Tyr His Val Asp His Leu Asp Ser Ser Asn Ser Phe Ser Val
65                      70                  75                  80

Thr Asn Ala Phe Cys Ser Gln Phe Ser Arg Gly Val Tyr Ala Ile Phe
                85                  90                      95

Gly Phe Tyr Asp Gln Met Ser Met Asn Thr Leu Thr Ser Phe Cys Gly
            100                 105                 110

Ala Leu His Thr Ser Phe Val Thr Pro Ser Phe Pro Thr Asp Ala Asp
        115                 120                 125

Val Gln Phe Val Ile Gln Met Arg Pro Ala Leu Lys Gly Ala Ile Leu
        130                 135                 140

Ser Leu Leu Ser Tyr Tyr Lys Trp Glu Lys Phe Val Tyr Leu Tyr Asp
145                 150                 155                 160

Thr Glu Arg Gly Phe Ser Val Leu Gln Ala Ile Met Glu Ala Ala Val
            165                 170                 175

Gln Asn Asn Trp Gln Val Thr Ala Arg Ser Val Gly Asn Ile Lys Asp
            180                 185                 190

Val Gln Glu Phe Arg Arg Ile Ile Glu Glu Met Asp Arg Arg Gln Glu
        195                 200                 205

Lys Arg Tyr Leu Ile Asp Cys Glu Val Glu Arg Ile Asn Thr Ile Leu
    210                 215                 220

Glu Gln Val Val Ile Leu Gly Lys His Ser Arg Gly Tyr His Tyr Met
225                 230                 235                 240

Leu Ala Asn Leu Gly Phe Thr Asp Ile Leu Leu Glu Arg Val Met His
            245                 250                 255

Gly Gly Ala Asn Ile Thr Gly Phe Gln Ile Val Asn Asn Glu Asn Pro
            260                 265                 270

Met Val Gln Gln Phe Ile Gln Arg Trp Val Arg Leu Asp Glu Arg Glu
        275                 280                 285

Phe Pro Glu Ala Lys Asn Ala Pro Leu Lys Tyr Thr Ser Ala Leu Thr
    290                 295                 300

His Asp Ala Ile Leu Val Ile Ala Glu Ala Phe Arg Tyr Leu Arg Arg
305                 310                 315                 320

Gln Arg Val Asp Val Ser Arg Arg Gly Ser Ala Gly Asp Cys Leu Ala
            325                 330                 335

Asn Pro Ala Val Pro Trp Ser Gln Gly Ile Asp Ile Glu Arg Ala Leu
            340                 345                 350

Lys Met Val Gln Val Gln Gly Met Thr Gly Asn Ile Gln Phe Asp Thr
        355                 360                 365

Tyr Gly Arg Arg Thr Asn Tyr Thr Ile Asp Val Tyr Glu Met Lys Val
    370                 375                 380

Ser Gly Ser Arg Lys Ala Gly Tyr Trp Asn Glu Tyr Glu Arg Phe Val
385                 390                 395                 400

Pro Phe Ser Asp Gln Gln Ile Ser Asn Asp Ser Ser Ser Ser Glu Asn
            405                 410                 415

Arg Thr Ile Val Val Thr Thr Ile Leu Glu Ser Pro Tyr Val Met Tyr
            420                 425                 430

-continued

| | | | | | | | | | | | | | | |
|---|---|---|---|---|---|---|---|---|---|---|---|---|---|---|
| Lys | Lys | Asn | His | Glu | Gln | Leu | Glu | Gly | Asn | Glu | Arg | Tyr | Glu | Gly | Tyr |
| | 435 | | | | | 440 | | | | 445 | | | | |
| Cys | Val | Asp | Leu | Ala | Tyr | Glu | Ile | Ala | Lys | His | Val | Arg | Ile | Lys | Tyr |
| 450 | | | | | 455 | | | | | 460 | | | | |
| Lys | Leu | Ser | Ile | Val | Gly | Asp | Gly | Lys | Tyr | Gly | Ala | Arg | Asp | Pro | Glu |
| 465 | | | | 470 | | | | 475 | | | | | 480 | | |
| Thr | Lys | Ile | Trp | Asn | Gly | Met | Val | Gly | Glu | Leu | Val | Tyr | Gly | Arg | Ala |
| | | | 485 | | | | 490 | | | | | 495 | | | |
| Asp | Ile | Ala | Val | Ala | Pro | Leu | Thr | Ile | Thr | Leu | Val | Arg | Glu | Glu | Val |
| | | | 500 | | | | 505 | | | | | 510 | | | |
| Ile | Asp | Phe | Ser | Asn | Ala | Phe | Met | Ser | Leu | Gly | Ile | Ser | Ile | Met | Ile |
| | | 515 | | | | 520 | | | | | 525 | | | | |
| Lys | Lys | Pro | Gln | Lys | Ser | Lys | Pro | Gly | Val | Phe | Ser | Phe | Leu | Asp | Pro |
| | 530 | | | | 535 | | | | | 540 | | | | | |
| Leu | Ala | Tyr | Glu | Ile | Trp | Met | Cys | Ile | Val | Phe | Ala | Tyr | Ile | Gly | Val |
| 545 | | | | 550 | | | | | 555 | | | | | 560 | |
| Ser | Val | Val | Leu | Phe | Leu | Val | Ser | Arg | Phe | Ser | Pro | Tyr | Glu | Trp | His |
| | | | 565 | | | | | 570 | | | | | 575 | | |
| Leu | Glu | Asp | Asn | Asn | Glu | Glu | Pro | Arg | Asp | Pro | Gln | Ser | Pro | Pro | Asp |
| | | 580 | | | | 585 | | | | 590 | | | | | |
| Pro | Pro | Asn | Glu | Phe | Gly | Ile | Phe | Asn | Ser | Leu | Trp | Phe | Ser | Leu | Gly |
| | 595 | | | | | 600 | | | | | 605 | | | | |
| Ala | Phe | Met | Gln | Gln | Gly | Cys | Asp | Ile | Ser | Pro | Arg | Ser | Leu | Ser | Gly |
| 610 | | | | | 615 | | | | | 620 | | | | | |
| Arg | Ile | Val | Gly | Gly | Val | Trp | Trp | Phe | Phe | Thr | Leu | Ile | Ile | Ile | Ser |
| 625 | | | | 630 | | | | | 635 | | | | | 640 | |
| Ser | Tyr | Thr | Ala | Asn | Leu | Ala | Ala | Phe | Leu | Thr | Val | Glu | Arg | Met | Val |
| | | | 645 | | | | | 650 | | | | | 655 | | |
| Ser | Pro | Ile | Glu | Ser | Ala | Glu | Asp | Leu | Ala | Lys | Gln | Thr | Glu | Ile | Ala |
| | | 660 | | | | 665 | | | | | 670 | | | | |
| Tyr | Gly | Thr | Leu | Asp | Ser | Gly | Ser | Thr | Lys | Glu | Phe | Phe | Arg | Arg | Ser |
| | | 675 | | | | 680 | | | | 685 | | | | | |
| Lys | Ile | Ala | Val | Tyr | Glu | Lys | Met | Trp | Ser | Tyr | Met | Lys | Ser | Ala | Glu |
| 690 | | | | | 695 | | | | | 700 | | | | | |
| Pro | Ser | Val | Phe | Thr | Lys | Thr | Thr | Ala | Asp | Gly | Val | Ala | Arg | Val | Arg |
| 705 | | | | 710 | | | | | 715 | | | | | 720 | |
| Lys | Ser | Lys | Gly | Lys | Phe | Ala | Phe | Leu | Leu | Glu | Ser | Thr | Met | Asn | Glu |
| | | | 725 | | | | | 730 | | | | | 735 | | |
| Tyr | Ile | Glu | Gln | Arg | Lys | Pro | Cys | Asp | Thr | Met | Lys | Val | Gly | Gly | Asn |
| | | | 740 | | | | 745 | | | | | 750 | | | |
| Leu | Asp | Ser | Lys | Gly | Tyr | Gly | Val | Ala | Thr | Pro | Lys | Gly | Ser | Ala | Leu |
| | | 755 | | | | 760 | | | | | 765 | | | | |
| Gly | Asn | Ala | Val | Asn | Leu | Ala | Val | Leu | Lys | Leu | Asn | Glu | Gln | Gly | Leu |
| | 770 | | | | | 775 | | | | | 780 | | | | |
| Leu | Asp | Lys | Leu | Lys | Asn | Lys | Trp | Trp | Tyr | Asp | Lys | Gly | Glu | Cys | Gly |
| 785 | | | | | 790 | | | | | 795 | | | | | 800 |
| Ser | Gly | Gly | Gly | Asp | Ser | Lys | Asp | Lys | Thr | Ser | Ala | Leu | Ser | Leu | Ser |
| | | | | 805 | | | | 810 | | | | | 815 | | |
| Asn | Val | Ala | Gly | Val | Phe | Tyr | Ile | Leu | Val | Gly | Gly | Leu | Gly | Leu | Ala |
| | | | 820 | | | | | 825 | | | | | 830 | | |
| Met | Met | Val | Ala | Leu | Ile | Glu | Phe | Cys | Tyr | Lys | Ser | Arg | Ala | Glu | Ser |
| | | 835 | | | | | 840 | | | | | 845 | | | |
| Lys | Arg | Met | Lys | Leu | Thr | Lys | Asn | Thr | Gln | Asn | Phe | Lys | Pro | Ala | Pro |
| 850 | | | | | 855 | | | | | 860 | | | | | |

Ala Thr Asn Thr Gln Asn Tyr Ala Thr Tyr Arg Glu Gly Tyr Asn Val
865                 870                 875                 880

Tyr Gly Thr Glu Ser Val Lys Ile
            885

( 2 ) INFORMATION FOR SEQ ID NO:7:

( i ) SEQUENCE CHARACTERISTICS:
        ( A ) LENGTH: 2971 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: GluR4

( i x ) FEATURE:
        ( A ) NAME/KEY: CDS
        ( B ) LOCATION: 162..2870

( x i ) SEQUENCE DESCRIPTION: SEQ ID NO:7:

```
GTAATGGAGT  GTACGCAAAA  TCCTCTGTCT  GTGGACTCGC  ACCAGAGCCT  CCCAGAAAAC           60

CTGGGCGATC  TGCGCCATCG  TCTTCAATGC  CTCTCTGAAA  AGCCTTTAGC  AAGACTGAGA          120

GAAAGAGAAA  AGAGAGCGCG  CCAGAGAGAG  GAGCAAAGAA  G ATG AGG ATT ATT              173
                                                 Met Arg Ile Ile
                                                  1
```

```
TGC AGG CAG ATT GTC TTG TTG TTT TCT GGA TTT TGG GGA CTC GCC ATG              221
Cys Arg Gln Ile Val Leu Leu Phe Ser Gly Phe Trp Gly Leu Ala Met
 5               10                  15                  20

GGA GCC TTT CCA AGC AGC GTT CAA ATA GGT GGT CTC TTC ATC CGA AAC              269
Gly Ala Phe Pro Ser Ser Val Gln Ile Gly Gly Leu Phe Ile Arg Asn
             25                  30                  35

ACA GAC CAG GAA TAC ACT GCT TTT AGA CTG GCA ATC TTT CTT CAT AAC              317
Thr Asp Gln Glu Tyr Thr Ala Phe Arg Leu Ala Ile Phe Leu His Asn
         40                  45                  50

ACC AGC CCC AAT GCA TCG GAA GCT CCT TTC AAT TTG GTA CCT CAT GTG              365
Thr Ser Pro Asn Ala Ser Glu Ala Pro Phe Asn Leu Val Pro His Val
     55                  60                  65

GAC AAC ATT GAG ACT GCC AAC AGT TTT GCT GTG ACA AAC GCC TTC TGT              413
Asp Asn Ile Glu Thr Ala Asn Ser Phe Ala Val Thr Asn Ala Phe Cys
 70                  75                  80

TCC CAG TAT TCT AGA GGG GTG TTT GCC ATT TTT GGA CTC TAT GAC AAG              461
Ser Gln Tyr Ser Arg Gly Val Phe Ala Ile Phe Gly Leu Tyr Asp Lys
 85                  90                  95                 100

AGA TCC GTG CAT ACC TTG ACC TCG TTC TGC AGG CGT CTG CAC ATC TCT              509
Arg Ser Val His Thr Leu Thr Ser Phe Cys Arg Arg Leu His Ile Ser
             105                 110                 115

CTC ATC ACA CCA AGC TTT CCC ACT GAA GGG GAG AGC CAG TTT GTG CTG              557
Leu Ile Thr Pro Ser Phe Pro Thr Glu Gly Glu Ser Gln Phe Val Leu
         120                 125                 130

CAG CTA AGA CCT TCA CTG AGA GGT GCA CTC CTG AGC CTC CTG GAT CAC              605
Gln Leu Arg Pro Ser Leu Arg Gly Ala Leu Leu Ser Leu Leu Asp His
     135                 140                 145

TAT GAG TGG AAC TGT TTC GTC TTC CTG TAT GAT ACA GAC AGG GGG TAT              653
Tyr Glu Trp Asn Cys Phe Val Phe Leu Tyr Asp Thr Asp Arg Gly Tyr
 150                 155                 160

TCA ATA CTT CAA GCT ATA ATG GAA AAA GCA GGA CAA AAT GGA TGG CAT              701
Ser Ile Leu Gln Ala Ile Met Glu Lys Ala Gly Gln Asn Gly Trp His
165                 170                 175                 180

GTC AGT GCA ATA TGT GTG GAA AAT TTT AAT GAT GTC AGC TAC AGG CAA              749
```

|  |  |  |  |  |  |  |  |  |  |  |  |  |  |  |  |
|---|---|---|---|---|---|---|---|---|---|---|---|---|---|---|---|
| Val | Ser | Ala | Ile | Cys<br>185 | Val | Glu | Asn | Phe | Asn<br>190 | Asp | Val | Ser | Tyr | Arg<br>195 | Gln |

| CTG<br>Leu | CTA<br>Leu | GAA<br>Glu | GAG<br>Glu<br>200 | CTT<br>Leu | GAC<br>Asp | AGA<br>Arg | AGA<br>Arg | CAA<br>Gln<br>205 | GAG<br>Glu | AAG<br>Lys | AAA<br>Lys | TTT<br>Phe | GTG<br>Val<br>210 | ATA<br>Ile | GAT<br>Asp | 797 |

| TGT<br>Cys | GAG<br>Glu<br>215 | ATA<br>Ile | GAG<br>Glu | AGG<br>Arg | CTT<br>Leu | CAA<br>Gln | AAC<br>Asn<br>220 | ATT<br>Ile | TTA<br>Leu | GAA<br>Glu | CAA<br>Gln | ATT<br>Ile<br>225 | GTG<br>Val | AGT<br>Ser | GTT<br>Val | 845 |

| GGG<br>Gly | AAG<br>Lys<br>230 | CAT<br>His | GTC<br>Val | AAA<br>Lys | GGC<br>Gly | TAC<br>Tyr<br>235 | CAT<br>His | TAT<br>Tyr | ATC<br>Ile | ATC<br>Ile | GCA<br>Ala<br>240 | AAT<br>Asn | TTG<br>Leu | GGT<br>Gly | TTC<br>Phe | 893 |

| AAG<br>Lys<br>245 | GAT<br>Asp | ATT<br>Ile | TCT<br>Ser | CTT<br>Leu | GAG<br>Glu<br>250 | AGA<br>Arg | TTT<br>Phe | ATA<br>Ile | CAT<br>His | GGA<br>Gly<br>255 | GGA<br>Gly | GCA<br>Ala | AAT<br>Asn | GTA<br>Val | ACA<br>Thr<br>260 | 941 |

| GGA<br>Gly | TTC<br>Phe | CAG<br>Gln | TTG<br>Leu | GTA<br>Val<br>265 | GAT<br>Asp | TTT<br>Phe | AAT<br>Asn | ACA<br>Thr | CCC<br>Pro<br>270 | ATG<br>Met | GTA<br>Val | ACC<br>Thr | AAA<br>Lys | CTA<br>Leu<br>275 | ATG<br>Met | 989 |

| GAT<br>Asp | CGG<br>Arg | TGG<br>Trp | AAG<br>Lys<br>280 | AAA<br>Lys | CTA<br>Leu | GAT<br>Asp | CAG<br>Gln | AGA<br>Arg<br>285 | GAA<br>Glu | TAT<br>Tyr | CCA<br>Pro | GGT<br>Gly | TCT<br>Ser<br>290 | GAA<br>Glu | ACA<br>Thr | 1037 |

| CCT<br>Pro | CCA<br>Pro | AAG<br>Lys | TAC<br>Tyr<br>295 | ACC<br>Thr | TCT<br>Ser | GCT<br>Ala | CTC<br>Leu<br>300 | ACT<br>Thr | TAT<br>Tyr | GAT<br>Asp | GGA<br>Gly | GTC<br>Val<br>305 | CTG<br>Leu | GTG<br>Val | ATG<br>Met | 1085 |

| GCT<br>Ala | GAA<br>Glu<br>310 | ACT<br>Thr | TTC<br>Phe | CGA<br>Arg | AGT<br>Ser | CTC<br>Leu<br>315 | AGA<br>Arg | AGA<br>Arg | CAG<br>Gln | AAA<br>Lys | ATT<br>Ile<br>320 | GAT<br>Asp | ATT<br>Ile | TCA<br>Ser | AGG<br>Arg | 1133 |

| AGA<br>Arg<br>325 | GGA<br>Gly | AAT<br>Asn | GCT<br>Ala | GGG<br>Gly | GAC<br>Asp<br>330 | TGT<br>Cys | CTG<br>Leu | GCA<br>Ala | AAC<br>Asn | CCT<br>Pro<br>335 | GCT<br>Ala | GCT<br>Ala | CCC<br>Pro | TGG<br>Trp | GGC<br>Gly<br>340 | 1181 |

| CAG<br>Gln | GGA<br>Gly | ATT<br>Ile | GAC<br>Asp | ATG<br>Met<br>345 | GAG<br>Glu | AGG<br>Arg | ACA<br>Thr | CTG<br>Leu | AAG<br>Lys<br>350 | CAG<br>Gln | GTT<br>Val | CGA<br>Arg | ATT<br>Ile | CAA<br>Gln<br>355 | GGG<br>Gly | 1229 |

| CTG<br>Leu | ACT<br>Thr | GGG<br>Gly | AAT<br>Asn<br>360 | GTT<br>Val | CAA<br>Gln | TTT<br>Phe | GAC<br>Asp | CAT<br>His<br>365 | TAT<br>Tyr | GGA<br>Gly | CGT<br>Arg | AGA<br>Arg | GTT<br>Val<br>370 | AAT<br>Asn | TAC<br>Tyr | 1277 |

| ACA<br>Thr | ATG<br>Met | GAT<br>Asp<br>375 | GTG<br>Val | TTT<br>Phe | GAA<br>Glu | CTA<br>Leu | AAA<br>Lys<br>380 | AGC<br>Ser | ACA<br>Thr | GGA<br>Gly | CCT<br>Pro | CGA<br>Arg<br>385 | AAG<br>Lys | GTT<br>Val | GGC<br>Gly | 1325 |

| TAC<br>Tyr | TGG<br>Trp<br>390 | AAT<br>Asn | GAT<br>Asp | ATG<br>Met | GAT<br>Asp | AAA<br>Lys<br>395 | TTA<br>Leu | GTC<br>Val | TTG<br>Leu | ATT<br>Ile | CAA<br>Gln<br>400 | GAT<br>Asp | ATG<br>Met | CCT<br>Pro | ACT<br>Thr | 1373 |

| CTG<br>Leu<br>405 | GGC<br>Gly | AAT<br>Asn | GAC<br>Asp | ACA<br>Thr | GCA<br>Ala<br>410 | GCT<br>Ala | ATT<br>Ile | GAG<br>Glu | AAC<br>Asn | AGA<br>Arg<br>415 | ACA<br>Thr | GTG<br>Val | GTT<br>Val | GTA<br>Val | ACC<br>Thr<br>420 | 1421 |

| ACA<br>Thr | ATT<br>Ile | ATG<br>Met | GAA<br>Glu | TCT<br>Ser<br>425 | CCC<br>Pro | TAT<br>Tyr | GTT<br>Val | ATG<br>Met | TAC<br>Tyr<br>430 | AAG<br>Lys | AAA<br>Lys | AAT<br>Asn | CAT<br>His | GAA<br>Glu<br>435 | ATG<br>Met | 1469 |

| TTT<br>Phe | GAA<br>Glu | GGA<br>Gly | AAT<br>Asn<br>440 | GAC<br>Asp | AAG<br>Lys | TAC<br>Tyr | GAA<br>Glu | GGC<br>Gly<br>445 | TAC<br>Tyr | TGT<br>Cys | GTA<br>Val | GAT<br>Asp | CTG<br>Leu<br>450 | GCA<br>Ala | TCG<br>Ser | 1517 |

| GAA<br>Glu | AGT<br>Ser | GCA<br>Ala | AAA<br>Lys<br>455 | CAT<br>His | ATT<br>Ile | GGT<br>Gly | ATC<br>Ile<br>460 | AAA<br>Lys | TAT<br>Tyr | AAA<br>Lys | ATT<br>Ile<br>465 | GCC<br>Ala | ATT<br>Ile | GTT<br>Val | CCT<br>Pro | 1565 |

| GAT<br>Asp | GGA<br>Gly | AAA<br>Lys<br>470 | TAT<br>Tyr | GGA<br>Gly | GCA<br>Ala | AGG<br>Arg<br>475 | GAC<br>Asp | GCA<br>Ala | GAC<br>Asp | ACT<br>Thr | AAG<br>Lys<br>480 | ATC<br>Ile | TGG<br>Trp | AAT<br>Asn | GGG<br>Gly | 1613 |

| ATG<br>Met<br>485 | GTA<br>Val | GGA<br>Gly | GAG<br>Glu | CTT<br>Leu | GTG<br>Val<br>490 | TAT<br>Tyr | GGG<br>Gly | AAA<br>Lys | GCA<br>Ala | GAG<br>Glu<br>495 | ATT<br>Ile | GCT<br>Ala | ATT<br>Ile | GCC<br>Ala | CCT<br>Pro<br>500 | 1661 |

| CTG<br>Leu | ACA<br>Thr | ATC<br>Ile | ACA<br>Thr | TTG<br>Leu | GTT<br>Val | CGA<br>Arg | GAG<br>Glu | GAA<br>Glu | GTC<br>Val | ATC<br>Ile | GAT<br>Asp | TTT<br>Phe | TCT<br>Ser | AAG<br>Lys | CCT<br>Pro | 1709 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Leu | Thr | Ile | Thr | Leu | Val | Arg | Glu | Glu | Val | Ile | Asp | Phe | Ser | Lys | Pro |      |
|     |     |     |     | 505 |     |     |     | 510 |     |     |     |     |     | 515 |     |      |
| TTT | ATG | AGT | TTA | GGC | ATC | TCT | ATC | ATG | ATC | AAA | AAA | CCT | CAG | AAA | TCT | 1757 |
| Phe | Met | Ser | Leu | Gly | Ile | Ser | Ile | Met | Ile | Lys | Lys | Pro | Gln | Lys | Ser |      |
|     |     |     | 520 |     |     |     |     | 525 |     |     |     |     | 530 |     |     |      |
| AAA | CCA | GGA | GTC | TTT | TCC | TTC | TTG | GAC | CCT | CTG | GCC | TAT | GAG | ATC | TGG | 1805 |
| Lys | Pro | Gly | Val | Phe | Ser | Phe | Leu | Asp | Pro | Leu | Ala | Tyr | Glu | Ile | Trp |      |
|     |     | 535 |     |     |     |     | 540 |     |     |     |     | 545 |     |     |     |      |
| ATG | TGC | ATA | GTG | TTT | GCA | TAC | ATT | GGT | GTC | AGT | GTG | GTC | TTG | TTC | CTA | 1853 |
| Met | Cys | Ile | Val | Phe | Ala | Tyr | Ile | Gly | Val | Ser | Val | Val | Leu | Phe | Leu |      |
|     | 550 |     |     |     |     | 555 |     |     |     |     | 560 |     |     |     |     |      |
| GTC | AGT | AGG | TTT | AGC | CCA | TAT | GAG | TGG | CAC | ACA | GAA | GAA | CCT | GAG | GAT | 1901 |
| Val | Ser | Arg | Phe | Ser | Pro | Tyr | Glu | Trp | His | Thr | Glu | Glu | Pro | Glu | Asp |      |
| 565 |     |     |     |     | 570 |     |     |     |     | 575 |     |     |     |     | 580 |      |
| GGG | AAG | GAA | GGA | CCC | AGT | GAC | CAG | CCT | CCC | AAT | GAA | TTT | GGC | ATC | TTT | 1949 |
| Gly | Lys | Glu | Gly | Pro | Ser | Asp | Gln | Pro | Pro | Asn | Glu | Phe | Gly | Ile | Phe |      |
|     |     |     |     | 585 |     |     |     |     | 590 |     |     |     |     | 595 |     |      |
| AAC | AGC | CTT | TGG | TTT | TCC | CTG | GGT | GCC | TTT | ATG | CAA | CAA | GGA | TGT | GAC | 1997 |
| Asn | Ser | Leu | Trp | Phe | Ser | Leu | Gly | Ala | Phe | Met | Gln | Gln | Gly | Cys | Asp |      |
|     |     |     | 600 |     |     |     |     | 605 |     |     |     |     | 610 |     |     |      |
| ATT | TCA | CCC | AGA | TCC | CTG | TCA | GGT | CGG | ATT | GTT | GGA | GGC | GTG | TGG | TGG | 2045 |
| Ile | Ser | Pro | Arg | Ser | Leu | Ser | Gly | Arg | Ile | Val | Gly | Gly | Val | Trp | Trp |      |
|     |     | 615 |     |     |     |     | 620 |     |     |     |     | 625 |     |     |     |      |
| TTC | TTC | ACA | CTC | ATC | ATT | ATA | TCG | TCC | TAC | ACT | GCT | AAT | CTG | GCT | GCA | 2093 |
| Phe | Phe | Thr | Leu | Ile | Ile | Ile | Ser | Ser | Tyr | Thr | Ala | Asn | Leu | Ala | Ala |      |
|     |     | 630 |     |     |     |     | 635 |     |     |     |     | 640 |     |     |     |      |
| TTC | CTT | ACT | GTG | GAG | AGA | ATG | GTC | TCC | CCC | ATA | GAA | AGT | GCA | GAA | GAC | 2141 |
| Phe | Leu | Thr | Val | Glu | Arg | Met | Val | Ser | Pro | Ile | Glu | Ser | Ala | Glu | Asp |      |
| 645 |     |     |     |     | 650 |     |     |     |     | 655 |     |     |     |     | 660 |      |
| CTG | GCC | AAA | CAA | ACA | GAA | ATT | GCC | TAT | GGA | ACA | CTT | GAT | TCT | GGG | TCA | 2189 |
| Leu | Ala | Lys | Gln | Thr | Glu | Ile | Ala | Tyr | Gly | Thr | Leu | Asp | Ser | Gly | Ser |      |
|     |     |     |     | 665 |     |     |     |     | 670 |     |     |     |     | 675 |     |      |
| ACA | AAA | GAA | TTC | TTC | AGA | AGA | TCA | AAA | ATA | GCA | GTG | TAT | GAA | AAG | ATG | 2237 |
| Thr | Lys | Glu | Phe | Phe | Arg | Arg | Ser | Lys | Ile | Ala | Val | Tyr | Glu | Lys | Met |      |
|     |     |     |     | 680 |     |     |     |     | 685 |     |     |     |     | 690 |     |      |
| TGG | ACC | TAC | ATG | CGA | TCG | GCA | GAG | CCG | TCT | GTG | TTC | ACT | AGA | ACT | ACA | 2285 |
| Trp | Thr | Tyr | Met | Arg | Ser | Ala | Glu | Pro | Ser | Val | Phe | Thr | Arg | Thr | Thr |      |
|     |     |     |     | 695 |     |     |     |     | 700 |     |     |     |     | 705 |     |      |
| GCT | GAG | GGC | GTG | GCT | CGT | GTC | CGC | AAG | TCC | AAG | GGC | AAA | TTT | GCC | TTT | 2333 |
| Ala | Glu | Gly | Val | Ala | Arg | Val | Arg | Lys | Ser | Lys | Gly | Lys | Phe | Ala | Phe |      |
|     |     | 710 |     |     |     |     | 715 |     |     |     |     | 720 |     |     |     |      |
| CTC | CTG | GAG | TCC | ACG | ATG | AAT | GAA | TAC | ATT | GAG | CAG | CGA | AAG | CCC | TGT | 2381 |
| Leu | Leu | Glu | Ser | Thr | Met | Asn | Glu | Tyr | Ile | Glu | Gln | Arg | Lys | Pro | Cys |      |
| 725 |     |     |     |     | 730 |     |     |     |     | 735 |     |     |     |     | 740 |      |
| GAC | ACG | ATG | AAA | GTG | GGA | GGA | AAC | CTG | GAT | TCC | AAA | GGC | TAT | GGT | GTA | 2429 |
| Asp | Thr | Met | Lys | Val | Gly | Gly | Asn | Leu | Asp | Ser | Lys | Gly | Tyr | Gly | Val |      |
|     |     |     |     | 745 |     |     |     |     | 750 |     |     |     |     | 755 |     |      |
| GCA | ACG | CCC | AAG | GGT | TCC | TCA | TTA | AGA | ACT | CCT | GTA | AAC | CTT | GCC | GTT | 2477 |
| Ala | Thr | Pro | Lys | Gly | Ser | Ser | Leu | Arg | Thr | Pro | Val | Asn | Leu | Ala | Val |      |
|     |     |     | 760 |     |     |     |     | 765 |     |     |     |     | 770 |     |     |      |
| TTG | AAA | CTC | AGT | GAG | GCA | GGC | GTC | TTA | GAC | AAG | CTG | AAA | AAC | AAA | TGG | 2525 |
| Leu | Lys | Leu | Ser | Glu | Ala | Gly | Val | Leu | Asp | Lys | Leu | Lys | Asn | Lys | Trp |      |
|     |     | 775 |     |     |     |     | 780 |     |     |     |     | 785 |     |     |     |      |
| TGG | TAC | GAT | AAA | GGT | GAA | TGT | GGA | CCC | AAG | GAC | TCG | GGA | AGC | AAG | GAC | 2573 |
| Trp | Tyr | Asp | Lys | Gly | Glu | Cys | Gly | Pro | Lys | Asp | Ser | Gly | Ser | Lys | Asp |      |
|     | 790 |     |     |     |     | 795 |     |     |     |     | 800 |     |     |     |     |      |
| AAG | ACG | AGT | GCC | TTG | AGC | CTG | AGC | AAC | GTA | GCA | GGC | GTC | TTC | TAC | ATT | 2621 |
| Lys | Thr | Ser | Ala | Leu | Ser | Leu | Ser | Asn | Val | Ala | Gly | Val | Phe | Tyr | Ile |      |
| 805 |     |     |     |     | 810 |     |     |     |     | 815 |     |     |     |     | 820 |      |
| CTG | GTT | GGC | GGC | CTG | GGC | TTG | GCA | ATG | CTG | GTG | GCT | TTG | ATA | GAG | TTC | 2669 |

|     |     |     |     |     |     |     |     |     |     |     |     |     |     |     |       |
|-----|-----|-----|-----|-----|-----|-----|-----|-----|-----|-----|-----|-----|-----|-----|-------|
| Leu | Val | Gly | Gly | Leu | Gly | Leu | Ala | Met | Leu | Val | Ala | Leu | Ile | Glu | Phe   |
|     |     |     |     | 825 |     |     |     | 830 |     |     |     |     |     | 835 |       |

| TGT | TAC | AAG | TCC | AGG | GCA | GAG | GCG | AAG | AGA | ATG | AAG | CTG | ACT | TTT | TCC | 2717 |
|-----|-----|-----|-----|-----|-----|-----|-----|-----|-----|-----|-----|-----|-----|-----|-----|------|
| Cys | Tyr | Lys | Ser | Arg | Ala | Glu | Ala | Lys | Arg | Met | Lys | Leu | Thr | Phe | Ser |      |
|     |     |     | 840 |     |     |     |     | 845 |     |     |     |     | 850 |     |     |      |

| GAA | GCC | ATA | AGA | AAC | AAA | GCC | AGG | TTA | TCC | ATC | ACT | GGG | AGT | GTG | GGA | 2765 |
|-----|-----|-----|-----|-----|-----|-----|-----|-----|-----|-----|-----|-----|-----|-----|-----|------|
| Glu | Ala | Ile | Arg | Asn | Lys | Ala | Arg | Leu | Ser | Ile | Thr | Gly | Ser | Val | Gly |      |
|     |     |     | 855 |     |     |     | 860 |     |     |     |     | 865 |     |     |     |      |

| GAA | AAC | GGC | CGT | GTG | CTT | ACC | CCT | GAC | TGC | CCC | AAG | GCC | GTA | CAC | ACA | 2813 |
|-----|-----|-----|-----|-----|-----|-----|-----|-----|-----|-----|-----|-----|-----|-----|-----|------|
| Glu | Asn | Gly | Arg | Val | Leu | Thr | Pro | Asp | Cys | Pro | Lys | Ala | Val | His | Thr |      |
|     |     | 870 |     |     |     |     | 875 |     |     |     |     | 880 |     |     |     |      |

| GGA | ACT | GCA | ATT | AGA | CAA | AGT | TCG | GGA | TTG | GCT | GTC | ATT | GCA | TCG | GAC | 2861 |
|-----|-----|-----|-----|-----|-----|-----|-----|-----|-----|-----|-----|-----|-----|-----|-----|------|
| Gly | Thr | Ala | Ile | Arg | Gln | Ser | Ser | Gly | Leu | Ala | Val | Ile | Ala | Ser | Asp |      |
| 885 |     |     |     |     | 890 |     |     |     |     | 895 |     |     |     |     | 900 |      |

| CTA | CCA | TAAAAACCAA | AAAAATAATT | GAGTGCCTTA | ATCAAACTGT | GTTGGTGACT | 2917 |
|-----|-----|------------|------------|------------|------------|------------|------|
| Leu | Pro |            |            |            |            |            |      |

| GACTGAAACG | CAGCCCTGAG | GGAAAGGCCA | AGAGTGGGTC | TTGACTAAAT | CCAT | 2971 |

( 2 ) INFORMATION FOR SEQ ID NO:8:

( i ) SEQUENCE CHARACTERISTICS:
        ( A ) LENGTH: 902 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Arg | Ile | Ile | Cys | Arg | Gln | Ile | Val | Leu | Phe | Ser | Gly | Phe | Trp |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Gly | Leu | Ala | Met | Gly | Ala | Phe | Pro | Ser | Ser | Val | Gln | Ile | Gly | Gly | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Ile | Arg | Asn | Thr | Asp | Gln | Glu | Tyr | Thr | Ala | Phe | Arg | Leu | Ala | Ile |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Phe | Leu | His | Asn | Thr | Ser | Pro | Asn | Ala | Ser | Glu | Ala | Pro | Phe | Asn | Leu |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Val | Pro | His | Val | Asp | Asn | Ile | Glu | Thr | Ala | Asn | Ser | Phe | Ala | Val | Thr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Asn | Ala | Phe | Cys | Ser | Gln | Tyr | Ser | Arg | Gly | Val | Phe | Ala | Ile | Phe | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Tyr | Asp | Lys | Arg | Ser | Val | His | Thr | Leu | Thr | Ser | Phe | Cys | Arg | Arg |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | His | Ile | Ser | Leu | Ile | Thr | Pro | Ser | Phe | Pro | Thr | Glu | Gly | Glu | Ser |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Gln | Phe | Val | Leu | Gln | Leu | Arg | Pro | Ser | Leu | Arg | Gly | Ala | Leu | Leu | Ser |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Leu | Leu | Asp | His | Tyr | Glu | Trp | Asn | Cys | Phe | Val | Phe | Leu | Tyr | Asp | Thr |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asp | Arg | Gly | Tyr | Ser | Ile | Leu | Gln | Ala | Ile | Met | Glu | Lys | Ala | Gly | Gln |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asn | Gly | Trp | His | Val | Ser | Ala | Ile | Cys | Val | Glu | Asn | Phe | Asn | Asp | Val |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ser | Tyr | Arg | Gln | Leu | Leu | Glu | Glu | Leu | Asp | Arg | Arg | Gln | Glu | Lys | Lys |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Phe | Val | Ile | Asp | Cys | Glu | Ile | Glu | Arg | Leu | Gln | Asn | Ile | Leu | Glu | Gln |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Ile | Val | Ser | Val | Gly | Lys | His | Val | Lys | Gly | Tyr | His | Tyr | Ile | Ile | Ala |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| | | | | | | | | | | | | | | |
|---|---|---|---|---|---|---|---|---|---|---|---|---|---|---|
| Asn | Leu | Gly | Phe | Lys<br>245 | Asp | Ile | Ser | Leu<br>250 | Glu | Arg | Phe | Ile | His<br>255 | Gly | Gly |
| Ala | Asn | Val | Thr<br>260 | Gly | Phe | Gln | Leu | Val<br>265 | Asp | Phe | Asn | Thr<br>270 | Pro | Met | Val |
| Thr | Lys | Leu<br>275 | Met | Asp | Arg | Trp | Lys<br>280 | Lys | Leu | Asp | Gln | Arg<br>285 | Glu | Tyr | Pro |
| Gly | Ser<br>290 | Glu | Thr | Pro | Pro | Lys<br>295 | Tyr | Thr | Ser | Ala | Leu<br>300 | Thr | Tyr | Asp | Gly |
| Val<br>305 | Leu | Val | Met | Ala | Glu<br>310 | Thr | Phe | Arg | Ser | Leu<br>315 | Arg | Arg | Gln | Lys | Ile<br>320 |
| Asp | Ile | Ser | Arg | Arg<br>325 | Gly | Asn | Ala | Gly<br>330 | Asp | Cys | Leu | Ala | Asn<br>335 | Pro | Ala |
| Ala | Pro | Trp | Gly<br>340 | Gln | Gly | Ile | Asp | Met<br>345 | Glu | Arg | Thr | Leu<br>350 | Lys | Gln | Val |
| Arg | Ile | Gln<br>355 | Gly | Leu | Thr | Gly | Asn<br>360 | Val | Gln | Phe | Asp | His<br>365 | Tyr | Gly | Arg |
| Arg | Val<br>370 | Asn | Tyr | Thr | Met | Asp<br>375 | Val | Phe | Glu | Leu | Lys<br>380 | Ser | Thr | Gly | Pro |
| Arg<br>385 | Lys | Val | Gly | Tyr | Trp<br>390 | Asn | Asp | Met | Asp | Lys<br>395 | Leu | Val | Leu | Ile | Gln<br>400 |
| Asp | Met | Pro | Thr | Leu<br>405 | Gly | Asn | Asp | Thr | Ala<br>410 | Ala | Ile | Glu | Asn | Arg<br>415 | Thr |
| Val | Val | Val | Thr<br>420 | Thr | Ile | Met | Glu | Ser<br>425 | Pro | Tyr | Val | Met | Tyr<br>430 | Lys | Lys |
| Asn | His | Glu<br>435 | Met | Phe | Glu | Gly | Asn<br>440 | Asp | Lys | Tyr | Glu | Gly<br>445 | Tyr | Cys | Val |
| Asp | Leu<br>450 | Ala | Ser | Glu | Ser | Ala<br>455 | Lys | His | Ile | Gly | Ile<br>460 | Lys | Tyr | Lys | Ile |
| Ala<br>465 | Ile | Val | Pro | Asp | Gly<br>470 | Lys | Tyr | Gly | Ala | Arg<br>475 | Asp | Ala | Asp | Thr | Lys<br>480 |
| Ile | Trp | Asn | Gly | Met<br>485 | Val | Gly | Glu | Leu | Val<br>490 | Tyr | Gly | Lys | Ala | Glu<br>495 | Ile |
| Ala | Ile | Ala | Pro<br>500 | Leu | Thr | Ile | Thr | Leu<br>505 | Val | Arg | Glu | Glu | Val<br>510 | Ile | Asp |
| Phe | Ser | Lys<br>515 | Pro | Phe | Met | Ser | Leu<br>520 | Gly | Ile | Ser | Ile | Met<br>525 | Ile | Lys | Lys |
| Pro | Gln | Lys<br>530 | Ser | Lys | Pro | Gly<br>535 | Val | Phe | Ser | Phe | Leu<br>540 | Asp | Pro | Leu | Ala |
| Tyr<br>545 | Glu | Ile | Trp | Met | Cys<br>550 | Ile | Val | Phe | Ala | Tyr<br>555 | Ile | Gly | Val | Ser | Val<br>560 |
| Val | Leu | Phe | Leu | Val<br>565 | Ser | Arg | Phe | Ser | Pro<br>570 | Tyr | Glu | Trp | His | Thr<br>575 | Glu |
| Glu | Pro | Glu | Asp<br>580 | Gly | Lys | Glu | Gly | Pro<br>585 | Ser | Asp | Gln | Pro | Pro<br>590 | Asn | Glu |
| Phe | Gly | Ile<br>595 | Phe | Asn | Ser | Leu | Trp<br>600 | Phe | Ser | Leu | Gly | Ala<br>605 | Phe | Met | Gln |
| Gln | Gly | Cys<br>610 | Asp | Ile | Ser | Pro<br>615 | Arg | Ser | Leu | Ser | Gly<br>620 | Arg | Ile | Val | Gly |
| Gly<br>625 | Val | Trp | Trp | Phe | Phe<br>630 | Thr | Leu | Ile | Ile | Ile<br>635 | Ser | Ser | Tyr | Thr | Ala<br>640 |
| Asn | Leu | Ala | Ala | Phe<br>645 | Leu | Thr | Val | Glu | Arg<br>650 | Met | Val | Ser | Pro | Ile<br>655 | Glu |
| Ser | Ala | Glu | Asp | Leu | Ala | Lys | Gln | Thr | Glu | Ile | Ala | Tyr | Gly | Thr | Leu |

```
                    660                           665                           670
Asp  Ser  Gly  Ser  Thr  Lys  Glu  Phe  Phe  Arg  Arg  Ser  Lys  Ile  Ala  Val
              675                      680                      685

Tyr  Glu  Lys  Met  Trp  Thr  Tyr  Met  Arg  Ser  Ala  Glu  Pro  Ser  Val  Phe
         690                      695                      700

Thr  Arg  Thr  Thr  Ala  Glu  Gly  Val  Ala  Arg  Val  Arg  Lys  Ser  Lys  Gly
705                           710                      715                      720

Lys  Phe  Ala  Phe  Leu  Leu  Glu  Ser  Thr  Met  Asn  Glu  Tyr  Ile  Glu  Gln
                   725                      730                           735

Arg  Lys  Pro  Cys  Asp  Thr  Met  Lys  Val  Gly  Gly  Asn  Leu  Asp  Ser  Lys
              740                      745                      750

Gly  Tyr  Gly  Val  Ala  Thr  Pro  Lys  Gly  Ser  Ser  Leu  Arg  Thr  Pro  Val
         755                      760                      765

Asn  Leu  Ala  Val  Leu  Lys  Leu  Ser  Glu  Ala  Gly  Val  Leu  Asp  Lys  Leu
    770                       775                      780

Lys  Asn  Lys  Trp  Trp  Tyr  Asp  Lys  Gly  Glu  Cys  Gly  Pro  Lys  Asp  Ser
785                      790                      795                           800

Gly  Ser  Lys  Asp  Lys  Thr  Ser  Ala  Leu  Ser  Leu  Ser  Asn  Val  Ala  Gly
              805                      810                      815

Val  Phe  Tyr  Ile  Leu  Val  Gly  Gly  Leu  Gly  Leu  Ala  Met  Leu  Val  Ala
              820                      825                      830

Leu  Ile  Glu  Phe  Cys  Tyr  Lys  Ser  Arg  Ala  Glu  Ala  Lys  Arg  Met  Lys
         835                      840                      845

Leu  Thr  Phe  Ser  Glu  Ala  Ile  Arg  Asn  Lys  Ala  Arg  Leu  Ser  Ile  Thr
    850                      855                      860

Gly  Ser  Val  Gly  Glu  Asn  Gly  Arg  Val  Leu  Thr  Pro  Asp  Cys  Pro  Lys
865                      870                      875                           880

Ala  Val  His  Thr  Gly  Thr  Ala  Ile  Arg  Gln  Ser  Ser  Gly  Leu  Ala  Val
              885                      890                      895

Ile  Ala  Ser  Asp  Leu  Pro
              900
```

( 2 ) INFORMATION FOR SEQ ID NO:9:

( i ) SEQUENCE CHARACTERISTICS:
        ( A ) LENGTH: 3250 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: GluR5

( i x ) FEATURE:
        ( A ) NAME/KEY: CDS
        ( B ) LOCATION: 188..2950

( x i ) SEQUENCE DESCRIPTION: SEQ ID NO:9:

```
GGCTAGGAAG  CCCGCTTCAC  GTCCCCACGC  TTGTTCCCTC  CACCTCGCTC  TCCTGAGAGC      60

AGAGAGCGCG  CGGTGTGCAG  ACTCGGAGCA  TTCCGGGAGG  ATGAGGCGGG  GACCCAGCCC     120

AAGTTGGGTG  CATCTTGCGG  GCGTGAGGCC  ACAACTGGGT  TTCGGCATGA  ATTAAGAAGC     180

TTGAAAG  ATG  GAG  CGC  AGC  ACA  GTC  CTT  ATC  CAA  CCC  GGG  CTC  TGG  ACC     229
         Met  Glu  Arg  Ser  Thr  Val  Leu  Ile  Gln  Pro  Gly  Leu  Trp  Thr
          1                  5                       10

AGG  GAC  ACC  AGC  TGG  ACA  CTC  CTC  TAT  TTC  CTG  TGC  TAC  ATC  CTC  CCT     277
Arg  Asp  Thr  Ser  Trp  Thr  Leu  Leu  Tyr  Phe  Leu  Cys  Tyr  Ile  Leu  Pro
15                  20                       25                       30
```

| | | | | | | | | | | | | | | | | |
|---|---|---|---|---|---|---|---|---|---|---|---|---|---|---|---|---|
| CAG | ACC | TCC | CCT | CAA | GTG | CTC | AGG | ATC | GGA | GGG | ATT | TTT | GAA | ACT | GTG | 325 |
| Gln | Thr | Ser | Pro | Gln<br>35 | Val | Leu | Arg | Ile | Gly<br>40 | Gly | Ile | Phe | Glu | Thr<br>45 | Val | |
| GAA | AAT | GAA | CCT | GTT | AAT | GTT | GAA | GAA | TTA | GCT | TTC | AAG | TTT | GCA | GTC | 373 |
| Glu | Asn | Glu | Pro<br>50 | Val | Asn | Val | Glu | Glu<br>55 | Leu | Ala | Phe | Lys | Phe<br>60 | Ala | Val | |
| ACC | AGT | ATT | AAC | CGA | AAC | CGA | ACC | TTG | ATG | CCC | AAT | ACC | ACA | TTA | ACC | 421 |
| Thr | Ser | Ile<br>65 | Asn | Arg | Asn | Arg | Thr<br>70 | Leu | Met | Pro | Asn | Thr<br>75 | Thr | Leu | Thr | |
| TAT | GAC | ATC | CAG | AGA | ATT | AAT | CTT | TTT | GAT | AGT | TTT | GAA | GCC | TCC | CGA | 469 |
| Tyr | Asp<br>80 | Ile | Gln | Arg | Ile | Asn<br>85 | Leu | Phe | Asp | Ser | Phe<br>90 | Glu | Ala | Ser | Arg | |
| AGA | GCA | TGC | GAC | CAG | CTG | GCT | CTC | GGG | GTG | GCC | GCA | CTC | TTC | GGC | CCT | 517 |
| Arg<br>95 | Ala | Cys | Asp | Gln | Leu<br>100 | Ala | Leu | Gly | Val | Ala<br>105 | Ala | Leu | Phe | Gly | Pro<br>110 | |
| TCC | CAC | AGC | TCC | TCC | GTC | AGT | GCT | GTA | CAG | TCT | ATT | TGC | AAT | GCT | CTG | 565 |
| Ser | His | Ser | Ser | Ser<br>115 | Val | Ser | Ala | Val | Gln<br>120 | Ser | Ile | Cys | Asn | Ala<br>125 | Leu | |
| GAA | GTT | CCA | CAC | ATT | CAG | ACT | CGC | TGG | AAA | CAC | CCT | TCC | GTG | GAC | AGC | 613 |
| Glu | Val | Pro | His<br>130 | Ile | Gln | Thr | Arg | Trp<br>135 | Lys | His | Pro | Ser | Val<br>140 | Asp | Ser | |
| AGA | GAC | CTA | TTT | TAT | ATC | AAC | CTC | TAC | CCG | GAC | TAT | GCG | GCT | ATC | AGC | 661 |
| Arg | Asp | Leu<br>145 | Phe | Tyr | Ile | Asn | Leu<br>150 | Tyr | Pro | Asp | Tyr | Ala<br>155 | Ala | Ile | Ser | |
| AGG | GCG | GTC | CTG | GAT | TTG | GTC | CTC | TAT | TAC | AAC | TGG | AAA | ACA | GTG | ACG | 709 |
| Arg | Ala<br>160 | Val | Leu | Asp | Leu | Val<br>165 | Leu | Tyr | Tyr | Asn | Trp<br>170 | Lys | Thr | Val | Thr | |
| GTG | GTG | TAT | GAA | GAT | AGC | ACA | GGT | CTA | ATT | CGT | CTG | CAA | GAG | CTC | ATC | 757 |
| Val<br>175 | Val | Tyr | Glu | Asp | Ser<br>180 | Thr | Gly | Leu | Ile | Arg<br>185 | Leu | Gln | Glu | Leu | Ile<br>190 | |
| AAA | GCT | CCC | TCC | AGA | TAC | AAC | ATT | AAA | ATC | AAA | ATC | CGC | CAG | CTT | CCC | 805 |
| Lys | Ala | Pro | Ser | Arg<br>195 | Tyr | Asn | Ile | Lys | Ile<br>200 | Lys | Ile | Arg | Gln | Leu<br>205 | Pro | |
| CCT | GCG | AAT | AAA | GAC | GCC | AAA | CCT | CTG | CTC | AAG | GAG | ATG | AAG | AAA | AGC | 853 |
| Pro | Ala | Asn | Lys<br>210 | Asp | Ala | Lys | Pro | Leu<br>215 | Leu | Lys | Glu | Met | Lys<br>220 | Lys | Ser | |
| AAA | GAG | TTC | TAT | GTG | ATA | TTT | GAT | TGT | TCG | CAC | GAA | ACA | GCT | GCG | GAA | 901 |
| Lys | Glu | Phe<br>225 | Tyr | Val | Ile | Phe | Asp<br>230 | Cys | Ser | His | Glu | Thr<br>235 | Ala | Ala | Glu | |
| ATT | CTT | AAG | CAG | ATT | TTG | TTC | ATG | GGC | ATG | ATG | ACT | GAA | TAT | TAT | CAC | 949 |
| Ile | Leu<br>240 | Lys | Gln | Ile | Leu | Phe<br>245 | Met | Gly | Met | Met | Thr<br>250 | Glu | Tyr | Tyr | His | |
| TAC | TTC | TTC | ACA | ACC | CTG | GAC | TTG | TTT | GCT | TTA | GAT | CTG | GAA | CTC | TAT | 997 |
| Tyr<br>255 | Phe | Phe | Thr | Thr | Leu<br>260 | Asp | Leu | Phe | Ala | Leu<br>265 | Asp | Leu | Glu | Leu | Tyr<br>270 | |
| AGG | TAC | AGC | GGT | GTA | AAT | ATG | ACT | GGA | TTT | CGG | TTG | CTG | AAT | ATT | GAC | 1045 |
| Arg | Tyr | Ser | Gly | Val<br>275 | Asn | Met | Thr | Gly | Phe<br>280 | Arg | Leu | Leu | Asn | Ile<br>285 | Asp | |
| AAC | CCT | CAC | GTG | TCA | TCC | ATC | ATT | GAG | AAG | TGG | TCC | ATG | GAG | AGG | TTG | 1093 |
| Asn | Pro | His | Val<br>290 | Ser | Ser | Ile | Ile | Glu<br>295 | Lys | Trp | Ser | Met | Glu<br>300 | Arg | Leu | |
| CAG | GCC | CCG | CCC | AGA | CCC | GAG | ACT | GGT | CTT | CTG | GAT | GGC | ATG | ATG | ACA | 1141 |
| Gln | Ala | Pro<br>305 | Pro | Arg | Pro | Glu | Thr<br>310 | Gly | Leu | Leu | Asp | Gly<br>315 | Met | Met | Thr | |
| ACT | GAA | GCA | GCG | CTG | ATG | TAC | GAT | GCT | GTG | TAC | ATG | GTA | GCC | ATT | GCG | 1189 |
| Thr | Glu | Ala<br>320 | Ala | Leu | Met | Tyr | Asp<br>325 | Ala | Val | Tyr | Met | Val<br>330 | Ala | Ile | Ala | |
| TCC | CAC | CGT | GCC | TCT | CAG | CTG | ACC | GTC | AGC | TCC | CTG | CAG | TGC | CAT | CGA | 1237 |
| Ser<br>335 | His | Arg | Ala | Ser | Gln<br>340 | Leu | Thr | Val | Ser | Ser<br>345 | Leu | Gln | Cys | His | Arg<br>350 | |

```
CAT AAG CCA TGG CGC CTT GGA CCC AGA TTT ATG AAC CTC ATC AAA GAG    1285
His Lys Pro Trp Arg Leu Gly Pro Arg Phe Met Asn Leu Ile Lys Glu
            355                 360                 365

GCT CGG TGG GAC GGC TTG ACT GGG CGG ATC ACC TTC AAT AAG ACC GAT    1333
Ala Arg Trp Asp Gly Leu Thr Gly Arg Ile Thr Phe Asn Lys Thr Asp
            370                 375                 380

GGC TTG AGA AAG GAT TTT GAC CTG GAC ATT ATC AGT CTC AAA GAG GAA    1381
Gly Leu Arg Lys Asp Phe Asp Leu Asp Ile Ile Ser Leu Lys Glu Glu
            385                 390                 395

GGA ACT GAA AAG GCC TCT GGT GAA GTG TCT AAA CAC TTG TAT AAA GTG    1429
Gly Thr Glu Lys Ala Ser Gly Glu Val Ser Lys His Leu Tyr Lys Val
        400                 405                 410

TGG AAG AAG ATT GGG ATT TGG AAC TCC AAC AGT GGG CTG AAC ATG ACG    1477
Trp Lys Lys Ile Gly Ile Trp Asn Ser Asn Ser Gly Leu Asn Met Thr
415                 420                 425                 430

GAT GGC AAC AGA GAC AGG TCC AAC AAT ATC ACG GAC TCG CTG GCT AAC    1525
Asp Gly Asn Arg Asp Arg Ser Asn Asn Ile Thr Asp Ser Leu Ala Asn
            435                 440                 445

CGC ACA CTC ATT GTC ACC ACT ATT CTG GAA GAG CCC TAC GTG ATG TAC    1573
Arg Thr Leu Ile Val Thr Thr Ile Leu Glu Glu Pro Tyr Val Met Tyr
            450                 455                 460

AGG AAA TCC GAT AAG CCC TTG TAT GGA AAC GAC AGG TTT GAA GGA TAT    1621
Arg Lys Ser Asp Lys Pro Leu Tyr Gly Asn Asp Arg Phe Glu Gly Tyr
            465                 470                 475

TGC CTG GAT CTG CTG AAA GAA CTG TCC AAT ATC CTG GGT TTT CTT TAC    1669
Cys Leu Asp Leu Leu Lys Glu Leu Ser Asn Ile Leu Gly Phe Leu Tyr
            480                 485                 490

GAT GTT AAA CTG GTT CCT GAT GGC AAA TAT GGA GCA CAG AAT GAC AAA    1717
Asp Val Lys Leu Val Pro Asp Gly Lys Tyr Gly Ala Gln Asn Asp Lys
495                 500                 505                 510

GGG GAA TGG AAT GGG ATG GTA AAA GAA CTC ATC GAC CAC AGA GCT GAC    1765
Gly Glu Trp Asn Gly Met Val Lys Glu Leu Ile Asp His Arg Ala Asp
            515                 520                 525

CTG GCA GTG GCC CCT CTC ACC ATC ACA TAC GTA CGG GAG AAA GTC ATT    1813
Leu Ala Val Ala Pro Leu Thr Ile Thr Tyr Val Arg Glu Lys Val Ile
            530                 535                 540

GAC TTC TCC AAG CCC TTC ATG ACC CTG GGC ATT AGC ATC CTT TAC CGG    1861
Asp Phe Ser Lys Pro Phe Met Thr Leu Gly Ile Ser Ile Leu Tyr Arg
            545                 550                 555

AAG CCC AAT GGA ACC AAC CCG GGT GTC TTC TCC TTC CTC AAC CCC CTA    1909
Lys Pro Asn Gly Thr Asn Pro Gly Val Phe Ser Phe Leu Asn Pro Leu
            560                 565                 570

TCT CCG GAC ATT TGG ATG TAC GTG CTG CTC GCC TGC CTA GGA GTC AGT    1957
Ser Pro Asp Ile Trp Met Tyr Val Leu Leu Ala Cys Leu Gly Val Ser
575                 580                 585                 590

TGT GTA CTG TTT GTG ATT GCG AGG TTC ACA CCC TAC GAG TGG TAT AAC    2005
Cys Val Leu Phe Val Ile Ala Arg Phe Thr Pro Tyr Glu Trp Tyr Asn
            595                 600                 605

CCC CAC CCA TGC AAC CCC GAC TCA GAC GTG GTG GAA AAC AAT TTC ACT    2053
Pro His Pro Cys Asn Pro Asp Ser Asp Val Val Glu Asn Asn Phe Thr
            610                 615                 620

TTG CTA AAT AGT TTC TGG TTT GGA GTT GGA GCT CTC ATG CAG CAA GGA    2101
Leu Leu Asn Ser Phe Trp Phe Gly Val Gly Ala Leu Met Gln Gln Gly
            625                 630                 635

TCA GAG CTG ATG CCC AAG GCT CTA TCG ACC AGA ATA GTT GGA GGA ATA    2149
Ser Glu Leu Met Pro Lys Ala Leu Ser Thr Arg Ile Val Gly Gly Ile
        640                 645                 650

TGG TGG TTT TTC ACC CTA ATC ATC ATT TCA TCC TAC ACG GCC AAC CTG    2197
Trp Trp Phe Phe Thr Leu Ile Ile Ile Ser Ser Tyr Thr Ala Asn Leu
655                 660                 665                 670
```

| | | | | | | | | | | | | | | | | |
|---|---|---|---|---|---|---|---|---|---|---|---|---|---|---|---|---|
| GCT | GCC | TTC | TTG | ACG | GTA | GAA | AGA | ATG | GAA | TCC | CCC | ATC | GAT | TCC | GCA | 2245 |
| Ala | Ala | Phe | Leu | Thr | Val | Glu | Arg | Met | Glu | Ser | Pro | Ile | Asp | Ser | Ala | |
| | | | | 675 | | | | 680 | | | | | | 685 | | |
| GAC | GAT | CTG | GCC | AAA | CAA | ACC | AAG | ATA | GAA | TAT | GGG | GCA | GTC | AGA | GAT | 2293 |
| Asp | Asp | Leu | Ala | Lys | Gln | Thr | Lys | Ile | Glu | Tyr | Gly | Ala | Val | Arg | Asp | |
| | | | | 690 | | | | 695 | | | | 700 | | | | |
| GGC | TCG | ACG | ATG | ACC | TTC | TTC | AAG | AAA | TCA | AAG | ATC | TCC | ACC | TAT | GAG | 2341 |
| Gly | Ser | Thr | Met | Thr | Phe | Phe | Lys | Lys | Ser | Lys | Ile | Ser | Thr | Tyr | Glu | |
| | | 705 | | | | | 710 | | | | | 715 | | | | |
| AAA | ATG | TGG | GCT | TTC | ATG | AGC | AGT | AGA | CAG | CAG | AGC | GCA | CTG | GTT | AAA | 2389 |
| Lys | Met | Trp | Ala | Phe | Met | Ser | Ser | Arg | Gln | Gln | Ser | Ala | Leu | Val | Lys | |
| | | 720 | | | | | 725 | | | | | 730 | | | | |
| AAC | AGT | GAC | GAG | GGG | ATC | CAA | AGG | GTG | CTC | ACC | ACC | GAC | TAC | GCA | CTG | 2437 |
| Asn | Ser | Asp | Glu | Gly | Ile | Gln | Arg | Val | Leu | Thr | Thr | Asp | Tyr | Ala | Leu | |
| 735 | | | | | 740 | | | | | 745 | | | | | 750 | |
| CTG | ATG | GAG | TCC | ACC | AGC | ATT | GAG | TAT | GTG | ACG | CAG | AGG | AAC | TGC | AAC | 2485 |
| Leu | Met | Glu | Ser | Thr | Ser | Ile | Glu | Tyr | Val | Thr | Gln | Arg | Asn | Cys | Asn | |
| | | | | 755 | | | | | 760 | | | | | 765 | | |
| CTC | ACT | CAG | ATC | GGG | GGC | CTC | ATA | GAC | TCC | AAA | GGC | TAT | GGA | GTG | GGG | 2533 |
| Leu | Thr | Gln | Ile | Gly | Gly | Leu | Ile | Asp | Ser | Lys | Gly | Tyr | Gly | Val | Gly | |
| | | | 770 | | | | | 775 | | | | | 780 | | | |
| ACG | CCT | ATC | GGC | TCC | CCT | TAC | CGG | GAT | AAA | ATT | ACG | ATT | GCC | ATT | CTT | 2581 |
| Thr | Pro | Ile | Gly | Ser | Pro | Tyr | Arg | Asp | Lys | Ile | Thr | Ile | Ala | Ile | Leu | |
| | | 785 | | | | | 790 | | | | | 795 | | | | |
| CAA | CTG | CAA | GAA | GAA | GGG | AAG | CTT | CAT | ATG | ATG | AAA | GAG | AAG | TGG | TGG | 2629 |
| Gln | Leu | Gln | Glu | Glu | Gly | Lys | Leu | His | Met | Met | Lys | Glu | Lys | Trp | Trp | |
| | 800 | | | | | 805 | | | | | 810 | | | | | |
| AGG | GGG | AAT | GGC | TGC | CCT | GAA | GAA | GAC | AGT | AAG | GAA | GCC | AGT | GCT | CTG | 2677 |
| Arg | Gly | Asn | Gly | Cys | Pro | Glu | Glu | Asp | Ser | Lys | Glu | Ala | Ser | Ala | Leu | |
| 815 | | | | | 820 | | | | | 825 | | | | | 830 | |
| GGA | GTG | GAA | AAT | ATC | GGC | GGC | ATC | TTC | ATT | GTT | CTG | GCT | GCA | GGA | CTC | 2725 |
| Gly | Val | Glu | Asn | Ile | Gly | Gly | Ile | Phe | Ile | Val | Leu | Ala | Ala | Gly | Leu | |
| | | | | 835 | | | | | 840 | | | | | 845 | | |
| GTG | CTT | TCT | GTG | TTT | GTA | GCC | ATT | GGA | GAA | TTT | TTA | TAC | AAA | TCA | CGG | 2773 |
| Val | Leu | Ser | Val | Phe | Val | Ala | Ile | Gly | Glu | Phe | Leu | Tyr | Lys | Ser | Arg | |
| | | | 850 | | | | | 855 | | | | | 860 | | | |
| AAG | AAC | AAT | GAC | GTT | GAG | CAG | TGT | CTC | TCT | TTC | AAT | GCC | ATC | ATG | GAA | 2821 |
| Lys | Asn | Asn | Asp | Val | Glu | Gln | Cys | Leu | Ser | Phe | Asn | Ala | Ile | Met | Glu | |
| | | 865 | | | | | 870 | | | | | 875 | | | | |
| GAG | CTG | GGA | ATA | TCC | CTC | AAG | AAT | CAG | AAA | AAA | TTA | AAG | AAA | AAG | TCA | 2869 |
| Glu | Leu | Gly | Ile | Ser | Leu | Lys | Asn | Gln | Lys | Lys | Leu | Lys | Lys | Lys | Ser | |
| | 880 | | | | | 885 | | | | | 890 | | | | | |
| AGA | ACT | AAG | GGC | AAA | TCT | TCT | TTC | ACA | AGT | ATC | CTT | ACT | TGT | CAC | CAG | 2917 |
| Arg | Thr | Lys | Gly | Lys | Ser | Ser | Phe | Thr | Ser | Ile | Leu | Thr | Cys | His | Gln | |
| 895 | | | | | 900 | | | | | 905 | | | | | 910 | |
| AGA | CGA | ACT | CAG | AGA | AAA | GAG | ACA | GTG | GCG | TGATCAAAGA | | ACACACCTGT | | | | 2967 |
| Arg | Arg | Thr | Gln | Arg | Lys | Glu | Thr | Val | Ala | | | | | | | |
| | | | | 915 | | | | | 920 | | | | | | | |

| | | | | |
|---|---|---|---|---|
| AAGAAGAAAA | AGCCCACACG | TCCGCTGCAC | ATATTTGGAG | GACAGATTTC | AGAGGACTAT | 3027 |
| GTCTTTATCC | ATAACCCCAG | TCGTGGACAG | AGGGGGAAGA | AATGCACAAT | TTTTAAAGCT | 3087 |
| CACATAGATA | TTACTTGAGA | AGTGAAACTG | ATTCTTTTCA | GATGAATTTG | TATGCACACT | 3147 |
| TATTTTGAAT | TTTTCCATTT | CCTCCGATAA | ATTGCTATGT | GTGCTTTCTA | AATAATAATA | 3207 |
| AACAAGCGGA | CTTTGTTTTT | CATAAAAAAA | AAAAAAAAAA | AAA | | 3250 |

( 2 ) INFORMATION FOR SEQ ID NO:10:

( i ) SEQUENCE CHARACTERISTICS:
( A ) LENGTH: 920 amino acids ( B ) TYPE: amino acid
( D ) TOPOLOGY: linear ( i i ) MOLECULE TYPE: protein ( x i ) SEQUENCE DESCRIPTION: SEQ ID NO:10:

| Met | Glu | Arg | Ser | Thr | Val | Leu | Ile | Gln | Pro | Gly | Leu | Trp | Thr | Arg | Asp |
|---|---|---|---|---|---|---|---|---|---|---|---|---|---|---|---|
| 1 | | | | 5 | | | | | 10 | | | | | 15 | |

| Thr | Ser | Trp | Thr | Leu | Leu | Tyr | Phe | Leu | Cys | Tyr | Ile | Leu | Pro | Gln | Thr |
| | | | 20 | | | | 25 | | | | | | 30 | | |

| Ser | Pro | Gln | Val | Leu | Arg | Ile | Gly | Gly | Ile | Phe | Glu | Thr | Val | Glu | Asn |
| | | | 35 | | | | 40 | | | | | 45 | | | |

| Glu | Pro | Val | Asn | Val | Glu | Glu | Leu | Ala | Phe | Lys | Phe | Ala | Val | Thr | Ser |
| | 50 | | | | | 55 | | | | | 60 | | | | |

| Ile | Asn | Arg | Asn | Arg | Thr | Leu | Met | Pro | Asn | Thr | Thr | Leu | Thr | Tyr | Asp |
| 65 | | | | | 70 | | | | | 75 | | | | | 80 |

| Ile | Gln | Arg | Ile | Asn | Leu | Phe | Asp | Ser | Phe | Glu | Ala | Ser | Arg | Arg | Ala |
| | | | | 85 | | | | | 90 | | | | | 95 | |

| Cys | Asp | Gln | Leu | Ala | Leu | Gly | Val | Ala | Ala | Leu | Phe | Gly | Pro | Ser | His |
| | | | 100 | | | | 105 | | | | | 110 | | | |

| Ser | Ser | Ser | Val | Ser | Ala | Val | Gln | Ser | Ile | Cys | Asn | Ala | Leu | Glu | Val |
| | | 115 | | | | | 120 | | | | | 125 | | | |

| Pro | His | Ile | Gln | Thr | Arg | Trp | Lys | His | Pro | Ser | Val | Asp | Ser | Arg | Asp |
| | 130 | | | | | 135 | | | | | 140 | | | | |

| Leu | Phe | Tyr | Ile | Asn | Leu | Tyr | Pro | Asp | Tyr | Ala | Ala | Ile | Ser | Arg | Ala |
| 145 | | | | | 150 | | | | | 155 | | | | | 160 |

| Val | Leu | Asp | Leu | Val | Leu | Tyr | Tyr | Asn | Trp | Lys | Thr | Val | Thr | Val | Val |
| | | | | 165 | | | | | 170 | | | | | 175 | |

| Tyr | Glu | Asp | Ser | Thr | Gly | Leu | Ile | Arg | Leu | Gln | Glu | Leu | Ile | Lys | Ala |
| | | | | 180 | | | | | 185 | | | | | 190 | |

| Pro | Ser | Arg | Tyr | Asn | Ile | Lys | Ile | Lys | Ile | Arg | Gln | Leu | Pro | Pro | Ala |
| | | 195 | | | | | 200 | | | | | 205 | | | |

| Asn | Lys | Asp | Ala | Lys | Pro | Leu | Leu | Lys | Glu | Met | Lys | Lys | Ser | Lys | Glu |
| | 210 | | | | | 215 | | | | | 220 | | | | |

| Phe | Tyr | Val | Ile | Phe | Asp | Cys | Ser | His | Glu | Thr | Ala | Ala | Glu | Ile | Leu |
| 225 | | | | | 230 | | | | | 235 | | | | | 240 |

| Lys | Gln | Ile | Leu | Phe | Met | Gly | Met | Met | Thr | Glu | Tyr | Tyr | His | Tyr | Phe |
| | | | | 245 | | | | | 250 | | | | | 255 | |

| Phe | Thr | Thr | Leu | Asp | Leu | Phe | Ala | Leu | Asp | Leu | Glu | Leu | Tyr | Arg | Tyr |
| | | | 260 | | | | | 265 | | | | | 270 | | |

| Ser | Gly | Val | Asn | Met | Thr | Gly | Phe | Arg | Leu | Leu | Asn | Ile | Asp | Asn | Pro |
| | | 275 | | | | | 280 | | | | | 285 | | | |

| His | Val | Ser | Ser | Ile | Ile | Glu | Lys | Trp | Ser | Met | Glu | Arg | Leu | Gln | Ala |
| | 290 | | | | | 295 | | | | | 300 | | | | |

| Pro | Pro | Arg | Pro | Glu | Thr | Gly | Leu | Leu | Asp | Gly | Met | Met | Thr | Thr | Glu |
| 305 | | | | | 310 | | | | | 315 | | | | | 320 |

| Ala | Ala | Leu | Met | Tyr | Asp | Ala | Val | Tyr | Met | Val | Ala | Ile | Ala | Ser | His |
| | | | | 325 | | | | | 330 | | | | | 335 | |

| Arg | Ala | Ser | Gln | Leu | Thr | Val | Ser | Ser | Leu | Gln | Cys | His | Arg | His | Lys |
| | | | 340 | | | | | 345 | | | | | 350 | | |

| Pro | Trp | Arg | Leu | Gly | Pro | Arg | Phe | Met | Asn | Leu | Ile | Lys | Glu | Ala | Arg |
| | | 355 | | | | | 360 | | | | | 365 | | | |

| Trp | Asp | Gly | Leu | Thr | Gly | Arg | Ile | Thr | Phe | Asn | Lys | Thr | Asp | Gly | Leu |
| | 370 | | | | | 375 | | | | | 380 | | | | |

| Arg | Lys | Asp | Phe | Asp | Leu | Asp | Ile | Ile | Ser | Leu | Lys | Glu | Glu | Gly | Thr |

|  |  |  |  |  |  |  |  |  |  |  |  |  |  |  |  |
|---|---|---|---|---|---|---|---|---|---|---|---|---|---|---|---|

385 390 395 400

Glu Lys Ala Ser Gly Glu Val Ser Lys His Leu Tyr Lys Val Trp Lys
                405                    410                    415

Lys Ile Gly Ile Trp Asn Ser Asn Ser Gly Leu Asn Met Thr Asp Gly
                420                    425                    430

Asn Arg Asp Arg Ser Asn Asn Ile Thr Asp Ser Leu Ala Asn Arg Thr
                435                    440                    445

Leu Ile Val Thr Thr Ile Leu Glu Glu Pro Tyr Val Met Tyr Arg Lys
                450                    455                    460

Ser Asp Lys Pro Leu Tyr Gly Asn Asp Arg Phe Glu Gly Tyr Cys Leu
465                 470                    475                    480

Asp Leu Leu Lys Glu Leu Ser Asn Ile Leu Gly Phe Leu Tyr Asp Val
                485                    490                    495

Lys Leu Val Pro Asp Gly Lys Tyr Gly Ala Gln Asn Asp Lys Gly Glu
                500                    505                    510

Trp Asn Gly Met Val Lys Glu Leu Ile Asp His Arg Ala Asp Leu Ala
                515                    520                    525

Val Ala Pro Leu Thr Ile Thr Tyr Val Arg Glu Lys Val Ile Asp Phe
                530                    535                    540

Ser Lys Pro Phe Met Thr Leu Gly Ile Ser Ile Leu Tyr Arg Lys Pro
545                 550                    555                    560

Asn Gly Thr Asn Pro Gly Val Phe Ser Phe Leu Asn Pro Leu Ser Pro
                565                    570                    575

Asp Ile Trp Met Tyr Val Leu Leu Ala Cys Leu Gly Val Ser Cys Val
                580                    585                    590

Leu Phe Val Ile Ala Arg Phe Thr Pro Tyr Glu Trp Tyr Asn Pro His
                595                    600                    605

Pro Cys Asn Pro Asp Ser Asp Val Val Glu Asn Asn Phe Thr Leu Leu
610                 615                    620

Asn Ser Phe Trp Phe Gly Val Gly Ala Leu Met Gln Gln Gly Ser Glu
625                 630                    635                    640

Leu Met Pro Lys Ala Leu Ser Thr Arg Ile Val Gly Gly Ile Trp Trp
                645                    650                    655

Phe Phe Thr Leu Ile Ile Ile Ser Ser Tyr Thr Ala Asn Leu Ala Ala
                660                    665                    670

Phe Leu Thr Val Glu Arg Met Glu Ser Pro Ile Asp Ser Ala Asp Asp
                675                    680                    685

Leu Ala Lys Gln Thr Lys Ile Glu Tyr Gly Ala Val Arg Asp Gly Ser
                690                    695                    700

Thr Met Thr Phe Phe Lys Lys Ser Lys Ile Ser Thr Tyr Glu Lys Met
705                 710                    715                    720

Trp Ala Phe Met Ser Ser Arg Gln Gln Ser Ala Leu Val Lys Asn Ser
                725                    730                    735

Asp Glu Gly Ile Gln Arg Val Leu Thr Thr Asp Tyr Ala Leu Leu Met
                740                    745                    750

Glu Ser Thr Ser Ile Glu Tyr Val Thr Gln Arg Asn Cys Asn Leu Thr
                755                    760                    765

Gln Ile Gly Gly Leu Ile Asp Ser Lys Gly Tyr Gly Val Gly Thr Pro
                770                    775                    780

Ile Gly Ser Pro Tyr Arg Asp Lys Ile Thr Ile Ala Ile Leu Gln Leu
785                 790                    795                    800

Gln Glu Glu Gly Lys Leu His Met Met Lys Glu Lys Trp Trp Arg Gly
                805                    810                    815

```
Asn  Gly  Cys  Pro  Glu  Glu  Asp  Ser  Lys  Glu  Ala  Ser  Ala  Leu  Gly  Val
               820                      825                      830

Glu  Asn  Ile  Gly  Gly  Ile  Phe  Ile  Val  Leu  Ala  Ala  Gly  Leu  Val  Leu
          835                      840                      845

Ser  Val  Phe  Val  Ala  Ile  Gly  Glu  Phe  Leu  Tyr  Lys  Ser  Arg  Lys  Asn
     850                      855                      860

Asn  Asp  Val  Glu  Gln  Cys  Leu  Ser  Phe  Asn  Ala  Ile  Met  Glu  Glu  Leu
865                      870                      875                      880

Gly  Ile  Ser  Leu  Lys  Asn  Gln  Lys  Lys  Leu  Lys  Lys  Lys  Ser  Arg  Thr
                    885                      890                      895

Lys  Gly  Lys  Ser  Ser  Phe  Thr  Ser  Ile  Leu  Thr  Cys  His  Gln  Arg  Arg
               900                      905                      910

Thr  Gln  Arg  Lys  Glu  Thr  Val  Ala
               915                 920
```

(2) INFORMATION FOR SEQ ID NO:11:

(i) SEQUENCE CHARACTERISTICS:
  (A) LENGTH: 4608 base pairs
  (B) TYPE: nucleic acid
  (C) STRANDEDNESS: single
  (D) TOPOLOGY: linear (ii) MOLECULE TYPE: cDNA (vii) IMMEDIATE SOURCE:
  (B) CLONE: GluR6

(ix) FEATURE:
  (A) NAME/KEY: CDS
  (B) LOCATION: 307..2961

(xi) SEQUENCE DESCRIPTION: SEQ ID NO:11:

```
GAATTCGGGC TCGCAAGGGC TTCGCAGGCT GGACATTGTG CTTGCTGGAT TTTTCCCGGA        60

TGCTCCCGGA CTAACATGGA TGTCCCACCA TCCCTTGCAG TGGAAGCTTG CTCCTTGGCG       120

CAGTGAGAGT GAAGAACATG CAGCGACTGC TAATGGGTTT GGGAAGCGGA GACTCCTTCC       180

TCTTTCTGTG ACCATGCCGT GATTGTGTCT GCGGCCACTA CTCCACGCAT CTTCCTTCTC       240

GTCCAAGCCC GGAGCCTAAC GCTAGATCGG GGAAGTGGGT GCCGCGCGCG CAGGCACGGA       300

AACATC ATG AAG ATT ATT TCC CCA GTT TTA AGT AAT CTA GTC TTC AGT          348
       Met Lys Ile Ile Ser Pro Val Leu Ser Asn Leu Val Phe Ser
         1               5                  10

CGC TCC ATT AAA GTC CTG CTC TGC TTA TTG TGG ATC GGA TAT TCG CAA         396
Arg Ser Ile Lys Val Leu Leu Cys Leu Leu Trp Ile Gly Tyr Ser Gln
 15              20                  25                  30

GGA ACC ACA CAT GTG TTA AGA TTC GGT GGT ATA TTT GAA TAT GTG GAA         444
Gly Thr Thr His Val Leu Arg Phe Gly Gly Ile Phe Glu Tyr Val Glu
                 35                  40                  45

TCT GGC CCC ATG GGA GCA GAA GAA CTT GCA TTC AGA TTT GCT GTG AAT         492
Ser Gly Pro Met Gly Ala Glu Glu Leu Ala Phe Arg Phe Ala Val Asn
             50                  55                  60

ACC ATC AAC AGA AAC AGG ACT TTG CTG CCC AAC ACC ACT TTA ACT TAT         540
Thr Ile Asn Arg Asn Arg Thr Leu Leu Pro Asn Thr Thr Leu Thr Tyr
         65                  70                  75

GAT ACT CAG AAG ATC AAT CTC TAT GAC AGT TTT GAA GCA TCT AAG AAA         588
Asp Thr Gln Lys Ile Asn Leu Tyr Asp Ser Phe Glu Ala Ser Lys Lys
     80                  85                  90

GCT TGT GAT CAG CTG TCT CTT GGG GTG GCT GCT ATC TTC GGT CCT TCA         636
Ala Cys Asp Gln Leu Ser Leu Gly Val Ala Ala Ile Phe Gly Pro Ser
 95                 100                 105                 110

CAC AGT TCA TCA GCC AAT GCT GTG CAG TCC ATC TGC AAT GCT CTG GGG         684
```

|     |     |     |     |     |     |     |     |     |     |     |     |     |     |     |     |
| --- | --- | --- | --- | --- | --- | --- | --- | --- | --- | --- | --- | --- | --- | --- | --- |
| His | Ser | Ser | Ser | Ala | Asn | Ala | Val | Gln | Ser | Ile | Cys | Asn | Ala | Leu | Gly |
|     |     |     |     | 115 |     |     |     | 120 |     |     |     |     | 125 |     |     |

| GTT | CCC | CAC | ATA | CAG | ACC | CGC | TGG | AAG | CAC | CAG | GTG | TCA | GAC | AAC | AAG | 732 |
| --- | --- | --- | --- | --- | --- | --- | --- | --- | --- | --- | --- | --- | --- | --- | --- | --- |
| Val | Pro | His | Ile | Gln | Thr | Arg | Trp | Lys | His | Gln | Val | Ser | Asp | Asn | Lys |     |
|     |     |     | 130 |     |     |     |     | 135 |     |     |     |     | 140 |     |     |     |

| GAT | TCC | TTC | TAC | GTC | AGT | CTC | TAC | CCA | GAC | TTC | TCT | TCC | CTG | AGC | CGC | 780 |
| --- | --- | --- | --- | --- | --- | --- | --- | --- | --- | --- | --- | --- | --- | --- | --- | --- |
| Asp | Ser | Phe | Tyr | Val | Ser | Leu | Tyr | Pro | Asp | Phe | Ser | Ser | Leu | Ser | Arg |     |
|     |     |     | 145 |     |     |     |     | 150 |     |     |     |     | 155 |     |     |     |

| GCC | ATC | TTG | GAT | TTG | GTG | CAG | TTT | TTT | AAG | TGG | AAA | ACT | GTC | ACA | GTT | 828 |
| --- | --- | --- | --- | --- | --- | --- | --- | --- | --- | --- | --- | --- | --- | --- | --- | --- |
| Ala | Ile | Leu | Asp | Leu | Val | Gln | Phe | Phe | Lys | Trp | Lys | Thr | Val | Thr | Val |     |
|     |     |     | 160 |     |     |     |     | 165 |     |     |     |     | 170 |     |     |     |

| GTG | TAT | GAC | GAC | AGC | ACT | GGT | CTC | ATT | CGC | TTG | CAA | GAG | CTC | ATC | AAA | 876 |
| --- | --- | --- | --- | --- | --- | --- | --- | --- | --- | --- | --- | --- | --- | --- | --- | --- |
| Val | Tyr | Asp | Asp | Ser | Thr | Gly | Leu | Ile | Arg | Leu | Gln | Glu | Leu | Ile | Lys |     |
| 175 |     |     |     |     | 180 |     |     |     |     | 185 |     |     |     |     | 190 |     |

| GCT | CCA | TCG | AGG | TAC | AAT | CTT | CGA | CTT | AAA | ATT | CGT | CAG | CTG | CCA | GCT | 924 |
| --- | --- | --- | --- | --- | --- | --- | --- | --- | --- | --- | --- | --- | --- | --- | --- | --- |
| Ala | Pro | Ser | Arg | Tyr | Asn | Leu | Arg | Leu | Lys | Ile | Arg | Gln | Leu | Pro | Ala |     |
|     |     |     |     | 195 |     |     |     |     | 200 |     |     |     |     | 205 |     |     |

| GAT | ACC | AAA | GAT | GCA | AAA | CCT | TTG | CTG | AAG | GAG | ATG | AAA | AGA | GGC | AAG | 972 |
| --- | --- | --- | --- | --- | --- | --- | --- | --- | --- | --- | --- | --- | --- | --- | --- | --- |
| Asp | Thr | Lys | Asp | Ala | Lys | Pro | Leu | Leu | Lys | Glu | Met | Lys | Arg | Gly | Lys |     |
|     |     |     | 210 |     |     |     |     | 215 |     |     |     |     | 220 |     |     |     |

| GAG | TTC | CAC | GTG | ATC | TTC | GAC | TGC | AGC | CAT | GAG | ATG | GCA | GCA | GGC | ATT | 1020 |
| --- | --- | --- | --- | --- | --- | --- | --- | --- | --- | --- | --- | --- | --- | --- | --- | --- |
| Glu | Phe | His | Val | Ile | Phe | Asp | Cys | Ser | His | Glu | Met | Ala | Ala | Gly | Ile |     |
|     |     | 225 |     |     |     |     | 230 |     |     |     |     | 235 |     |     |     |     |

| TTA | AAA | CAG | GCA | TTA | GCT | ATG | GGA | ATG | ATG | ACA | GAA | TAC | TAT | CAC | TAT | 1068 |
| --- | --- | --- | --- | --- | --- | --- | --- | --- | --- | --- | --- | --- | --- | --- | --- | --- |
| Leu | Lys | Gln | Ala | Leu | Ala | Met | Gly | Met | Met | Thr | Glu | Tyr | Tyr | His | Tyr |     |
| 240 |     |     |     |     | 245 |     |     |     |     | 250 |     |     |     |     |     |     |

| ATA | TTT | ACA | ACT | CTG | GAC | CTC | TTT | GCT | CTT | GAC | GTG | GAG | CCC | TAC | AGA | 1116 |
| --- | --- | --- | --- | --- | --- | --- | --- | --- | --- | --- | --- | --- | --- | --- | --- | --- |
| Ile | Phe | Thr | Thr | Leu | Asp | Leu | Phe | Ala | Leu | Asp | Val | Glu | Pro | Tyr | Arg |     |
| 255 |     |     |     |     | 260 |     |     |     |     | 265 |     |     |     |     | 270 |     |

| TAC | AGT | GGC | GTA | AAT | ATG | ACA | GGG | TTC | AGG | ATA | CTA | AAT | ACA | GAG | AAT | 1164 |
| --- | --- | --- | --- | --- | --- | --- | --- | --- | --- | --- | --- | --- | --- | --- | --- | --- |
| Tyr | Ser | Gly | Val | Asn | Met | Thr | Gly | Phe | Arg | Ile | Leu | Asn | Thr | Glu | Asn |     |
|     |     |     |     | 275 |     |     |     |     | 280 |     |     |     |     | 285 |     |     |

| ACC | CAA | GTC | TCC | TCC | ATC | ATC | GAA | AAG | TGG | TCT | ATG | GAA | CGG | TTA | CAG | 1212 |
| --- | --- | --- | --- | --- | --- | --- | --- | --- | --- | --- | --- | --- | --- | --- | --- | --- |
| Thr | Gln | Val | Ser | Ser | Ile | Ile | Glu | Lys | Trp | Ser | Met | Glu | Arg | Leu | Gln |     |
|     |     |     | 290 |     |     |     |     | 295 |     |     |     |     | 300 |     |     |     |

| GCG | CCT | CCA | AAA | CCT | GAC | TCA | GGT | TTG | CTG | GAT | GGA | TTT | ATG | ACG | ACT | 1260 |
| --- | --- | --- | --- | --- | --- | --- | --- | --- | --- | --- | --- | --- | --- | --- | --- | --- |
| Ala | Pro | Pro | Lys | Pro | Asp | Ser | Gly | Leu | Leu | Asp | Gly | Phe | Met | Thr | Thr |     |
|     |     | 305 |     |     |     |     | 310 |     |     |     |     | 315 |     |     |     |     |

| GAT | GCT | GCT | CTG | ATG | TAT | GAT | GCA | GTG | CAC | GTT | GTG | TCT | GTG | GCT | GTC | 1308 |
| --- | --- | --- | --- | --- | --- | --- | --- | --- | --- | --- | --- | --- | --- | --- | --- | --- |
| Asp | Ala | Ala | Leu | Met | Tyr | Asp | Ala | Val | His | Val | Val | Ser | Val | Ala | Val |     |
|     | 320 |     |     |     |     | 325 |     |     |     |     | 330 |     |     |     |     |     |

| CAA | CAG | TTT | CCC | CAG | ATG | ACA | GTC | AGC | TCC | TTG | CAA | TGC | AAT | CGA | CAC | 1356 |
| --- | --- | --- | --- | --- | --- | --- | --- | --- | --- | --- | --- | --- | --- | --- | --- | --- |
| Gln | Gln | Phe | Pro | Gln | Met | Thr | Val | Ser | Ser | Leu | Gln | Cys | Asn | Arg | His |     |
| 335 |     |     |     |     | 340 |     |     |     |     | 345 |     |     |     |     | 350 |     |

| AAA | CCC | TGG | CGC | TTT | GGG | ACC | CGC | TTC | ATG | AGT | CTA | ATT | AAA | GAG | GCT | 1404 |
| --- | --- | --- | --- | --- | --- | --- | --- | --- | --- | --- | --- | --- | --- | --- | --- | --- |
| Lys | Pro | Trp | Arg | Phe | Gly | Thr | Arg | Phe | Met | Ser | Leu | Ile | Lys | Glu | Ala |     |
|     |     |     |     | 355 |     |     |     |     | 360 |     |     |     |     | 365 |     |     |

| CAC | TGG | GAA | GGT | CTC | ACA | GGC | AGA | ATA | ACA | TTT | AAC | AAA | ACC | AAT | GGA | 1452 |
| --- | --- | --- | --- | --- | --- | --- | --- | --- | --- | --- | --- | --- | --- | --- | --- | --- |
| His | Trp | Glu | Gly | Leu | Thr | Gly | Arg | Ile | Thr | Phe | Asn | Lys | Thr | Asn | Gly |     |
|     |     |     | 370 |     |     |     |     | 375 |     |     |     |     | 380 |     |     |     |

| TTA | CGG | ACA | GAT | TTT | GAT | TTG | GAT | GTG | ATC | AGT | CTC | AAG | GAA | GAA | GGT | 1500 |
| --- | --- | --- | --- | --- | --- | --- | --- | --- | --- | --- | --- | --- | --- | --- | --- | --- |
| Leu | Arg | Thr | Asp | Phe | Asp | Leu | Asp | Val | Ile | Ser | Leu | Lys | Glu | Glu | Gly |     |
|     |     | 385 |     |     |     |     | 390 |     |     |     |     | 395 |     |     |     |     |

| CTG | GAG | AAG | ATT | GGA | ACT | TGG | GAT | CCA | GCC | AGT | GGC | CTG | AAT | ATG | ACA | 1548 |
| --- | --- | --- | --- | --- | --- | --- | --- | --- | --- | --- | --- | --- | --- | --- | --- | --- |
| Leu | Glu | Lys | Ile | Gly | Thr | Trp | Asp | Pro | Ala | Ser | Gly | Leu | Asn | Met | Thr |     |
|     | 400 |     |     |     |     | 405 |     |     |     |     | 410 |     |     |     |     |     |

| GAA | AGT | CAG | AAA | GGA | AAG | CCA | GCA | AAT | ATC | ACA | GAC | TCA | TTG | TCT | AAT | 1596 |
| --- | --- | --- | --- | --- | --- | --- | --- | --- | --- | --- | --- | --- | --- | --- | --- | --- |
| Glu | Ser | Gln | Lys | Gly | Lys | Pro | Ala | Asn | Ile | Thr | Asp | Ser | Leu | Ser | Asn |     |
| 415 |     |     |     |     | 420 |     |     |     |     | 425 |     |     |     |     | 430 |     |

| CGT | TCT | TTG | ATT | GTT | ACC | ACC | ATT | TTG | GAA | GAA | CCG | TAT | GTT | CTG | TTT | 1644 |
| --- | --- | --- | --- | --- | --- | --- | --- | --- | --- | --- | --- | --- | --- | --- | --- | --- |

|     |     |     |     |     |     |     |     |     |     |     |     |     |     |     |     |
|-----|-----|-----|-----|-----|-----|-----|-----|-----|-----|-----|-----|-----|-----|-----|-----|
| Arg | Ser | Leu | Ile | Val 435 | Thr | Thr | Ile | Leu | Glu 440 | Glu | Pro | Tyr | Val | Leu 445 | Phe |

| AAG | AAG | TCT | GAC | AAA | CCA | CTC | TAT | GGG | AAT | GAT | CGA | TTT | GAA | GGC | TAC | 1692 |
|-----|-----|-----|-----|-----|-----|-----|-----|-----|-----|-----|-----|-----|-----|-----|-----|------|
| Lys | Lys | Ser | Asp 450 | Lys | Pro | Leu | Tyr | Gly 455 | Asn | Asp | Arg | Phe | Glu 460 | Gly | Tyr | |

| TGT | ATT | GAT | CTC | CTA | CGA | GAG | TTA | TCT | ACA | ATC | CTT | GGC | TTT | ACA | TAT | 1740 |
| Cys | Ile | Asp 465 | Leu | Leu | Arg | Glu | Leu 470 | Ser | Thr | Ile | Leu | Gly 475 | Phe | Thr | Tyr | |

| GAG | ATT | AGG | CTT | GTG | GAG | GAT | GGG | AAA | TAT | GGA | GCC | CAG | GAT | GAT | GTG | 1788 |
| Glu | Ile | Arg 480 | Leu | Val | Glu | Asp 485 | Gly | Lys | Tyr | Gly | Ala 490 | Gln | Asp | Asp | Val | |

| AAC | GGA | CAA | TGG | AAT | GGA | ATG | GTT | CGT | GAA | CTA | ATC | GAT | CAT | AAA | GCT | 1836 |
| Asn | Gly | Gln | Trp | Asn 500 | Gly | Met | Val | Arg | Glu | Leu 505 | Ile | Asp | His | Lys | Ala 510 | |
| 495 | | | | | | | | | | | | | | | | |

| GAC | CTT | GCA | GTT | GCT | CCA | CTG | GCT | ATA | ACC | TAT | GTT | CGT | GAG | AAG | GTC | 1884 |
| Asp | Leu | Ala | Val | Ala 515 | Pro | Leu | Ala | Ile | Thr 520 | Tyr | Val | Arg | Glu | Lys 525 | Val | |

| ATC | GAC | TTT | TCA | AAG | CCG | TTT | ATG | ACA | CTT | GGA | ATA | AGT | ATT | TTG | TAC | 1932 |
| Ile | Asp | Phe | Ser 530 | Lys | Pro | Phe | Met | Thr 535 | Leu | Gly | Ile | Ser | Ile 540 | Leu | Tyr | |

| CGC | AAG | CCC | AAT | GGT | ACA | AAC | CCA | GGC | GTC | TTC | TCC | TTC | CTG | AAT | CCT | 1980 |
| Arg | Lys | Pro | Asn 545 | Gly | Thr | Asn | Pro | Gly 550 | Val | Phe | Ser | Phe | Leu 555 | Asn | Pro | |

| CTC | TCC | CCT | GAT | ATC | TGG | ATG | TAT | GTT | CTG | CTG | GCT | TGC | TTG | GGT | GTC | 2028 |
| Leu | Ser | Pro | Asp | Ile 560 | Trp | Met | Tyr | Val | Leu 565 | Leu | Ala | Cys | Leu | Gly 570 | Val | |

| AGT | TGT | GTG | CTC | TTT | GTC | ATA | GCC | AGG | TTT | AGT | CCC | TAT | GAG | TGG | TAT | 2076 |
| Ser | Cys | Val | Leu | Phe | Val 580 | Ile | Ala | Arg | Phe | Ser 585 | Pro | Tyr | Glu | Trp | Tyr 590 | |
| 575 | | | | | | | | | | | | | | | | |

| AAC | CCA | CAC | CCT | TGC | AAC | CCT | GAC | TCA | GAC | GTG | GTG | GAA | AAC | AAT | TTT | 2124 |
| Asn | Pro | His | Pro | Cys 595 | Asn | Pro | Asp | Ser | Asp 600 | Val | Val | Glu | Asn | Asn 605 | Phe | |

| ACC | TTG | CTA | AAT | AGT | TTC | TGG | TTT | GGA | GTT | GGA | GCT | CTC | ATG | CGG | CAA | 2172 |
| Thr | Leu | Leu | Asn 610 | Ser | Phe | Trp | Phe | Gly 615 | Val | Gly | Ala | Leu | Met 620 | Arg | Gln | |

| GGT | TCT | GAG | CTC | ATG | CCC | AAA | GCA | CTC | TCC | ACC | AGG | ATA | GTG | GGA | GGC | 2220 |
| Gly | Ser | Glu | Leu | Met 625 | Pro | Lys | Ala | Leu | Ser 630 | Thr | Arg | Ile | Val | Gly 635 | Gly | |

| ATT | TGG | TGG | TTT | TTC | ACA | CTT | ATC | ATC | ATT | TCT | TCG | TAT | ACC | GCT | AAC | 2268 |
| Ile | Trp | Trp | Phe | Phe 640 | Thr | Leu | Ile | Ile | Ile 645 | Ser | Ser | Tyr | Thr | Ala 650 | Asn | |

| CTA | GCC | GCC | TTT | CTG | ACT | GTG | GAA | CGC | ATG | GAG | TCG | CCC | ATT | GAC | TCT | 2316 |
| Leu | Ala | Ala | Phe | Leu | Thr 660 | Val | Glu | Arg | Met | Glu 665 | Ser | Pro | Ile | Asp | Ser 670 | |
| 655 | | | | | | | | | | | | | | | | |

| GCT | GAC | GAT | TTA | GCT | AAG | CAA | ACC | AAG | ATA | GAG | TAT | GGA | GCA | GTG | GAG | 2364 |
| Ala | Asp | Asp | Leu | Ala 675 | Lys | Gln | Thr | Lys | Ile 680 | Glu | Tyr | Gly | Ala | Val 685 | Glu | |

| GAC | GGC | GCA | ACC | ATG | ACG | TTT | TTT | AAG | AAA | TCA | AAA | ATT | TCA | ACG | TAT | 2412 |
| Asp | Gly | Ala | Thr | Met 690 | Thr | Phe | Phe | Lys | Lys 695 | Ser | Lys | Ile | Ser | Thr 700 | Tyr | |

| GAT | AAA | ATG | TGG | GCG | TTT | ATG | AGC | AGC | AGG | AGA | CAG | TCT | GTG | CTT | GTC | 2460 |
| Asp | Lys | Met | Trp 705 | Ala | Phe | Met | Ser | Ser 710 | Arg | Arg | Gln | Ser | Val 715 | Leu | Val | |

| AAA | AGC | AAT | GAG | GAA | GGG | ATC | CAA | CGA | GTC | CTC | ACC | TCG | GAT | TAT | GCT | 2508 |
| Lys | Ser | Asn | Glu | Glu 720 | Gly | Ile | Gln | Arg | Val 725 | Leu | Thr | Ser | Asp | Tyr 730 | Ala | |

| TTC | TTA | ATG | GAG | TCA | ACA | ACC | ATC | GAG | TTT | GTT | ACA | CAG | CGG | AAC | TGT | 2556 |
| Phe | Leu | Met | Glu | Ser 740 | Thr | Thr | Ile | Glu | Phe 745 | Val | Thr | Gln | Arg | Asn 750 | Cys | |
| 735 | | | | | | | | | | | | | | | | |

| AAC | CTC | ACG | CAG | ATT | GGC | GGC | CTT | ATA | GAC | TCC | AAA | GGC | TAT | GGC | GTT | 2604 |

```
            Asn Leu Thr Gln Ile Gly Gly Leu Ile Asp Ser Lys Gly Tyr Gly Val
                        755             760                 765

GGC ACT CCT ATG GGC TCT CCA TAT CGA GAC AAA ATC ACC ATA GCA ATT              2652
Gly Thr Pro Met Gly Ser Pro Tyr Arg Asp Lys Ile Thr Ile Ala Ile
            770             775                 780

CTT CAG CTG CAG GAG GAA GGC AAG CTG CAC ATG ATG AAG GAG AAA TGG              2700
Leu Gln Leu Gln Glu Glu Gly Lys Leu His Met Met Lys Glu Lys Trp
            785             790                 795

TGG CGG GGC AAT GGC TGC CCA GAG GAG GAG AGC AAA GAG GCC AGT GCT              2748
Trp Arg Gly Asn Gly Cys Pro Glu Glu Glu Ser Lys Glu Ala Ser Ala
    800             805                 810

CTG GGG GTG CAG AAT ATT GGT GGT ATC TTC ATT GTC CTG GCA GCC GGC              2796
Leu Gly Val Gln Asn Ile Gly Gly Ile Phe Ile Val Leu Ala Ala Gly
815             820                 825                 830

TTG GTG CTC TCA GTT TTT GTG GCA GTG GGA GAG TTT TTA TAC AAA TCC              2844
Leu Val Leu Ser Val Phe Val Ala Val Gly Glu Phe Leu Tyr Lys Ser
                835                 840                 845

AAA AAA AAC GCT CAA TTG GAA AAG AGG TCC TTC TGT AGC GCT ATG GTG              2892
Lys Lys Asn Ala Gln Leu Glu Lys Arg Ser Phe Cys Ser Ala Met Val
            850                 855                 860

GAA GAG CTG AGA ATG TCC CTG AAG TGC CAG CGT CGG CTC AAA CAT AAG              2940
Glu Glu Leu Arg Met Ser Leu Lys Cys Gln Arg Arg Leu Lys His Lys
            865                 870                 875

CCA CAG CCC CAG TTA TTG TGAAAACAGA AGAAGTTATC AACATGCACA                     2988
Pro Gln Pro Gln Leu Leu
            880                 885

CATTTAACGA CAGAAGGTTG CCAGGTAAAG AAACCATGGC ATGAAGCTGG GAGGCCAATC            3048

ACCCAAGCAC AAACTGTCGT CTTTTTTTT  TTTTTTCCA  AACAATTTAG CGAGAATGTT            3108

TCCTGTGGAA ATATGCAACC TGTGCAAAAT AAAATGAGTT ACCTCATGCC GCTGTGTCTA            3168

TGAACTAGAG ACTCTGTGAT CTAAGCAGTT TCAGTGATCA GACTTGATTT ACAAGCACCG            3228

TGGATCAACC AAGTTACACG GGGTTACACT GTTTATCATA GGTTCCTCCC TTCCTTTGAG            3288

TGAATGTTAC ATGCAAATGT TGTGGCTGGT TTCAAATGCA GTCCAGGGAG AAACTGCTGG            3348

TTCCTTCTGA AGCTCAGCTG TCGTCAGGAG ATGGAATGCC GGTGCCCAAA AGGGTAACCA            3408

ATAAAAATGC CATAAAAATT TTAAAAAAAT GCGTGAGATC GGCAAAAATT ATAGTGTTAC            3468

AAGAAACAGT ACAGTCCCAT GGTCACCAAC ACAATAGAGG TGATAATGTT ACTAGCCCCC            3528

AATACTCAGT AAAATCGTCA TCTGAATAGA TAATATGTGT TCATAGAATG TGAAAAAAAA            3588

TGTAATGCGA GACACACCAG TATCAATAGA AGTGGAACTG AAGGCAGAAC ATCATCAGTT            3648

ACTTTTCTTT TTCAATAGTC TGTGTCATGG ATTGTGATAT AGATGGCAAT TATCAAGCCA            3708

ATAATTTTTT TTCTGAAAAT ACCTATGGCA AATATTTTAA TAGGCAACTT GCTCCCACAA            3768

ATCCCTACTC TAACCTCCCC CAGAAATATA AAAGGAACCA TTGGTTTAGA GATTGGTATG            3828

TAAGAGATGA TGTTTTGCAA GCCTTGTCGT GCATTGTAAA AGGGCTCAGT GTTACTGGTT            3888

ACAGGGAAGA CTGAAGCTTT CACCCTGACA TTCTGAAATG TCAACCGAAA CTCTCCTTCC            3948

TCCTGTAAAG GACCTTGATG GGCAGATTC  CATTGATCAA AGAATGGGGA CTTGTCACCT            4008

ATACAATGGT ACGTGACAGA ACTTTGAGGT GGACTGCATT TAATAATAGT CACAATGTTA            4068

AAAGAACAAA ATTCTTGAGC AGTTTTTTTT TTTGTTTTG  TTTTGTTTTC AAAAAATGTT            4128

CAGGTTTATT TGTGGAAATG CAAGATTTCT ATAAAATAGT TTTTGTATGG AAATTTTTGT            4188

AATACTTTTT ATCAACAAAA TAAGAACACA TGTTTCTGTC AGGGGTGTGA GGTCAAGCAT            4248

GAACGGTAGT GCGTGTGCAC CACCAACGTT TGGTGAAACT ATTTTTATCA AGAAAAAGGA            4308

ATCATAGAAG AGAAATATTT TCAAGTTAGA TACTATAAAA GCTAGGTGCA CTACCACCAC            4368
```

```
GGCTTGTCGC GCCACACCCC TGAGTCCACA AGGTGGATAA CATATTGTAA TGAACAGTTG    4428

TGTGTAAAAT GGCAAAAGAC ACAGACCTCT TGACAACATT GTGAAAACAG TTGAGTGCAC    4488

ACAGTTTGCT GTTTGAATCC AATGCACAAA AATTTTACAA AAATCCATTA AAATTATGTC    4548

CGTTTTAAAA CCTGCAGCCC GGGGGATCCA CTAGTTCTAG AGCCGGTGCC CAATTCGCCC    4608
```

( 2 ) INFORMATION FOR SEQ ID NO:12:

( i ) SEQUENCE CHARACTERISTICS:
  ( A ) LENGTH: 884 amino acids
  ( B ) TYPE: amino acid
  ( D ) TOPOLOGY: linear ( i i ) MOLECULE TYPE: protein ( x i ) SEQUENCE DESCRIPTION: SEQ ID NO:12:

```
Met Lys Ile Ile Ser Pro Val Leu Ser Asn Leu Val Phe Ser Arg Ser
 1               5                  10                  15

Ile Lys Val Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110

Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320
```

| | | | | | | | | | | | | | | |
|---|---|---|---|---|---|---|---|---|---|---|---|---|---|---|
|Ala|Leu|Met|Tyr|Asp<br>325|Ala|Val|His|Val<br>330|Ser|Val|Ala|Val<br>335|Gln|Gln|
|Phe|Pro|Gln|Met<br>340|Thr|Val|Ser|Ser|Leu<br>345|Gln|Cys|Asn|Arg|His<br>350|Lys|Pro|
|Trp|Arg|Phe<br>355|Gly|Thr|Arg|Phe|Met<br>360|Ser|Leu|Ile|Lys|Glu<br>365|Ala|His|Trp|
|Glu|Gly<br>370|Leu|Thr|Gly|Arg|Ile<br>375|Thr|Phe|Asn|Lys|Thr<br>380|Asn|Gly|Leu|Arg|
|Thr<br>385|Asp|Phe|Asp|Leu|Asp<br>390|Val|Ile|Ser|Leu|Lys<br>395|Glu|Glu|Gly|Leu|Glu<br>400|
|Lys|Ile|Gly|Thr|Trp<br>405|Asp|Pro|Ala|Ser|Gly<br>410|Leu|Asn|Met|Thr|Glu<br>415|Ser|
|Gln|Lys|Gly|Lys<br>420|Pro|Ala|Asn|Ile|Thr<br>425|Asp|Ser|Leu|Ser|Asn<br>430|Arg|Ser|
|Leu|Ile|Val<br>435|Thr|Thr|Ile|Leu|Glu<br>440|Glu|Pro|Tyr|Val|Leu<br>445|Phe|Lys|Lys|
|Ser|Asp<br>450|Lys|Pro|Leu|Tyr|Gly<br>455|Asn|Asp|Arg|Phe|Glu<br>460|Gly|Tyr|Cys|Ile|
|Asp<br>465|Leu|Leu|Arg|Glu|Leu<br>470|Ser|Thr|Ile|Leu|Gly<br>475|Phe|Thr|Tyr|Glu|Ile<br>480|
|Arg|Leu|Val|Glu|Asp<br>485|Gly|Lys|Tyr|Gly|Ala<br>490|Gln|Asp|Asp|Val|Asn<br>495|Gly|
|Gln|Trp|Asn|Gly|Met<br>500|Val|Arg|Glu|Leu|Ile<br>505|Asp|His|Lys|Ala|Asp<br>510|Leu|
|Ala|Val|Ala|Pro<br>515|Leu|Ala|Ile|Thr|Tyr<br>520|Val|Arg|Glu|Lys|Val<br>525|Ile|Asp|
|Phe|Ser|Lys|Pro<br>530|Phe|Met|Thr|Leu<br>535|Gly|Ile|Ser|Ile|Leu<br>540|Tyr|Arg|Lys|
|Pro|Asn|Gly|Thr|Asn<br>545|Pro|Gly|Val|Phe|Ser<br>550|Phe|Leu|Asn|Pro|Leu<br>555|Ser<br>560|
|Pro|Asp|Ile|Trp|Met<br>565|Tyr|Val|Leu|Leu|Ala<br>570|Cys|Leu|Gly|Val|Ser<br>575|Cys|
|Val|Leu|Phe|Val<br>580|Ile|Ala|Arg|Phe|Ser<br>585|Pro|Tyr|Glu|Trp|Tyr<br>590|Asn|Pro|
|His|Pro|Cys<br>595|Asn|Pro|Asp|Ser|Asp<br>600|Val|Val|Glu|Asn|Asn<br>605|Phe|Thr|Leu|
|Leu|Asn<br>610|Ser|Phe|Trp|Phe|Gly<br>615|Val|Gly|Ala|Leu|Met<br>620|Arg|Gln|Gly|Ser|
|Glu<br>625|Leu|Met|Pro|Lys|Ala<br>630|Leu|Ser|Thr|Arg|Ile<br>635|Val|Gly|Gly|Ile|Trp<br>640|
|Trp|Phe|Phe|Thr|Leu<br>645|Ile|Ile|Ile|Ser|Ser<br>650|Tyr|Thr|Ala|Asn|Leu<br>655|Ala|
|Ala|Phe|Leu|Thr<br>660|Val|Glu|Arg|Met|Glu<br>665|Ser|Pro|Ile|Asp|Ser<br>670|Ala|Asp|
|Asp|Leu|Ala<br>675|Lys|Gln|Thr|Lys|Ile<br>680|Glu|Tyr|Gly|Ala|Val<br>685|Glu|Asp|Gly|
|Ala|Thr|Met<br>690|Thr|Phe|Phe|Lys|Lys<br>695|Ser|Lys|Ile|Ser|Thr<br>700|Tyr|Asp|Lys|
|Met<br>705|Trp|Ala|Phe|Met|Ser<br>710|Ser|Arg|Arg|Gln|Ser<br>715|Val|Leu|Val|Lys|Ser<br>720|
|Asn|Glu|Glu|Gly|Ile<br>725|Gln|Arg|Val|Leu|Thr<br>730|Ser|Asp|Tyr|Ala|Phe<br>735|Leu|
|Met|Glu|Ser|Thr|Thr|Ile|Glu|Phe|Val|Thr|Gln|Arg|Asn|Cys|Asn|Leu|

```
                    740                       745                         750
Thr Gln Ile Gly Gly Leu Ile Asp Ser Lys Gly Tyr Gly Val Gly Thr
            755                   760                   765
Pro Met Gly Ser Pro Tyr Arg Asp Lys Ile Thr Ile Ala Ile Leu Gln
    770                 775                 780
Leu Gln Glu Glu Gly Lys Leu His Met Met Lys Glu Lys Trp Trp Arg
785                 790                 795                         800
Gly Asn Gly Cys Pro Glu Glu Glu Ser Lys Glu Ala Ser Ala Leu Gly
                805                 810                     815
Val Gln Asn Ile Gly Gly Ile Phe Ile Val Leu Ala Ala Gly Leu Val
            820                 825                 830
Leu Ser Val Phe Val Ala Val Gly Glu Phe Leu Tyr Lys Ser Lys Lys
        835                 840                 845
Asn Ala Gln Leu Glu Lys Arg Ser Phe Cys Ser Ala Met Val Glu Glu
850                 855                 860
Leu Arg Met Ser Leu Lys Cys Gln Arg Arg Leu Lys His Lys Pro Gln
865                 870                 875                     880
Pro Gln Leu Leu
```

( 2 ) INFORMATION FOR SEQ ID NO:13:

( i ) SEQUENCE CHARACTERISTICS:
        ( A ) LENGTH: 3344 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( G ) CELL TYPE:
        ( H ) CELL LINE:

( v i i ) IMMEDIATE SOURCE:
        ( A ) LIBRARY:
        ( B ) CLONE: GluR7

( i x ) FEATURE:
        ( A ) NAME/KEY: CDS
        ( B ) LOCATION: 1..2766

( x i ) SEQUENCE DESCRIPTION: SEQ ID NO:13:

```
GGG GCC GTG GCG GGC TCC CTG GGG CGC CTC CGG AGT CTG GTT TGG GAA         48
Gly Ala Val Ala Gly Ser Leu Gly Arg Leu Arg Ser Leu Val Trp Glu
  1               5                  10                      15

TAC TGG GCC GGG TTC CTC GTG TGC GCC TTC TGG ATC CCA GAC TCG CGC         96
Tyr Trp Ala Gly Phe Leu Val Cys Ala Phe Trp Ile Pro Asp Ser Arg
             20                  25                  30

GGG ATG CCC CAC GTC ATC CGG ATC GGC GGA ATC TTT GAG TAC GCG GAC        144
Gly Met Pro His Val Ile Arg Ile Gly Gly Ile Phe Glu Tyr Ala Asp
         35                  40                  45

GGC CCC AAC GCC CAG GTC ATG AAC GCT GAG GAG CAC GCC TTT CGG TTT        192
Gly Pro Asn Ala Gln Val Met Asn Ala Glu Glu His Ala Phe Arg Phe
     50                  55                  60

TCT GCC AAT ATC ATC AAC AGG AAC AGA ACT CTG CTG CCC AAC ACG ACC        240
Ser Ala Asn Ile Ile Asn Arg Asn Arg Thr Leu Leu Pro Asn Thr Thr
 65                  70                  75                  80

CTG ACC TAC GAC ATT CAG AGG ATT CAC TTC CAT GAC AGT TTT GAG GCC        288
Leu Thr Tyr Asp Ile Gln Arg Ile His Phe His Asp Ser Phe Glu Ala
                 85                  90                  95

ACC AAG AAG GCC TGT GAC CAG TTG GCG CTC GGT GTG GTA GCC ATC TTT        336
Thr Lys Lys Ala Cys Asp Gln Leu Ala Leu Gly Val Val Ala Ile Phe
            100                 105                 110
```

-continued

| | | | | | | | | | | | | | | | | |
|---|---|---|---|---|---|---|---|---|---|---|---|---|---|---|---|---|
| GGG | CCA | TCC | CAG | GGC | TCC | TGC | ATC | AAT | GCC | GTC | CAG | TCC | ATC | TGC | AAT | 384 |
| Gly | Pro | Ser | Gln | Gly | Ser | Cys | Ile | Asn | Ala | Val | Gln | Ser | Ile | Cys | Asn | |
| | | 115 | | | | 120 | | | | | 125 | | | | | |
| GCC | TTG | GAG | GTT | CCT | CAC | ATC | CAA | CTG | CGC | TGG | AAG | CAC | CAC | CCC | CTG | 432 |
| Ala | Leu | Glu | Val | Pro | His | Ile | Gln | Leu | Arg | Trp | Lys | His | His | Pro | Leu | |
| | 130 | | | | 135 | | | | | 140 | | | | | | |
| GAC | AAC | AAG | GAC | ACC | TTC | TAC | GTG | AAC | CTC | TAC | CCC | GAC | TAC | GCC | TCT | 480 |
| Asp | Asn | Lys | Asp | Thr | Phe | Tyr | Val | Asn | Leu | Tyr | Pro | Asp | Tyr | Ala | Ser | |
| 145 | | | | | 150 | | | | | 155 | | | | | 160 | |
| CTC | AGC | CAC | GCC | ATC | CTC | GAC | TTG | GTC | CAG | TCC | CTC | AAG | TGG | CGG | TCA | 528 |
| Leu | Ser | His | Ala | Ile | Leu | Asp | Leu | Val | Gln | Ser | Leu | Lys | Trp | Arg | Ser | |
| | | | | 165 | | | | | 170 | | | | | 175 | | |
| GCC | ACC | GTA | GTC | TAT | GAT | GAC | AGT | ACA | GGT | CTC | ATC | CGG | CTG | CAG | GAG | 576 |
| Ala | Thr | Val | Val | Tyr | Asp | Asp | Ser | Thr | Gly | Leu | Ile | Arg | Leu | Gln | Glu | |
| | | | 180 | | | | | 185 | | | | | 190 | | | |
| CTC | ATC | ATG | GCT | CCA | TCT | AGG | TAC | AAC | ATC | CGC | CTG | AAG | ATT | CGC | CAG | 624 |
| Leu | Ile | Met | Ala | Pro | Ser | Arg | Tyr | Asn | Ile | Arg | Leu | Lys | Ile | Arg | Gln | |
| | | 195 | | | | | 200 | | | | | 205 | | | | |
| CTC | CCC | ATC | GAC | TCC | GAT | GAC | TCA | CGC | CCC | TTG | CTC | AAA | GAG | ATG | AAG | 672 |
| Leu | Pro | Ile | Asp | Ser | Asp | Asp | Ser | Arg | Pro | Leu | Leu | Lys | Glu | Met | Lys | |
| | 210 | | | | | 215 | | | | | 220 | | | | | |
| CGG | GGC | CGG | GAG | TTC | CGT | ATC | ATC | TTT | GAC | TGC | AGT | CAC | ACC | ATG | GCA | 720 |
| Arg | Gly | Arg | Glu | Phe | Arg | Ile | Ile | Phe | Asp | Cys | Ser | His | Thr | Met | Ala | |
| 225 | | | | | 230 | | | | | 235 | | | | | 240 | |
| GCC | CAG | ATC | CTC | AAG | CAG | GCC | ATG | GCC | ATG | GGC | ATG | ATG | ACG | GAA | TAC | 768 |
| Ala | Gln | Ile | Leu | Lys | Gln | Ala | Met | Ala | Met | Gly | Met | Met | Thr | Glu | Tyr | |
| | | | | 245 | | | | | 250 | | | | | 255 | | |
| TAC | CAC | TTC | ATC | TTC | ACC | ACT | CTG | GAT | CTC | TAT | GCG | CTA | GAC | CTG | GAA | 816 |
| Tyr | His | Phe | Ile | Phe | Thr | Thr | Leu | Asp | Leu | Tyr | Ala | Leu | Asp | Leu | Glu | |
| | | | 260 | | | | | 265 | | | | | 270 | | | |
| CCC | TAC | CGC | TAC | TCG | GGA | GTG | AAC | CTG | ACT | GGG | TTC | CGC | ATA | CTC | AAC | 864 |
| Pro | Tyr | Arg | Tyr | Ser | Gly | Val | Asn | Leu | Thr | Gly | Phe | Arg | Ile | Leu | Asn | |
| | | 275 | | | | | 280 | | | | | 285 | | | | |
| GTG | GAC | AAC | CCC | CAT | GTC | TCA | GCC | ATT | GTG | GAG | AAG | TGG | TCC | ATG | GAG | 912 |
| Val | Asp | Asn | Pro | His | Val | Ser | Ala | Ile | Val | Glu | Lys | Trp | Ser | Met | Glu | |
| | 290 | | | | | 295 | | | | | 300 | | | | | |
| CGG | CTA | CAG | GCA | GCT | CCC | CGG | GCA | GAG | TCA | GGC | CTG | CTG | GAT | GGA | GTG | 960 |
| Arg | Leu | Gln | Ala | Ala | Pro | Arg | Ala | Glu | Ser | Gly | Leu | Leu | Asp | Gly | Val | |
| 305 | | | | | 310 | | | | | 315 | | | | | 320 | |
| ATG | ATG | ACC | GAT | GCA | GCC | CTG | CTC | TAC | GAT | GCG | GTC | CAC | ATT | GTG | TCT | 1008 |
| Met | Met | Thr | Asp | Ala | Ala | Leu | Leu | Tyr | Asp | Ala | Val | His | Ile | Val | Ser | |
| | | | | 325 | | | | | 330 | | | | | 335 | | |
| GTG | TGC | TAC | CAG | CGA | GCG | CCG | CAG | ATG | ACT | GTG | AAC | TCC | CTA | CAG | TGC | 1056 |
| Val | Cys | Tyr | Gln | Arg | Ala | Pro | Gln | Met | Thr | Val | Asn | Ser | Leu | Gln | Cys | |
| | | | 340 | | | | | 345 | | | | | 350 | | | |
| CAT | CGG | CAC | AAG | GCC | TGG | CGC | TTC | GGT | GGC | CGC | TTC | ATG | AAC | TTC | ATC | 1104 |
| His | Arg | His | Lys | Ala | Trp | Arg | Phe | Gly | Gly | Arg | Phe | Met | Asn | Phe | Ile | |
| | | 355 | | | | | 360 | | | | | 365 | | | | |
| AAG | GAG | GCT | CAA | TGG | GAA | GGA | TTA | ACT | GGA | CGG | ATT | GTT | TTC | AAC | AAA | 1152 |
| Lys | Glu | Ala | Gln | Trp | Glu | Gly | Leu | Thr | Gly | Arg | Ile | Val | Phe | Asn | Lys | |
| | 370 | | | | | 375 | | | | | 380 | | | | | |
| ACC | AGT | GGC | TTG | CGG | ACT | GAT | TTT | GAT | CTG | GAC | ATC | ATC | AGC | CTC | AAG | 1200 |
| Thr | Ser | Gly | Leu | Arg | Thr | Asp | Phe | Asp | Leu | Asp | Ile | Ile | Ser | Leu | Lys | |
| 385 | | | | | 390 | | | | | 395 | | | | | 400 | |
| GAA | GAT | GGC | CTC | GAG | AAG | GTC | GGG | GTG | TGG | AGT | CCA | GCT | GAC | GGT | CTC | 1248 |
| Glu | Asp | Gly | Leu | Glu | Lys | Val | Gly | Val | Trp | Ser | Pro | Ala | Asp | Gly | Leu | |
| | | | | 405 | | | | | 410 | | | | | 415 | | |
| AAT | ATC | ACT | GAG | GTT | GCC | AAA | GGC | CGA | GGT | CCT | AAT | GTC | ACC | GAC | TCT | 1296 |
| Asn | Ile | Thr | Glu | Val | Ala | Lys | Gly | Arg | Gly | Pro | Asn | Val | Thr | Asp | Ser | |
| | | | 420 | | | | | 425 | | | | | 430 | | | |

```
CTG ACC AAC AGG TCA CTC ATC GTC ACC ACT CTG CTG GAG GAG CCT TTT    1344
Leu Thr Asn Arg Ser Leu Ile Val Thr Thr Leu Leu Glu Glu Pro Phe
        435             440             445

GTC ATG TTC CGC AAG TCT GAT AGG ACC CTT TAC GGC AAT GAC CGG TTC    1392
Val Met Phe Arg Lys Ser Asp Arg Thr Leu Tyr Gly Asn Asp Arg Phe
    450             455             460

GAG GGC TAC TGC ATC GAC TTG CTC AAG GAG CTG GCG CAC ATC CTG GGC    1440
Glu Gly Tyr Cys Ile Asp Leu Leu Lys Glu Leu Ala His Ile Leu Gly
465             470             475             480

TTC TCC TAC GAG ATC CGG CTG GTG GAA GAC GGC AAG TAC GGG GCA CAG    1488
Phe Ser Tyr Glu Ile Arg Leu Val Glu Asp Gly Lys Tyr Gly Ala Gln
                485             490             495

GAC GAC AAG GGC CAG TGG AAC GGC ATG GTC AAG GAA CTC ATT GAC CAC    1536
Asp Asp Lys Gly Gln Trp Asn Gly Met Val Lys Glu Leu Ile Asp His
            500             505             510

AAA GCA GAT CTG GCT GTG GCT CCC CTG ACC ATC ACC CAT GTC CGA GAG    1584
Lys Ala Asp Leu Ala Val Ala Pro Leu Thr Ile Thr His Val Arg Glu
        515             520             525

AAG GCC ATT GAC TTC TCT AAG CCT TTT ATG ACC CTC GGA GTG AGC ATC    1632
Lys Ala Ile Asp Phe Ser Lys Pro Phe Met Thr Leu Gly Val Ser Ile
    530             535             540

TTA TAT CGA AAA CCC AAT GGC ACC AAC CCC AGT GTC TTC TCC TTC CTC    1680
Leu Tyr Arg Lys Pro Asn Gly Thr Asn Pro Ser Val Phe Ser Phe Leu
545             550             555             560

AAC CCC CTG TCC CCA GAC ATC TGG ATG TAC GTG CTA CTC GCC TAC CTG    1728
Asn Pro Leu Ser Pro Asp Ile Trp Met Tyr Val Leu Leu Ala Tyr Leu
                565             570             575

GGT GTC AGC TGT GTC CTC TTC GTC ATT GCC AGA TTC AGC CCT TAT GAA    1776
Gly Val Ser Cys Val Leu Phe Val Ile Ala Arg Phe Ser Pro Tyr Glu
            580             585             590

TGG TAT GAT GCC CAC CCC TGC AAC CCC GGC TCT GAG GTG GTG GAG AAT    1824
Trp Tyr Asp Ala His Pro Cys Asn Pro Gly Ser Glu Val Val Glu Asn
        595             600             605

AAC TTC ACG CTG CTC AAC AGC TTC TGG TTT GGA ATG GGC TCC CTG ATG    1872
Asn Phe Thr Leu Leu Asn Ser Phe Trp Phe Gly Met Gly Ser Leu Met
    610             615             620

CAA CAA GGA TCT GAA CTG ATG CCC AAA GCT CTG TCT ACC CGC ATC ATT    1920
Gln Gln Gly Ser Glu Leu Met Pro Lys Ala Leu Ser Thr Arg Ile Ile
625             630             635             640

GGC GGC ATC TGG TGG TTC TTC ACC CTT ATT ATC ATC TCC TCC TAC ACG    1968
Gly Gly Ile Trp Trp Phe Phe Thr Leu Ile Ile Ile Ser Ser Tyr Thr
                645             650             655

GCC AAC CTG GCT GCC TTC CTG ACC GTG GAG CGC ATG GAG TCA CCC ATC    2016
Ala Asn Leu Ala Ala Phe Leu Thr Val Glu Arg Met Glu Ser Pro Ile
            660             665             670

GAC TCT GCC GAT GAC CTG GCC AAG CAG ACC AAA ATA GAG TAC GGT GCT    2064
Asp Ser Ala Asp Asp Leu Ala Lys Gln Thr Lys Ile Glu Tyr Gly Ala
        675             680             685

GTC AAG GAT GGG GCC ACC ATG ACC TTC TTC AAG AAA TCC AAG ATC TCC    2112
Val Lys Asp Gly Ala Thr Met Thr Phe Phe Lys Lys Ser Lys Ile Ser
    690             695             700

ACC TTT GAG AAG ATG TGG GCC TTC ATG AGC AGC AAG CCC TCG GCT CTG    2160
Thr Phe Glu Lys Met Trp Ala Phe Met Ser Ser Lys Pro Ser Ala Leu
705             710             715             720

GTG AAG AAC AAT GAG GAG GGC ATC CAG CGG ACA CTC ACA GCT GAC TAC    2208
Val Lys Asn Asn Glu Glu Gly Ile Gln Arg Thr Leu Thr Ala Asp Tyr
                725             730             735

GCT CTG CTC ATG GAG TCC ACG ACC ATA GAG TAC ATC ACA CAA AGG AAC    2256
Ala Leu Leu Met Glu Ser Thr Thr Ile Glu Tyr Ile Thr Gln Arg Asn
            740             745             750
```

| | | | | | | | | | | | | | | | | |
|---|---|---|---|---|---|---|---|---|---|---|---|---|---|---|---|---|
| TGC | AAT | CTC | ACC | CAG | ATC | GGC | GGC | CTC | ATC | GAT | TCC | AAG | GGC | TAC | GGC | 2304 |
| Cys | Asn | Leu | Thr | Gln | Ile | Gly | Gly | Leu | Ile | Asp | Ser | Lys | Gly | Tyr | Gly | |
| | | 755 | | | | 760 | | | | | 765 | | | | | |
| ATC | GGC | ACG | CCC | ATG | GGC | TCC | CCC | TAC | AGG | GAC | AAA | ATC | ACC | ATC | GCC | 2352 |
| Ile | Gly | Thr | Pro | Met | Gly | Ser | Pro | Tyr | Arg | Asp | Lys | Ile | Thr | Ile | Ala | |
| | 770 | | | | | 775 | | | | | 780 | | | | | |
| ATT | CTG | CAG | CTG | CAG | GAG | GAG | GAC | AAG | CTG | CAC | ATC | ATG | AAG | GAG | AAG | 2400 |
| Ile | Leu | Gln | Leu | Gln | Glu | Glu | Asp | Lys | Leu | His | Ile | Met | Lys | Glu | Lys | |
| 785 | | | | | 790 | | | | | 795 | | | | | 800 | |
| TGG | TGG | CGA | GGC | AGC | GGG | TGC | CCC | GAG | GAG | GAG | AAC | AAG | GAG | GCC | AGC | 2448 |
| Trp | Trp | Arg | Gly | Ser | Gly | Cys | Pro | Glu | Glu | Glu | Asn | Lys | Glu | Ala | Ser | |
| | | | | 805 | | | | | 810 | | | | | 815 | | |
| GCA | CTG | GGC | ATC | CAG | AAG | ATT | GGC | GGC | ATC | TTC | ATC | GTC | CTG | GCT | GCC | 2496 |
| Ala | Leu | Gly | Ile | Gln | Lys | Ile | Gly | Gly | Ile | Phe | Ile | Val | Leu | Ala | Ala | |
| | | | 820 | | | | | 825 | | | | | 830 | | | |
| GGC | TTA | GTC | CTG | TCC | GTG | TTG | GTG | GCA | GTG | GGC | GAG | TTT | ATA | TAC | AAA | 2544 |
| Gly | Leu | Val | Leu | Ser | Val | Leu | Val | Ala | Val | Gly | Glu | Phe | Ile | Tyr | Lys | |
| | | 835 | | | | | 840 | | | | | 845 | | | | |
| CTC | CGC | AAG | ACA | GCG | GAA | CGG | GAG | CAG | CGC | TCT | TTC | TGC | AGC | ACA | GTG | 2592 |
| Leu | Arg | Lys | Thr | Ala | Glu | Arg | Glu | Gln | Arg | Ser | Phe | Cys | Ser | Thr | Val | |
| | 850 | | | | | 855 | | | | | 860 | | | | | |
| GCC | GAC | GAG | ATC | CGC | TTC | TCC | CTC | ACC | TGC | CAG | CGG | CGT | CTC | AAG | CAC | 2640 |
| Ala | Asp | Glu | Ile | Arg | Phe | Ser | Leu | Thr | Cys | Gln | Arg | Arg | Leu | Lys | His | |
| 865 | | | | | 870 | | | | | 875 | | | | | 880 | |
| AAG | CCA | CAG | CCT | CCT | ATG | ATG | GTC | AAG | ACA | GAT | GCG | GTT | ATC | AAC | ATG | 2688 |
| Lys | Pro | Gln | Pro | Pro | Met | Met | Val | Lys | Thr | Asp | Ala | Val | Ile | Asn | Met | |
| | | | | 885 | | | | | 890 | | | | | 895 | | |
| CAC | ACC | TTT | AAT | GAC | CGA | AGG | CTT | CCA | GGC | AAG | GAC | AGC | ATG | AGC | TGC | 2736 |
| His | Thr | Phe | Asn | Asp | Arg | Arg | Leu | Pro | Gly | Lys | Asp | Ser | Met | Ser | Cys | |
| | | | 900 | | | | | 905 | | | | | 910 | | | |
| AGC | ACC | TCG | CTA | GCC | CCT | GTC | TTC | CCT | TAGACTTGGG | TCCAGCGGGG | | | | | | 2783 |
| Ser | Thr | Ser | Leu | Ala | Pro | Val | Phe | Pro | | | | | | | | |
| | | 915 | | | | | 920 | | | | | | | | | |

| | |
|---|---|
| ACTTCAGGCC CGGTCCACGC AGAGGAAGGC AAAGGAGACC CGAAAGGACA TCCTCATCTC | 2843 |
| ATGCTGGCCT TGGGGATGGA GCTGCTGCCC GCATCCGGCT GTGAACCATC AGCTCTTACC | 2903 |
| TACCGGGGAA ACCCATGGGC CCTCAGCAGC TGCTTGGGCT TCATCTCCTC TTGTCTTTTT | 2963 |
| TGTGGCTTTC TGAAGCTGTG AAGGCCAGCG GAAGCACACG CCTCTCAGGC TGCACTCACC | 3023 |
| GACCATCTCC ATAGCCAGCT ACTTCGGCCA GGGCTCTGCA GAGGCCTCGG AACACCAGAG | 3083 |
| ATAGCTCTTA CACCTCCCTC CCTCCCCTCA AGTCCAGGCC TTCTAGCACG CACCCATGAG | 3143 |
| AGCAGAGACT CCAGCTCAGA ACGCCTTGAG GGTGTTCTGA GGAGGCCACC AGTGGGAGCC | 3203 |
| CCAAGGCAGC CATCCATACC TGGACAGAAG CAAAGCTTCA GCCCTTAAGG GCTATTCACC | 3263 |
| TGGGTCTGCC CTCCCCAACG TGGCTTCGCC CTCGTGCCGA ATTCGATATC AAGCTTATCG | 3323 |
| ATACCGTCGA CCTCGAGGGG G | 3344 |

( 2 ) INFORMATION FOR SEQ ID NO:14:

( i ) SEQUENCE CHARACTERISTICS:
        ( A ) LENGTH: 921 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | |
|---|---|---|---|---|---|---|---|---|---|---|---|---|---|---|
| Gly | Ala | Val | Ala | Gly | Ser | Leu | Gly | Arg | Leu | Arg | Ser | Leu | Val | Trp | Glu |
| 1 | | | | 5 | | | | | 10 | | | | | 15 | |

-continued

| | | | | | | | | | | | | | | |
|---|---|---|---|---|---|---|---|---|---|---|---|---|---|---|
| Tyr | Trp | Ala | Gly<br>20 | Phe | Leu | Val | Cys | Ala<br>25 | Phe | Trp | Ile | Pro | Asp<br>30 | Ser | Arg |
| Gly | Met | Pro | His<br>35 | Val | Ile | Arg | Ile | Gly<br>40 | Gly | Ile | Phe | Glu | Tyr<br>45 | Ala | Asp |
| Gly | Pro | Asn | Ala<br>50 | Gln | Val | Met | Asn<br>55 | Ala | Glu | Glu | His | Ala<br>60 | Phe | Arg | Phe |
| Ser<br>65 | Ala | Asn | Ile | Ile | Asn<br>70 | Arg | Asn | Arg | Thr | Leu<br>75 | Leu | Pro | Asn | Thr | Thr<br>80 |
| Leu | Thr | Tyr | Asp | Ile<br>85 | Gln | Arg | Ile | His | Phe<br>90 | His | Asp | Ser | Phe | Glu<br>95 | Ala |
| Thr | Lys | Lys | Ala<br>100 | Cys | Asp | Gln | Leu | Ala<br>105 | Leu | Gly | Val | Val | Ala<br>110 | Ile | Phe |
| Gly | Pro | Ser | Gln<br>115 | Gly | Ser | Cys | Ile | Asn<br>120 | Ala | Val | Gln | Ser<br>125 | Ile | Cys | Asn |
| Ala | Leu | Glu<br>130 | Val | Pro | His | Ile<br>135 | Gln | Leu | Arg | Trp | Lys<br>140 | His | His | Pro | Leu |
| Asp<br>145 | Asn | Lys | Asp | Thr | Phe<br>150 | Tyr | Val | Asn | Leu | Tyr<br>155 | Pro | Asp | Tyr | Ala | Ser<br>160 |
| Leu | Ser | His | Ala | Ile<br>165 | Leu | Asp | Leu | Val | Gln<br>170 | Ser | Leu | Lys | Trp | Arg<br>175 | Ser |
| Ala | Thr | Val | Val<br>180 | Tyr | Asp | Asp | Ser | Thr<br>185 | Gly | Leu | Ile | Arg | Leu<br>190 | Gln | Glu |
| Leu | Ile | Met<br>195 | Ala | Pro | Ser | Arg | Tyr<br>200 | Asn | Ile | Arg | Leu | Lys<br>205 | Ile | Arg | Gln |
| Leu | Pro<br>210 | Ile | Asp | Ser | Asp | Asp<br>215 | Ser | Arg | Pro | Leu | Leu<br>220 | Lys | Glu | Met | Lys |
| Arg<br>225 | Gly | Arg | Glu | Phe | Arg<br>230 | Ile | Ile | Phe | Asp | Cys<br>235 | Ser | His | Thr | Met | Ala<br>240 |
| Ala | Gln | Ile | Leu | Lys<br>245 | Gln | Ala | Met | Ala | Met<br>250 | Gly | Met | Met | Thr | Glu<br>255 | Tyr |
| Tyr | His | Phe | Ile<br>260 | Phe | Thr | Thr | Leu | Asp<br>265 | Leu | Tyr | Ala | Leu | Asp<br>270 | Leu | Glu |
| Pro | Tyr | Arg<br>275 | Tyr | Ser | Gly | Val | Asn<br>280 | Leu | Thr | Gly | Phe | Arg<br>285 | Ile | Leu | Asn |
| Val | Asp<br>290 | Asn | Pro | His | Val | Ser<br>295 | Ala | Ile | Val | Glu | Lys<br>300 | Trp | Ser | Met | Glu |
| Arg<br>305 | Leu | Gln | Ala | Ala | Pro<br>310 | Arg | Ala | Glu | Ser | Gly<br>315 | Leu | Leu | Asp | Gly | Val<br>320 |
| Met | Met | Thr | Asp | Ala<br>325 | Ala | Leu | Leu | Tyr | Asp<br>330 | Ala | Val | His | Ile | Val<br>335 | Ser |
| Val | Cys | Tyr | Gln<br>340 | Arg | Ala | Pro | Gln | Met<br>345 | Thr | Val | Asn | Ser | Leu<br>350 | Gln | Cys |
| His | Arg | His<br>355 | Lys | Ala | Trp | Arg | Phe<br>360 | Gly | Gly | Arg | Phe | Met<br>365 | Asn | Phe | Ile |
| Lys | Glu<br>370 | Ala | Gln | Trp | Glu | Gly<br>375 | Leu | Thr | Gly | Arg | Ile<br>380 | Val | Phe | Asn | Lys |
| Thr<br>385 | Ser | Gly | Leu | Arg | Thr<br>390 | Asp | Phe | Asp | Leu | Asp<br>395 | Ile | Ile | Ser | Leu | Lys<br>400 |
| Glu | Asp | Gly | Leu | Glu<br>405 | Lys | Val | Gly | Val | Trp<br>410 | Ser | Pro | Ala | Asp | Gly<br>415 | Leu |
| Asn | Ile | Thr | Glu<br>420 | Val | Ala | Lys | Gly | Arg<br>425 | Gly | Pro | Asn | Val | Thr<br>430 | Asp | Ser |
| Leu | Thr | Asn | Arg<br>435 | Ser | Leu | Ile | Val<br>440 | Thr | Thr | Leu | Leu | Glu<br>445 | Glu | Pro | Phe |

| | | | | | | | | | | | | | | |
|---|---|---|---|---|---|---|---|---|---|---|---|---|---|---|
| Val | Met | Phe | Arg | Lys | Ser | Asp | Arg | Thr | Leu | Tyr | Gly | Asn | Asp | Arg | Phe |
| | 450 | | | | 455 | | | | 460 | | | | | |
| Glu | Gly | Tyr | Cys | Ile | Asp | Leu | Leu | Lys | Glu | Leu | Ala | His | Ile | Leu | Gly |
| 465 | | | | | 470 | | | | 475 | | | | | | 480 |
| Phe | Ser | Tyr | Glu | Ile | Arg | Leu | Val | Glu | Asp | Gly | Lys | Tyr | Gly | Ala | Gln |
| | | | | 485 | | | | | 490 | | | | | 495 | |
| Asp | Asp | Lys | Gly | Gln | Trp | Asn | Gly | Met | Val | Lys | Glu | Leu | Ile | Asp | His |
| | | | 500 | | | | | 505 | | | | | 510 | | |
| Lys | Ala | Asp | Leu | Ala | Val | Ala | Pro | Leu | Thr | Ile | Thr | His | Val | Arg | Glu |
| | | 515 | | | | | 520 | | | | | 525 | | | |
| Lys | Ala | Ile | Asp | Phe | Ser | Lys | Pro | Phe | Met | Thr | Leu | Gly | Val | Ser | Ile |
| | | 530 | | | | 535 | | | | | 540 | | | | |
| Leu | Tyr | Arg | Lys | Pro | Asn | Gly | Thr | Asn | Pro | Ser | Val | Phe | Ser | Phe | Leu |
| 545 | | | | | 550 | | | | | 555 | | | | | 560 |
| Asn | Pro | Leu | Ser | Pro | Asp | Ile | Trp | Met | Tyr | Val | Leu | Leu | Ala | Tyr | Leu |
| | | | | 565 | | | | | 570 | | | | | 575 | |
| Gly | Val | Ser | Cys | Val | Leu | Phe | Val | Ile | Ala | Arg | Phe | Ser | Pro | Tyr | Glu |
| | | | 580 | | | | | 585 | | | | | 590 | | |
| Trp | Tyr | Asp | Ala | His | Pro | Cys | Asn | Pro | Gly | Ser | Glu | Val | Val | Glu | Asn |
| | | 595 | | | | 600 | | | | | 605 | | | | |
| Asn | Phe | Thr | Leu | Leu | Asn | Ser | Phe | Trp | Phe | Gly | Met | Gly | Ser | Leu | Met |
| | 610 | | | | 615 | | | | | 620 | | | | | |
| Gln | Gln | Gly | Ser | Glu | Leu | Met | Pro | Lys | Ala | Leu | Ser | Thr | Arg | Ile | Ile |
| 625 | | | | | 630 | | | | 635 | | | | | | 640 |
| Gly | Gly | Ile | Trp | Trp | Phe | Phe | Thr | Leu | Ile | Ile | Ile | Ser | Ser | Tyr | Thr |
| | | | | 645 | | | | | 650 | | | | | 655 | |
| Ala | Asn | Leu | Ala | Ala | Phe | Leu | Thr | Val | Glu | Arg | Met | Glu | Ser | Pro | Ile |
| | | | 660 | | | | | 665 | | | | | 670 | | |
| Asp | Ser | Ala | Asp | Asp | Leu | Ala | Lys | Gln | Thr | Lys | Ile | Glu | Tyr | Gly | Ala |
| | | 675 | | | | | 680 | | | | | 685 | | | |
| Val | Lys | Asp | Gly | Ala | Thr | Met | Thr | Phe | Phe | Lys | Lys | Ser | Lys | Ile | Ser |
| | 690 | | | | | 695 | | | | | 700 | | | | |
| Thr | Phe | Glu | Lys | Met | Trp | Ala | Phe | Met | Ser | Ser | Lys | Pro | Ser | Ala | Leu |
| 705 | | | | | 710 | | | | | 715 | | | | | 720 |
| Val | Lys | Asn | Asn | Glu | Glu | Gly | Ile | Gln | Arg | Thr | Leu | Thr | Ala | Asp | Tyr |
| | | | | 725 | | | | | 730 | | | | | 735 | |
| Ala | Leu | Leu | Met | Glu | Ser | Thr | Thr | Ile | Glu | Tyr | Ile | Thr | Gln | Arg | Asn |
| | | | 740 | | | | | 745 | | | | | 750 | | |
| Cys | Asn | Leu | Thr | Gln | Ile | Gly | Gly | Leu | Ile | Asp | Ser | Lys | Gly | Tyr | Gly |
| | | 755 | | | | | 760 | | | | | 765 | | | |
| Ile | Gly | Thr | Pro | Met | Gly | Ser | Pro | Tyr | Arg | Asp | Lys | Ile | Thr | Ile | Ala |
| | 770 | | | | | 775 | | | | | 780 | | | | |
| Ile | Leu | Gln | Leu | Gln | Glu | Glu | Asp | Lys | Leu | His | Ile | Met | Lys | Glu | Lys |
| 785 | | | | | 790 | | | | | 795 | | | | | 800 |
| Trp | Trp | Arg | Gly | Ser | Gly | Cys | Pro | Glu | Glu | Glu | Asn | Lys | Glu | Ala | Ser |
| | | | | 805 | | | | | 810 | | | | | 815 | |
| Ala | Leu | Gly | Ile | Gln | Lys | Ile | Gly | Gly | Ile | Phe | Ile | Val | Leu | Ala | Ala |
| | | | 820 | | | | | 825 | | | | | 830 | | |
| Gly | Leu | Val | Leu | Ser | Val | Leu | Val | Ala | Val | Gly | Glu | Phe | Ile | Tyr | Lys |
| | | 835 | | | | | 840 | | | | | 845 | | | |
| Leu | Arg | Lys | Thr | Ala | Glu | Arg | Glu | Gln | Arg | Ser | Phe | Cys | Ser | Thr | Val |
| | 850 | | | | | 855 | | | | | 860 | | | | |
| Ala | Asp | Glu | Ile | Arg | Phe | Ser | Leu | Thr | Cys | Gln | Arg | Arg | Leu | Lys | His |

-continued

```
865                    870                      875                      880

Lys Pro Gln Pro Pro Met Met Val Lys Thr Asp Ala Val Ile Asn Met
                885                  890                  895

His Thr Phe Asn Asp Arg Arg Leu Pro Gly Lys Asp Ser Met Ser Cys
            900                 905                 910

Ser Thr Ser Leu Ala Pro Val Phe Pro
        915             920
```